ns**

United States Patent [19]

Barrett et al.

[11] Patent Number: 5,786,331

[45] Date of Patent: Jul. 28, 1998

[54] PEPTIDES AND COMPOUNDS THAT BIND TO THE IL-1 RECEPTOR

[75] Inventors: Ronald W. Barrett, Sunnyvale; Stephen D. Yanofsky, San Mateo; David Baldwin, Palo Alto; Jeff W. Jacobs, San Mateo; Phillipe R. Bovy, Los Altos; Ellen M. Leahy, San Leandro, all of Calif.; Richard S. Pottorf, West Chester, Ohio

[73] Assignees: Affymax Technologies N.V., Greenford, England; Hoechst Marion Roussel, Inc., Kansas City, Mo.

[21] Appl. No.: 465,391

[22] Filed: Jun. 5, 1995

Related U.S. Application Data

[63] Continuation-in-part of Ser. No. 383,474, Feb. 1, 1995, which is a continuation-in-part of Ser. No. 190,788, Feb. 2, 1994, Pat. No. 5,608,035.

[51] Int. Cl.$^6$ .......................... A61K 38/08; A61K 38/00; C07K 7/04
[52] U.S. Cl. .................. 514/15; 514/12; 530/327; 530/324
[58] Field of Search ............................. 514/12–15

[56] References Cited

U.S. PATENT DOCUMENTS

| | | | |
|---|---|---|---|
| 4,968,607 | 11/1990 | Dower et al. | 435/69.1 |
| 5,039,790 | 8/1991 | Adams et al. | 530/324 |
| 5,075,222 | 12/1991 | Hannum et al. | 435/69.1 |
| 5,075,288 | 12/1991 | Krueger et al. | 514/12 |
| 5,077,219 | 12/1991 | Auron et al. | 435/320.1 |

FOREIGN PATENT DOCUMENTS

| | | |
|---|---|---|
| WO 91/00742 | 1/1991 | WIPO. |
| WO 91/08285 | 6/1991 | WIPO. |
| WO 91/17184 | 11/1991 | WIPO. |

OTHER PUBLICATIONS

Estrov, Z., Kurzrock, R., Talpaz, M. Role of Interleukin–1 inhibitory molecules in therapy of acute and chronic myelogenous leuemia. Leukemia and Lymphoma, 10, 407–418, 1993.
Bender et al., "Chapter 20: Pharmacological modulation of interleukin–1," *Ann. Rep. Med. Chem.* 25:185–191 (1989).
Cwirla et al., "Peptides on phage: A vast library of peptides for identifying ligands," *Proc. Natl. Acad. Sci. USA* 87:6378–6382 (1990).
Dinarello, "Interleukin–1 and interleukin–1 antagonism," *Blood* 77(8):1627–1652 (1991).
Dower et al., "The interleukin–1 receptor," *Immunol. Today* 8(2):46–51 (1987).
Dower et al., "Human cytokine receptors," *J. Clin. Immunol.* 10(6):289–299 (1990).

Evans et al., "Mapping receptor binding sites in interleukin (IL)–1 receptor antagonist and IL–1β by site–directed mutagenesis," *J. Biol. Chem.* 270(19):11477–11483 (May 12, 1995).
Fodor et al., "Light–directed, spatially addressable parallel chemical synthesis," *Science* 251:767–773 (Feb. 15, 1991).
Hannum et al., "Interleukin–1 receptor antagonist activity of a human interleukin–1 inhibitor," *Nature* 343:336–340 (1990).
Labriola–Tompkins et al., "Identification of the discontinuous binding site in human interleukin–1β for the type I interleukin 1 receptor," *Proc. Natl. Acad. Sci. USA* 88:11182–11186 (1991).
Larrick, "Native interleukin 1 inhibitors," *Immunol. Today* 10(2):61–66 (1989).
McMahan et al., "A novel IL–1 receptor, cloned from B cells by mammalian expression, is expressed in many cell types," *EMBO J.* 10(10):2821–2832 (1991).
Estrov et al. Role of interleukin–1 inhibitory molecules in therapy of acute and chronic myelogenous leukemia. Leukemia and Lymphoma, 10:407–418, Feb. 1993.

*Primary Examiner*—Cecilia J. Tsang
*Assistant Examiner*—Michael Borin
*Attorney, Agent, or Firm*—Matthew B. Murphy; Lauren L. Stevens

[57] ABSTRACT

Peptides that bind to the interleukin-1 type I receptor (IL-1RtI) can be used to assay the amount of IL-1R, or an IL-1R agonist or antagonist, in a sample and comprise a sequence of amino acids selected from the group consisting of (1) $WXXXGZ_1W$ where $Z_1$ is L, I, A, or Q; (2) $XXQZ_5YZ_6XX$ where $Z_5$ is P or Aze where Aze is azetidine; and $Z_6$ is S, A, V, or L; and (3) $Z_{23}NZ_{24}SZ_{25}Z_{26}Z_{27}Z_{28}Z_{29}Z_{30}L$ where $Z_{23}$ is D or Y; $Z_{24}$ is D or S; $Z_{25}$ is S or W; $Z_{26}$ is S or Y; $Z_{27}$ is D or V; $Z_{28}$ is S or W; $Z_{29}$ is F or L; and $Z_{30}$ is D or L; and where each amino acid is indicated by standard one letter abbreviation; and each X can be selected from any one of the 20 genetically coded L-amino acids or the stereoisomeric D-amino acids. Also provided are peptides which bind to the IL-1RtI, which are 11 to 40 amino acids in length, which comprise the core sequence of amino acids:

$$Z_{31}XWZ_{32}Z_{33}Z_{34}Z_{35}Z_{36}QZ_{37}Z_{38}$$

where each letter represents the standard one letter abbreviation for an amino acid or an analog thereof; X is selected from the group of natural or unnatural amino acids; $Z_{37}$ is a natural or unnatural cyclic amino acid; $Z_{31}$ is selected from phenylalanine and acetylated phenylalanine; $Z_{32}$ is a natural or unnatural amino acid; $Z_{33}$ is selected from proline and pipecolic acid; $Z_{34}$ is selected from glycine, d-alanine, d-valine, sarcosine and aminoisobutyric acid; $Z_{35}$ is a natural or unnatural amino acid and $Z_{36}$ is selected from tyrosine, phosphotyrosine, phenylalanine and tryptophan; and $Z_{38}$ is selected from tyrosinamide and substituted tyrosinamide.

1 Claim, No Drawings

SEQUENCE LISTING ( 1 ) GENERAL INFORMATION:

( i i i ) NUMBER OF SEQUENCES: 405

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(2, 3, 4)
        ( D ) OTHER INFORMATION: /note="Xaa is any amino acid."

( i x ) FEATURE:
        ( A ) NAME/KEY: Region
        ( B ) LOCATION: 6
        ( D ) OTHER INFORMATION: /note="Xaa is Leu, Ile, Ala or Gln."

( x i ) SEQUENCE DESCRIPTION: SEQ ID NO:1:

Trp Xaa Xaa Xaa Gly Xaa Trp
1               5

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(3, 4)
        ( D ) OTHER INFORMATION: /note="Xaa is any amino acid."

( i x ) FEATURE:
        ( A ) NAME/KEY: Region
        ( B ) LOCATION: 2
        ( D ) OTHER INFORMATION: /note="Xaa is Asp, Gly, Asn, Ser, or Thr."

( i x ) FEATURE:
        ( A ) NAME/KEY: Region
        ( B ) LOCATION: 6
        ( D ) OTHER INFORMATION: /note="Xaa is Leu, Ile, Ala or Gln."

( x i ) SEQUENCE DESCRIPTION: SEQ ID NO:2:

Trp Xaa Xaa Xaa Gly Xaa Trp
1               5

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear (i i) MOLECULE TYPE: peptide (i x) FEATURE:
    (A) NAME/KEY: Region
    (B) LOCATION: 2
    (D) OTHER INFORMATION: /note="Xaa is Asp, Gly, Asn, Ser or Thr."

(i x) FEATURE:
    (A) NAME/KEY: Region
    (B) LOCATION: 3
    (D) OTHER INFORMATION: /note="Xaa is Asp, Glu, His, Met, Asn Gln, Arg, Ser, Thr or Val."

(i x) FEATURE:
    (A) NAME/KEY: Region
    (B) LOCATION: 4
    (D) OTHER INFORMATION: /note="Xaa is Ala, Asp, His, Phe, Lys Asn, Gln, Arg, Thr or Tyr."

(i x) FEATURE:
    (A) NAME/KEY: Region
    (B) LOCATION: 6
    (D) OTHER INFORMATION: /note="Xaa is Leu, Ile, Ala or Gln."

(x i) SEQUENCE DESCRIPTION: SEQ ID NO:3:

```
Trp  Xaa  Xaa  Xaa  Gly  Xaa  Trp
1                    5
```

(2) INFORMATION FOR SEQ ID NO:4:

(i) SEQUENCE CHARACTERISTICS:
    (A) LENGTH: 7 amino acids
    (B) TYPE: amino acid
    (C) STRANDEDNESS: single
    (D) TOPOLOGY: linear (i i) MOLECULE TYPE: peptide (i x) FEATURE:
    (A) NAME/KEY: Region
    (B) LOCATION: 2
    (D) OTHER INFORMATION: /note="Xaa is Asp, Ser or Thr."

(i x) FEATURE:
    (A) NAME/KEY: Region
    (B) LOCATION: 3
    (D) OTHER INFORMATION: /note="Xaa is Asp, Glu, or Thr."

(i x) FEATURE:
    (A) NAME/KEY: Region
    (B) LOCATION: 4
    (D) OTHER INFORMATION: /note="Xaa is Asp, His, Asn, Arg or Thr."

(i x) FEATURE:
    (A) NAME/KEY: Region
    (B) LOCATION: 6
    (D) OTHER INFORMATION: /note="Xaa is Leu or Ile."

(x i) SEQUENCE DESCRIPTION: SEQ ID NO:4:

```
Trp  Xaa  Xaa  Xaa  Gly  Xaa  Trp
1                    5
```

(2) INFORMATION FOR SEQ ID NO:5:

(i) SEQUENCE CHARACTERISTICS:
    (A) LENGTH: 10 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:5:

Ser Trp Asp Thr Arg Gly Leu Trp Val Glu
1               5                   10

( 2 ) INFORMATION FOR SEQ ID NO:6:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Region
      ( B ) LOCATION: one-of(1, 2, 7, 8)
      ( D ) OTHER INFORMATION: /note="Xaa is any amino acid."

( i x ) FEATURE:
      ( A ) NAME/KEY: Region
      ( B ) LOCATION: 4
      ( D ) OTHER INFORMATION: /note="Xaa is Pro or Azetidine."

( i x ) FEATURE:
      ( A ) NAME/KEY: Region
      ( B ) LOCATION: 6
      ( D ) OTHER INFORMATION: /note="Xaa is Ser, Ala, Val or Leu."

( x i ) SEQUENCE DESCRIPTION: SEQ ID NO:6:

Xaa Xaa Gln Xaa Tyr Xaa Xaa Xaa
1               5

( 2 ) INFORMATION FOR SEQ ID NO:7:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Region
      ( B ) LOCATION: 1
      ( D ) OTHER INFORMATION: /note="Xaa is Tyr, Trp or Phe."

( i x ) FEATURE:
      ( A ) NAME/KEY: Region
      ( B ) LOCATION: one-of(2, 7, 8)
      ( D ) OTHER INFORMATION: /note="Xaa is any amino acid."

( i x ) FEATURE:
      ( A ) NAME/KEY: Region
      ( B ) LOCATION: 4
      ( D ) OTHER INFORMATION: /note="Xaa is Pro or Azetidine."

( i x ) FEATURE:
      ( A ) NAME/KEY: Region
      ( B ) LOCATION: 6
      ( D ) OTHER INFORMATION: /note="Xaa is Ser, Ala, Val or Leu."

( x i ) SEQUENCE DESCRIPTION: SEQ ID NO:7:

Xaa Xaa Gln Xaa Tyr Xaa Xaa Xaa
1               5

( 2 ) INFORMATION FOR SEQ ID NO:8:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
    ( A ) NAME/KEY: Region
    ( B ) LOCATION: 1
    ( D ) OTHER INFORMATION: /note="Xaa is Tyr, Trp or Phe."

( i x ) FEATURE:
    ( A ) NAME/KEY: Region
    ( B ) LOCATION: 2
    ( D ) OTHER INFORMATION: /note="Xaa is Glu, Phe, Val, Trp or Tyr."

( i x ) FEATURE:
    ( A ) NAME/KEY: Region
    ( B ) LOCATION: 4
    ( D ) OTHER INFORMATION: /note="Xaa is Pro or Azetidine."

( i x ) FEATURE:
    ( A ) NAME/KEY: Region
    ( B ) LOCATION: 6
    ( D ) OTHER INFORMATION: /note="Xaa is Ser, Ala, Val or Leu."

( i x ) FEATURE:
    ( A ) NAME/KEY: Region
    ( B ) LOCATION: 7
    ( D ) OTHER INFORMATION: /note="Xaa is Met, Phe, Val, Arg, Gln, Lys, Thr, Ser, Asp, Leu, Ile or Glu."

( i x ) FEATURE:
    ( A ) NAME/KEY: Region
    ( B ) LOCATION: 8
    ( D ) OTHER INFORMATION: /note="Xaa is Glu, Leu, Trp, Val, His, Ile, Gly, Ala, Asp, Leu, Tyr, Asn, Gln or Pro."

( x i ) SEQUENCE DESCRIPTION: SEQ ID NO:8:

Xaa Xaa Gln Xaa Tyr Xaa Xaa Xaa
1                      5

( 2 ) INFORMATION FOR SEQ ID NO:9:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 1
        ( D ) OTHER INFORMATION: /note="Xaa is Val, Leu, Ile, Glu, Pro, Gly, Tyr, Met, Thr or Asp."

( i x ) FEATURE:
        ( A ) NAME/KEY: Region
        ( B ) LOCATION: 2
        ( D ) OTHER INFORMATION: /note="Xaa is Tyr, Trp or Phe."

( i x ) FEATURE:
        ( A ) NAME/KEY: Region
        ( B ) LOCATION: 3
        ( D ) OTHER INFORMATION: /note="Xaa is Glu, Phe, Val, Trp or Tyr."

( i x ) FEATURE:
        ( A ) NAME/KEY: Region
        ( B ) LOCATION: 5
        ( D ) OTHER INFORMATION: /note="Xaa is Pro or Azetidine."

( i x ) FEATURE:
        ( A ) NAME/KEY: Region
        ( B ) LOCATION: 7
        ( D ) OTHER INFORMATION: /note="Xaa is Ser, Ala, Val or Leu."

-continued ( i x ) FEATURE:
    ( A ) NAME/KEY: Region
    ( B ) LOCATION: 8
    ( D ) OTHER INFORMATION: /note="Xaa is Met, Phe, Val, Arg, Gln, Lys, Thr, Ser, Asp, Leu, Ile or Glu."

( i x ) FEATURE:
    ( A ) NAME/KEY: Region
    ( B ) LOCATION: 9
    ( D ) OTHER INFORMATION: /note="Xaa is Glu, Leu, Trp, Val, His, Ile, Gly, Ala, Asp, Leu, Tyr, Asn, Gln or Pro."

( x i ) SEQUENCE DESCRIPTION: SEQ ID NO:9:

Xaa Xaa Xaa Gln Xaa Tyr Xaa Xaa Xaa
1               5

( 2 ) INFORMATION FOR SEQ ID NO:10:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 1
        ( D ) OTHER INFORMATION: /note="Xaa is Ala, Asp, Glu, Phe, Gly, Lys, Gln, Ser, Thr, Val or Tyr."

( i x ) FEATURE:
        ( A ) NAME/KEY: Region
        ( B ) LOCATION: 2
        ( D ) OTHER INFORMATION: /note="Xaa is Ala, Asp, Gly, Ile, Asn, Pro, Ser, Thr, Val or Trp."

( i x ) FEATURE:
        ( A ) NAME/KEY: Region
        ( B ) LOCATION: 3
        ( D ) OTHER INFORMATION: /note="Xaa is Ala, Asp, Gly, Leu, Asn, Pro, Ser, Thr, Trp or Tyr."

( i x ) FEATURE:
        ( A ) NAME/KEY: Region
        ( B ) LOCATION: 4
        ( D ) OTHER INFORMATION: /note="Xaa is Ala, Asp, Glu, Phe, Leu, Asn, Arg, Val or Tyr."

( i x ) FEATURE:
        ( A ) NAME/KEY: Region
        ( B ) LOCATION: 5
        ( D ) OTHER INFORMATION: /note="Xaa is Ala, Asp, Glu, Gln, Arg, Ser or Thr."

( i x ) FEATURE:
        ( A ) NAME/KEY: Region
        ( B ) LOCATION: 6
        ( D ) OTHER INFORMATION: /note="Xaa is His, Ile, Leu, Pro, Ser, Thr or Trp."

( i x ) FEATURE:
        ( A ) NAME/KEY: Region
        ( B ) LOCATION: 7
        ( D ) OTHER INFORMATION: /note="Xaa is Ala, Glu, Phe, Lys, Asn, Gln, Arg, Ser or Tyr."

( i x ) FEATURE:
        ( A ) NAME/KEY: Region
        ( B ) LOCATION: 8
        ( D ) OTHER INFORMATION: /note="Xaa is Asp, Glu, Phe, Gln, Arg, Thr or Trp."

( i x ) FEATURE:
        ( A ) NAME/KEY: Region (B) LOCATION: 9
(D) OTHER INFORMATION: /note="Xaa is Ala, Asp, Pro, Ser, Thr or Trp."

(ix) FEATURE:
(A) NAME/KEY: Region
(B) LOCATION: 10
(D) OTHER INFORMATION: /note="Xaa is Ala, Asp, Gly, Lys, Asn, Gln, Ser or Thr."

(ix) FEATURE:
(A) NAME/KEY: Region
(B) LOCATION: 11
(D) OTHER INFORMATION: /note="Xaa is Ala, Glu, Leu, Pro, Ser, Thr, Val or Tyr."

(ix) FEATURE:
(A) NAME/KEY: Region
(B) LOCATION: 12
(D) OTHER INFORMATION: /note="Xaa is Val, Leu, Ile, Glu, Pro, Gly, Tyr, Met, Thr or Asp."

(ix) FEATURE:
(A) NAME/KEY: Region
(B) LOCATION: 13
(D) OTHER INFORMATION: /note="Xaa is Tyr, Trp or Phe."

(ix) FEATURE:
(A) NAME/KEY: Region
(B) LOCATION: 14
(D) OTHER INFORMATION: /note="Xaa is Tyr, Trp or Phe."

(ix) FEATURE:
(A) NAME/KEY: Region
(B) LOCATION: 16
(D) OTHER INFORMATION: /note="Xaa is Pro or Azetidine."

(ix) FEATURE:
(A) NAME/KEY: Region
(B) LOCATION: 18
(D) OTHER INFORMATION: /note="Xaa is Ser, Ala, Val, or Leu."

(ix) FEATURE:
(A) NAME/KEY: Region
(B) LOCATION: 19
(D) OTHER INFORMATION: /note="Xaa is Val, Leu, Ile or Glu."

(ix) FEATURE:
(A) NAME/KEY: Region
(B) LOCATION: 20
(D) OTHER INFORMATION: /note="Xaa is Gln or Pro."

(xi) SEQUENCE DESCRIPTION: SEQ ID NO:10:

```
Xaa Xaa Xaa Xaa Xaa Xaa Xaa Xaa Xaa Xaa Xaa Xaa Xaa Xaa Gln Xaa
1               5                   10                  15
Tyr Xaa Xaa Xaa Leu
            20
```

(2) INFORMATION FOR SEQ ID NO:11:

(i) SEQUENCE CHARACTERISTICS:
(A) LENGTH: 21 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:11:

```
Thr Ala Asn Val Ser Ser Phe Glu Trp Thr Pro Gly Tyr Trp Gln Pro
1               5                   10                  15
Tyr Ala Leu Pro Leu
            20
```

( 2 ) INFORMATION FOR SEQ ID NO:12:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Ser Trp Thr Asp Tyr Gly Tyr Trp Gln Pro Tyr Ala Leu Pro Ile Ser
1               5                   10                  15
Gly Leu
```

( 2 ) INFORMATION FOR SEQ ID NO:13:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
Glu Thr Pro Phe Thr Trp Glu Glu Ser Asn Ala Tyr Tyr Trp Gln Pro
1               5                   10                  15
Tyr Ala Leu Pro Leu
                20
```

( 2 ) INFORMATION FOR SEQ ID NO:14:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
Glu Asn Thr Tyr Ser Pro Asn Trp Ala Asp Ser Met Tyr Trp Gln Pro
1               5                   10                  15
Tyr Ala Leu Pro Leu
                20
```

( 2 ) INFORMATION FOR SEQ ID NO:15:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
Ser Val Gly Glu Asp His Asn Phe Trp Thr Ser Glu Tyr Trp Gln Pro
1               5                   10                  15
Tyr Ala Leu Pro Leu
                20
```

( 2 ) INFORMATION FOR SEQ ID NO:16:

( i ) SEQUENCE CHARACTERISTICS:
        ( A ) LENGTH: 21 amino acids
        ( B ) TYPE: amino acid (C) STRANDEDNESS: single
(D) TOPOLOGY: linear (ii) MOLECULE TYPE: peptide (xi) SEQUENCE DESCRIPTION: SEQ ID NO:16:

Asp Gly Tyr Asp Arg Trp Arg Gln Ser Gly Glu Arg Tyr Trp Gln Pro
1               5                   10                  15
Tyr Ala Leu Pro Leu
            20

(2) INFORMATION FOR SEQ ID NO:17:

(i) SEQUENCE CHARACTERISTICS:
    (A) LENGTH: 11 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Region
    (B) LOCATION: 1
    (D) OTHER INFORMATION: /note="Xaa is Asp or Tyr."

(ix) FEATURE:
    (A) NAME/KEY: Region
    (B) LOCATION: 3
    (D) OTHER INFORMATION: /note="Xaa is Asp, Ser, Thr."

(ix) FEATURE:
    (A) NAME/KEY: Region
    (B) LOCATION: 4
    (D) OTHER INFORMATION: /note="Xaa is Ser, Thr or Ala."

(ix) FEATURE:
    (A) NAME/KEY: Region
    (B) LOCATION: 5
    (D) OTHER INFORMATION: /note="Xaa is Ser or Trp."

(ix) FEATURE:
    (A) NAME/KEY: Region
    (B) LOCATION: 6
    (D) OTHER INFORMATION: /note="Xaa is Ser or Tyr."

(ix) FEATURE:
    (A) NAME/KEY: Region
    (B) LOCATION: 7
    (D) OTHER INFORMATION: /note="Xaa is Asp, Gln, Glu or
        Val."

(ix) FEATURE:
    (A) NAME/KEY: Region
    (B) LOCATION: 8
    (D) OTHER INFORMATION: /note="Xaa is Asn, Ser, Lys, His or
        Trp."

(ix) FEATURE:
    (A) NAME/KEY: Region
    (B) LOCATION: 9
    (D) OTHER INFORMATION: /note="Xaa is Phe or Leu."

(ix) FEATURE:
    (A) NAME/KEY: Region
    (B) LOCATION: 10
    (D) OTHER INFORMATION: /note="Xaa is Asp, Asn, Ser or Leu."

(ix) FEATURE:
    (A) NAME/KEY: Region
    (B) LOCATION: 11
    (D) OTHER INFORMATION: /note="Xaa is Leu, Ile, Gln, Met or
        Ala."

(xi) SEQUENCE DESCRIPTION: SEQ ID NO:17:

Xaa Asn Xaa Xaa Xaa Xaa Xaa Xaa Xaa Xaa Xaa ( 2 ) INFORMATION FOR SEQ ID NO:18:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

```
Trp Trp Thr Asp Thr Gly Leu Trp
 1               5
```

( 2 ) INFORMATION FOR SEQ ID NO:19:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

```
Trp Trp Thr Asp Asp Gly Leu Trp
 1               5
```

( 2 ) INFORMATION FOR SEQ ID NO:20:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

```
Trp Trp Asp Thr Arg Gly Leu Trp Val Trp Thr Ile
 1               5                   10
```

( 2 ) INFORMATION FOR SEQ ID NO:21:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

```
Phe Trp Gly Asn Asp Gly Ile Trp Leu Glu Ser Gly
 1               5                   10
```

( 2 ) INFORMATION FOR SEQ ID NO:22:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

```
Asp Trp Asp Gln Phe Gly Leu Trp Arg Gly Ala Ala
```

(2) INFORMATION FOR SEQ ID NO:23:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
Arg Trp Asp Asp Asn Gly Leu Trp Val Val Val Leu
 1               5                  10
```

(2) INFORMATION FOR SEQ ID NO:24:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

```
Ser Gly Met Trp Ser His Tyr Gly Ile Trp Met Gly
 1               5                  10
```

(2) INFORMATION FOR SEQ ID NO:25:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

```
Gly Gly Arg Trp Asp Gln Ala Gly Leu Trp Val Ala
 1               5                  10
```

(2) INFORMATION FOR SEQ ID NO:26:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

```
Lys Leu Trp Ser Glu Gln Gly Ile Trp Met Gly Glu
 1               5                  10
```

(2) INFORMATION FOR SEQ ID NO:27:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

```
Cys Trp Ser Met His Gly Leu Trp Leu Cys
```

```
         1               5                         1 0
```

(2) INFORMATION FOR SEQ ID NO:28:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

```
Gly Cys Trp Asp Asn Thr Gly Ile Trp Val Pro Cys
1               5                   1 0
```

(2) INFORMATION FOR SEQ ID NO:29:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

```
Asp Trp Asp Thr Arg Gly Leu Trp Val Tyr
1               5                   1 0
```

(2) INFORMATION FOR SEQ ID NO:30:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

```
Ser Leu Trp Asp Glu Asn Gly Ala Trp Ile
1               5                   1 0
```

(2) INFORMATION FOR SEQ ID NO:31:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:31:

```
Lys Trp Asp Asp Arg Gly Leu Trp Met His
1               5                   1 0
```

(2) INFORMATION FOR SEQ ID NO:32:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:32:

```
Gln Ala Trp Asn Glu Arg Gly Leu Trp Thr
```

(2) INFORMATION FOR SEQ ID NO:33:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:33:

```
Gln Trp Asp Thr Arg Gly Leu Trp Val Ala
 1               5                   10
```

(2) INFORMATION FOR SEQ ID NO:34:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:34:

```
Trp Asn Val His Gly Ile Trp Gln Glu
 1               5
```

(2) INFORMATION FOR SEQ ID NO:35:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:35:

```
Asp Trp Asp Thr Arg Gly Leu Trp Val Ala
 1               5                   10
```

(2) INFORMATION FOR SEQ ID NO:36:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

```
Ser Trp Gly Arg Asp Gly Leu Trp Ile Glu
 1               5                   10
```

(2) INFORMATION FOR SEQ ID NO:37:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:37:

```
Glu Trp Thr Asp Asn Gly Leu Trp Ala Leu
```

(2) INFORMATION FOR SEQ ID NO:38:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:38:

```
Ser Trp Asp Glu Lys Gly Leu Trp Ser Ala
1               5                   10
```

(2) INFORMATION FOR SEQ ID NO:39:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:39:

```
Ser Trp Asp Ser Ser Gly Leu Trp Met Asp
1               5                   10
```

(2) INFORMATION FOR SEQ ID NO:40:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:40:

```
Arg Leu Val Tyr Trp Gln Pro Tyr Ser Val Gln Arg
1               5                   10
```

(2) INFORMATION FOR SEQ ID NO:41:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:41:

```
Ser His Leu Tyr Trp Gln Pro Tyr Ser Val Gln
1               5                   10
```

(2) INFORMATION FOR SEQ ID NO:42:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:42:

```
Thr Leu Val Tyr Trp Gln Pro Tyr Ser Leu Gln Thr
```

(2) INFORMATION FOR SEQ ID NO:43:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:43:

```
Arg Gly Asp Tyr Trp Gln Pro Tyr Ser Val Gln Ser
 1               5                  10
```

(2) INFORMATION FOR SEQ ID NO:44:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:44:

```
Val His Val Tyr Trp Gln Pro Tyr Ser Val Gln Thr
 1               5                  10
```

(2) INFORMATION FOR SEQ ID NO:45:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:45:

```
Arg Leu Val Tyr Trp Gln Pro Tyr Ser Val Gln Thr
 1               5                  10
```

(2) INFORMATION FOR SEQ ID NO:46:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:46:

```
Ser Arg Val Trp Phe Gln Pro Tyr Ser Leu Gln Ser
 1               5                  10
```

(2) INFORMATION FOR SEQ ID NO:47:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:47:

```
Asn Met Val Tyr Trp Gln Pro Tyr Ser Ile Gln Thr
```

```
              1               5                    10
```

( 2 ) INFORMATION FOR SEQ ID NO:48:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:48:

```
Ser  Val  Val  Phe  Trp  Gln  Pro  Tyr  Ser  Val  Gln  Thr
1                  5                            10
```

( 2 ) INFORMATION FOR SEQ ID NO:49:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:49:

```
Thr  Phe  Val  Tyr  Trp  Gln  Pro  Tyr  Ala  Leu  Pro  Leu
1                  5                            10
```

( 2 ) INFORMATION FOR SEQ ID NO:50:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:50:

```
Thr  Leu  Val  Tyr  Trp  Gln  Pro  Tyr  Ser  Ile  Gln  Arg
1                  5                            10
```

( 2 ) INFORMATION FOR SEQ ID NO:51:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:51:

```
Ser  Pro  Val  Phe  Trp  Gln  Pro  Tyr  Ser  Ile  Gln  Ile
1                  5                            10
```

( 2 ) INFORMATION FOR SEQ ID NO:52:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:52:

```
Trp  Ile  Glu  Trp  Trp  Gln  Pro  Tyr  Ser  Val  Gln  Ser
```

(2) INFORMATION FOR SEQ ID NO:53:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:53:

```
Ser Leu Ile Tyr Trp Gln Pro Tyr Ser Leu Gln Met
 1               5                   10
```

(2) INFORMATION FOR SEQ ID NO:54:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:54:

```
Thr Arg Leu Tyr Trp Gln Pro Tyr Ser Val Gln Arg
 1               5                   10
```

(2) INFORMATION FOR SEQ ID NO:55:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:55:

```
Arg Cys Asp Tyr Trp Gln Pro Tyr Ser Val Gln Thr
 1               5                   10
```

(2) INFORMATION FOR SEQ ID NO:56:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:56:

```
Met Arg Val Phe Trp Gln Pro Tyr Ser Val Gln Asn
 1               5                   10
```

(2) INFORMATION FOR SEQ ID NO:57:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:57:

```
Lys Ile Val Tyr Trp Gln Pro Tyr Ser Val Gln Thr
```

( 2 ) INFORMATION FOR SEQ ID NO:58:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:58:

```
Arg His Leu Tyr Trp Gln Pro Tyr Ser Val Gln Arg
1               5                   10
```

( 2 ) INFORMATION FOR SEQ ID NO:59:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:59:

```
Ala Leu Val Trp Trp Gln Pro Tyr Ser Glu Gln Ile
1               5                   10
```

( 2 ) INFORMATION FOR SEQ ID NO:60:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:60:

```
Ser Arg Val Trp Phe Gln Pro Tyr Ser Leu Gln Ser
1               5                   10
```

( 2 ) INFORMATION FOR SEQ ID NO:61:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:61:

```
Trp Glu Gln Pro Tyr Ala Leu Pro Leu Glu
1               5                   10
```

( 2 ) INFORMATION FOR SEQ ID NO:62:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:62:

```
Arg Glu Tyr Glu Gln Pro Tyr Ala Leu Trp
```

(2) INFORMATION FOR SEQ ID NO:63:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:63:

```
Glu Glu Trp Ala Gln Pro Tyr Ala Phe Leu
1               5                   10
```

(2) INFORMATION FOR SEQ ID NO:64:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:64:

```
Gly Ser Trp Glu Gln Pro Tyr Ala Met Val
1               5                   10
```

(2) INFORMATION FOR SEQ ID NO:65:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:65:

```
Ala Trp Tyr Gly Pro Ser Asn Leu Pro Val
1               5                   10
```

(2) INFORMATION FOR SEQ ID NO:66:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:66:

```
Gln Leu Val Trp Trp Gln Pro Tyr Ser Val Gln Arg
1               5                   10
```

(2) INFORMATION FOR SEQ ID NO:67:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:67:

```
Asp Leu Arg Tyr Trp Gln Pro Tyr Ser Val Gln Val
```

( 2 ) INFORMATION FOR SEQ ID NO:68:

( i ) SEQUENCE CHARACTERISTICS:
     ( A ) LENGTH: 12 amino acids
     ( B ) TYPE: amino acid
     ( C ) STRANDEDNESS: single
     ( D ) TOPOLOGY: linear ( i i ) MOLECULE TYPE: peptide ( x i ) SEQUENCE DESCRIPTION: SEQ ID NO:68:

Glu Leu Val Trp Trp Gln Pro Tyr Ser Leu Gln Leu
1               5                   10

( 2 ) INFORMATION FOR SEQ ID NO:69:

( i ) SEQUENCE CHARACTERISTICS:
     ( A ) LENGTH: 12 amino acids
     ( B ) TYPE: amino acid
     ( C ) STRANDEDNESS: single
     ( D ) TOPOLOGY: linear ( i i ) MOLECULE TYPE: peptide ( x i ) SEQUENCE DESCRIPTION: SEQ ID NO:69:

Asp Leu Val Trp Trp Gln Pro Tyr Ser Val Gln Trp
1               5                   10

( 2 ) INFORMATION FOR SEQ ID NO:70:

( i ) SEQUENCE CHARACTERISTICS:
     ( A ) LENGTH: 12 amino acids
     ( B ) TYPE: amino acid
     ( C ) STRANDEDNESS: single
     ( D ) TOPOLOGY: linear ( i i ) MOLECULE TYPE: peptide ( x i ) SEQUENCE DESCRIPTION: SEQ ID NO:70:

Asn Gly Asn Tyr Trp Gln Pro Tyr Ser Phe Gln Val
1               5                   10

( 2 ) INFORMATION FOR SEQ ID NO:71:

( i ) SEQUENCE CHARACTERISTICS:
     ( A ) LENGTH: 12 amino acids
     ( B ) TYPE: amino acid
     ( C ) STRANDEDNESS: single
     ( D ) TOPOLOGY: linear ( i i ) MOLECULE TYPE: peptide ( x i ) SEQUENCE DESCRIPTION: SEQ ID NO:71:

Glu Leu Val Tyr Trp Gln Pro Tyr Ser Ile Gln Arg
1               5                   10

( 2 ) INFORMATION FOR SEQ ID NO:72:

( i ) SEQUENCE CHARACTERISTICS:
     ( A ) LENGTH: 12 amino acids
     ( B ) TYPE: amino acid
     ( C ) STRANDEDNESS: single
     ( D ) TOPOLOGY: linear ( i i ) MOLECULE TYPE: peptide ( x i ) SEQUENCE DESCRIPTION: SEQ ID NO:72:

Trp Ser Asn Tyr Trp Gln Pro Tyr Ser Val Gln Pro (2) INFORMATION FOR SEQ ID NO:73:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:73:

```
Gln Tyr Val Tyr Trp Gln Pro Leu Ser Val Gln Val
 1               5                   10
```

(2) INFORMATION FOR SEQ ID NO:74:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:74:

```
Glu Leu Met Tyr Trp Gln Pro Tyr Ser Val Gln Glu
 1               5                   10
```

(2) INFORMATION FOR SEQ ID NO:75:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:75:

```
Asn Leu Leu Tyr Trp Gln Pro Tyr Ser Met Gln Asp
 1               5                   10
```

(2) INFORMATION FOR SEQ ID NO:76:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:76:

```
Gly Tyr Glu Trp Tyr Gln Pro Tyr Ser Val Gln Arg
 1               5                   10
```

(2) INFORMATION FOR SEQ ID NO:77:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:77:

```
Ser Arg Val Trp Tyr Gln Pro Tyr Ser Val Gln Arg
```

(2) INFORMATION FOR SEQ ID NO:78:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:78:

Leu Ser Glu Gln Tyr Gln Pro Tyr Ser Val Gln Arg
    1                5                        10

(2) INFORMATION FOR SEQ ID NO:79:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:79:

Gly Gly Gly Trp Trp Gln Pro Tyr Ser Val Gln Arg
    1                5                        10

(2) INFORMATION FOR SEQ ID NO:80:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:80:

Val Gly Arg Trp Tyr Gln Pro Tyr Ser Val Gln Arg
    1                5                        10

(2) INFORMATION FOR SEQ ID NO:81:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:81:

Val His Val Tyr Trp Gln Pro Tyr Ser Val Gln Arg
    1                5                        10

(2) INFORMATION FOR SEQ ID NO:82:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:82:

Gln Ala Arg Trp Tyr Gln Pro Tyr Ser Val Gln Arg (2) INFORMATION FOR SEQ ID NO:83:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:83:

```
Val His Val Tyr Trp Gln Pro Tyr Ser Val Gln Thr
 1               5                   10
```

(2) INFORMATION FOR SEQ ID NO:84:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:84:

```
Arg Ser Val Tyr Trp Gln Pro Tyr Ser Val Gln Arg
 1               5                   10
```

(2) INFORMATION FOR SEQ ID NO:85:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:85:

```
Thr Arg Val Trp Phe Gln Pro Tyr Ser Val Gln Arg
 1               5                   10
```

(2) INFORMATION FOR SEQ ID NO:86:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:86:

```
Gly Arg Ile Trp Phe Gln Pro Tyr Ser Val Gln Arg
 1               5                   10
```

(2) INFORMATION FOR SEQ ID NO:87:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:87:

```
Gly Arg Val Trp Phe Gln Pro Tyr Ser Val Gln Arg
```

( 2 ) INFORMATION FOR SEQ ID NO:88:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:88:

```
Ala  Arg  Thr  Trp  Tyr  Gln  Pro  Tyr  Ser  Val  Gln  Arg
1                 5                          10
```

( 2 ) INFORMATION FOR SEQ ID NO:89:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:89:

```
Gly  Arg  Leu  Trp  Trp  Gln  Pro  Tyr  Ser  Val  Gln  Arg
1                 5                          10
```

( 2 ) INFORMATION FOR SEQ ID NO:90:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:90:

```
His  Arg  Ile  Trp  Trp  Gln  Pro  Tyr  Ser  Val  Gln  Arg
1                 5                          10
```

( 2 ) INFORMATION FOR SEQ ID NO:91:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:91:

```
Gly  Arg  Val  Trp  Trp  Gln  Pro  Tyr  Ser  Val  Gln  Arg
1                 5                          10
```

( 2 ) INFORMATION FOR SEQ ID NO:92:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:92:

```
Ala  Arg  Val  Trp  Trp  Gln  Pro  Tyr  Ser  Val  Gln  Met
```

( 2 ) INFORMATION FOR SEQ ID NO:93:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:93:

```
Arg  Leu  Met  Phe  Tyr  Gln  Pro  Tyr  Ser  Val  Gln  Arg
 1              5                             10
```

( 2 ) INFORMATION FOR SEQ ID NO:94:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:94:

```
Glu  Ser  Met  Trp  Tyr  Gln  Pro  Tyr  Ser  Val  Gln  Arg
 1              5                             10
```

( 2 ) INFORMATION FOR SEQ ID NO:95:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:95:

```
His  Phe  Gly  Trp  Trp  Gln  Pro  Tyr  Ser  Val  His  Met
 1              5                             10
```

( 2 ) INFORMATION FOR SEQ ID NO:96:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:96:

```
Ala  Arg  Phe  Trp  Trp  Gln  Pro  Tyr  Ser  Val  Gln  Arg
 1              5                             10
```

( 2 ) INFORMATION FOR SEQ ID NO:97:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:97:

```
Arg  Leu  Val  Tyr  Trp  Gln  Pro  Tyr  Ala  Pro  Ile  Tyr
```

```
        1               5               1 0
```

(2) INFORMATION FOR SEQ ID NO:98:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:98:

```
Arg Leu Val Tyr Trp Gln Pro Tyr Ser Tyr Gln Thr
 1               5                   1 0
```

(2) INFORMATION FOR SEQ ID NO:99:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:99:

```
Arg Leu Val Tyr Trp Gln Pro Tyr Ser Leu Pro Ile
 1               5                   1 0
```

(2) INFORMATION FOR SEQ ID NO:100:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:100:

```
Arg Leu Val Tyr Trp Gln Pro Tyr Ser Val Gln Ala
 1               5                   1 0
```

(2) INFORMATION FOR SEQ ID NO:101:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:101:

```
Arg Leu Val Tyr Trp Gln Pro Trp Ala Pro Ile Trp
 1               5                   1 0
```

(2) INFORMATION FOR SEQ ID NO:102:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:102:

```
Ser Arg Val Trp Tyr Gln Pro Tyr Ala Lys Gly Leu
```

(2) INFORMATION FOR SEQ ID NO:103:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:103:

Ser Arg Val Trp Tyr Gln Pro Tyr Ala Gln Gly Leu
1               5                   10

(2) INFORMATION FOR SEQ ID NO:104:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:104:

Ser Arg Val Trp Tyr Gln Pro Tyr Ala Met Pro Leu
1               5                   10

(2) INFORMATION FOR SEQ ID NO:105:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:105:

Ser Arg Val Trp Tyr Gln Pro Tyr Ser Val Gln Ala
1               5                   10

(2) INFORMATION FOR SEQ ID NO:106:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:106:

Ser Arg Val Trp Tyr Gln Pro Tyr Ser Leu Gly Leu
1               5                   10

(2) INFORMATION FOR SEQ ID NO:107:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:107:

Ser Arg Val Trp Tyr Gln Pro Tyr Ala Arg Glu Leu ( 2 ) INFORMATION FOR SEQ ID NO:108:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:108:

```
Ser  Arg  Val  Trp  Tyr  Gln  Pro  Tyr  Ser  Arg  Gln  Pro
1                 5                           10
```

( 2 ) INFORMATION FOR SEQ ID NO:109:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:109:

```
Ser  Arg  Val  Trp  Tyr  Gln  Pro  Tyr  Phe  Val  Gln  Pro
1                 5                           10
```

( 2 ) INFORMATION FOR SEQ ID NO:110:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:110:

```
Glu  Tyr  Glu  Trp  Gln  Tyr  Pro  Tyr  Ala  Leu  Pro  Leu
1                 5                           10
```

( 2 ) INFORMATION FOR SEQ ID NO:111:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:111:

```
Ile  Pro  Glu  Tyr  Trp  Gln  Pro  Tyr  Ala  Leu  Pro  Leu
1                 5                           10
```

( 2 ) INFORMATION FOR SEQ ID NO:112:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:112:

```
Ser  Arg  Ile  Trp  Trp  Gln  Pro  Tyr  Ala  Leu  Pro  Leu
```

(2) INFORMATION FOR SEQ ID NO:113:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:113:

Asp Pro Leu Phe Trp Gln Pro Tyr Ala Leu Pro Leu
  1               5                   10

(2) INFORMATION FOR SEQ ID NO:114:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:114:

Ser Arg Gln Trp Val Gln Pro Tyr Ala Leu Pro Leu
  1               5                   10

(2) INFORMATION FOR SEQ ID NO:115:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:115:

Ile Arg Ser Trp Trp Gln Pro Tyr Ala Leu Pro Leu
  1               5                   10

(2) INFORMATION FOR SEQ ID NO:116:

(i) SEQUENCE CHARACTERISTICS:
    (A) LENGTH: 11 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:116:

Arg Gly Tyr Trp Gln Pro Tyr Ala Leu Pro Leu
  1               5                   10

(2) INFORMATION FOR SEQ ID NO:117:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:117:

Arg Leu Leu Trp Val Gln Pro Tyr Ala Leu Pro Leu (2) INFORMATION FOR SEQ ID NO:118:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:118:

```
Glu Tyr Arg Trp Phe Gln Pro Tyr Ala Leu Pro Leu
 1               5                  10
```

(2) INFORMATION FOR SEQ ID NO:119:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:119:

```
Asp Ala Tyr Trp Val Gln Pro Tyr Ala Leu Pro Leu
 1               5                  10
```

(2) INFORMATION FOR SEQ ID NO:120:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:120:

```
Trp Ser Gly Tyr Phe Gln Pro Tyr Ala Leu Pro Leu
 1               5                  10
```

(2) INFORMATION FOR SEQ ID NO:121:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:121:

```
Asn Ile Glu Phe Trp Gln Pro Tyr Ala Leu Pro Leu
 1               5                  10
```

(2) INFORMATION FOR SEQ ID NO:122:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:122:

```
Thr Arg Asp Trp Val Gln Pro Tyr Ala Leu Pro Leu
```

(2) INFORMATION FOR SEQ ID NO:123:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:123:

```
Asp Ser Ser Trp Tyr Gln Pro Tyr Ala Leu Pro Leu
 1               5                   10
```

(2) INFORMATION FOR SEQ ID NO:124:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:124:

```
Ile Gly Asn Trp Tyr Gln Pro Tyr Ala Leu Pro Leu
 1               5                   10
```

(2) INFORMATION FOR SEQ ID NO:125:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:125:

```
Asn Leu Arg Trp Asp Gln Pro Tyr Ala Leu Pro Leu
 1               5                   10
```

(2) INFORMATION FOR SEQ ID NO:126:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:126:

```
Leu Pro Glu Phe Trp Gln Pro Tyr Ala Leu Pro Leu
 1               5                   10
```

(2) INFORMATION FOR SEQ ID NO:127:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:127:

```
Asp Ser Tyr Trp Trp Gln Pro Tyr Ala Leu Pro Leu
```

( 2 ) INFORMATION FOR SEQ ID NO:128:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:128:

```
Arg Ser Gln Tyr Tyr Gln Pro Tyr Ala Leu Pro Leu
1               5                   10
```

( 2 ) INFORMATION FOR SEQ ID NO:129:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:129:

```
Ala Arg Phe Trp Leu Gln Pro Tyr Ala Leu Pro Leu
1               5                   10
```

( 2 ) INFORMATION FOR SEQ ID NO:130:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:130:

```
Asn Ser Tyr Phe Trp Gln Pro Tyr Ala Leu Pro Leu
1               5                   10
```

( 2 ) INFORMATION FOR SEQ ID NO:131:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:131:

```
Glu Ser Phe Trp Val Gln Pro Tyr Ala Leu Pro Leu
1               5                   10
```

( 2 ) INFORMATION FOR SEQ ID NO:132:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:132:

```
Arg Phe Met Tyr Trp Gln Pro Tyr Ser Val Gln Arg
```

(2) INFORMATION FOR SEQ ID NO:133:

(i) SEQUENCE CHARACTERISTICS:
  (A) LENGTH: 12 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:133:

```
Ala His Leu Phe Trp Gln Pro Tyr Ser Val Gln Arg
 1               5                   10
```

(2) INFORMATION FOR SEQ ID NO:134:

(i) SEQUENCE CHARACTERISTICS:
  (A) LENGTH: 12 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:134:

```
Trp Gly Asn Trp Trp Gln Pro Tyr Ser Val His Arg
 1               5                   10
```

(2) INFORMATION FOR SEQ ID NO:135:

(i) SEQUENCE CHARACTERISTICS:
  (A) LENGTH: 9 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:135:

```
Trp Trp Gln Pro Tyr Ala Leu Pro Leu
 1               5
```

(2) INFORMATION FOR SEQ ID NO:136:

(i) SEQUENCE CHARACTERISTICS:
  (A) LENGTH: 9 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:136:

```
Tyr Tyr Gln Pro Tyr Ala Leu Pro Leu
 1               5
```

(2) INFORMATION FOR SEQ ID NO:137:

(i) SEQUENCE CHARACTERISTICS:
  (A) LENGTH: 9 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:137:

```
Tyr Phe Gln Pro Tyr Ala Leu Gly Leu
```

(2) INFORMATION FOR SEQ ID NO:138:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:138:

```
Tyr Phe Gln Pro Tyr Ala Leu Pro Phe
1               5
```

(2) INFORMATION FOR SEQ ID NO:139:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:139:

```
Val Trp Tyr Gln Pro Tyr Ala Leu Pro Leu
1               5                   10
```

(2) INFORMATION FOR SEQ ID NO:140:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:140:

```
Arg Trp Trp Gln Pro Tyr Ala Thr Pro Leu
1               5                   10
```

(2) INFORMATION FOR SEQ ID NO:141:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:141:

```
Gly Trp Tyr Gln Pro Tyr Ala Leu Gly Phe
1               5                   10
```

(2) INFORMATION FOR SEQ ID NO:142:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:142:

```
Tyr Trp Tyr Gln Pro Tyr Ala Leu Gly Leu
```

-continued ( 2 ) INFORMATION FOR SEQ ID NO:143:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:143:

Ile Trp Tyr Gln Pro Tyr Ala Met Pro Leu
   1               5                   10

( 2 ) INFORMATION FOR SEQ ID NO:144:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:144:

Ser Asn Met Gln Pro Tyr Gln Arg Leu Ser
   1               5                   10

( 2 ) INFORMATION FOR SEQ ID NO:145:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:145:

Thr Phe Val Tyr Trp Gln Pro Tyr Ala Val Gly Leu Phe Ala Ala Glu
   1               5                   10                  15

Thr Ala Cys Asn
                  20

( 2 ) INFORMATION FOR SEQ ID NO:146:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:146:

Thr Phe Val Tyr Trp Gln Pro Tyr Ser Val Gln Met Thr Ile Thr Gly
   1               5                   10                  15

Lys Val Thr Met
                  20

( 2 ) INFORMATION FOR SEQ ID NO:147:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:147:

Thr Phe Val Tyr Trp Gln Pro Tyr Ser Ser His Xaa Xaa Val Pro Xaa
1               5                   10                  15
Gly Phe Pro Leu
            20

( 2 ) INFORMATION FOR SEQ ID NO:148:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:148:

Thr Phe Val Tyr Trp Gln Pro Tyr Tyr Gly Asn Pro Gln Trp Ala Ile
1               5                   10                  15
His Val Arg His
            20

( 2 ) INFORMATION FOR SEQ ID NO:149:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:149:

Thr Phe Val Tyr Trp Gln Pro Tyr Val Leu Leu Glu Leu Pro Glu Gly
1               5                   10                  15
Ala Val Arg Ala
            20

( 2 ) INFORMATION FOR SEQ ID NO:150:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:150:

Thr Phe Val Tyr Trp Gln Pro Tyr Val Asp Tyr Val Trp Pro Ile Pro
1               5                   10                  15
Ile Ala Gln Val
            20

( 2 ) INFORMATION FOR SEQ ID NO:151:

( i ) SEQUENCE CHARACTERISTICS:
      ( A ) LENGTH: 14 amino acids
      ( B ) TYPE: amino acid
      ( C ) STRANDEDNESS: single
      ( D ) TOPOLOGY: linear ( i i ) MOLECULE TYPE: peptide ( i x ) FEATURE:

(A) NAME/KEY: Region
(B) LOCATION: one-of (7,8)
(D) OTHER INFORMATION: /note="Xaa is Pro or Gly."

(xi) SEQUENCE DESCRIPTION: SEQ ID NO:151:

Xaa Xaa Xaa Xaa Xaa Xaa Xaa Xaa Xaa Xaa Xaa Xaa Xaa Xaa
1               5                   10

(2) INFORMATION FOR SEQ ID NO:152:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:152:

Ile Met Trp Phe Cys Gln Pro Gly Gly Ala Cys Tyr Ser Val
1               5                   10

(2) INFORMATION FOR SEQ ID NO:153:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:153:

Gly Trp Tyr Gln Pro Tyr Val Asp Gly Trp Arg
1               5                   10

(2) INFORMATION FOR SEQ ID NO:154:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:154:

Arg Trp Glu Gln Pro Tyr Val Lys Asp Gly Trp Ser
1               5                   10

(2) INFORMATION FOR SEQ ID NO:155:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:155:

Glu Trp Tyr Gln Pro Tyr Ala Leu Gly Trp Ala Arg
1               5                   10

(2) INFORMATION FOR SEQ ID NO:156:

(i) SEQUENCE CHARACTERISTICS:
        (A) LENGTH: 10 amino acids
        (B) TYPE: amino acid
        (C) STRANDEDNESS: single ( D ) TOPOLOGY: linear ( i i ) MOLECULE TYPE: peptide ( x i ) SEQUENCE DESCRIPTION: SEQ ID NO:156:

```
Gly Trp Trp Gln Pro Tyr Ala Arg Gly Leu
1               5                   10
```

( 2 ) INFORMATION FOR SEQ ID NO:157:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:157:

```
Leu Phe Glu Gln Pro Tyr Ala Lys Ala Leu Gly Leu
1               5                   10
```

( 2 ) INFORMATION FOR SEQ ID NO:158:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:158:

```
Gly Trp Glu Gln Pro Tyr Ala Arg Gly Leu Ala Gly
1               5                   10
```

( 2 ) INFORMATION FOR SEQ ID NO:159:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:159:

```
Ala Trp Val Gln Pro Tyr Ala Thr Pro Leu Asp Glu
1               5                   10
```

( 2 ) INFORMATION FOR SEQ ID NO:160:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:160:

```
Met Trp Tyr Gln Pro Tyr Ser Ser Gln Pro Ala Glu
1               5                   10
```

( 2 ) INFORMATION FOR SEQ ID NO:161:

( i ) SEQUENCE CHARACTERISTICS:
        ( A ) LENGTH: 12 amino acids
        ( B ) TYPE: amino acid
        ( C ) STRANDEDNESS: single ( D ) TOPOLOGY: linear ( i i ) MOLECULE TYPE: peptide ( x i ) SEQUENCE DESCRIPTION: SEQ ID NO:161:

Gly Trp Thr Gln Pro Tyr Ser Gln Gln Gly Glu Val
1               5                   10

( 2 ) INFORMATION FOR SEQ ID NO:162:

( i ) SEQUENCE CHARACTERISTICS:
  ( A ) LENGTH: 12 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:162:

Asp Trp Phe Gln Pro Tyr Ser Ile Gln Ser Asp Glu
1               5                   10

( 2 ) INFORMATION FOR SEQ ID NO:163:

( i ) SEQUENCE CHARACTERISTICS:
  ( A ) LENGTH: 11 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:163:

Pro Trp Ile Gln Pro Tyr Ala Arg Gly Phe Gly
1               5                   10

( 2 ) INFORMATION FOR SEQ ID NO:164:

( i ) SEQUENCE CHARACTERISTICS:
  ( A ) LENGTH: 12 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:164:

Arg Pro Leu Tyr Trp Gln Pro Tyr Ser Val Gln Val
1               5                   10

( 2 ) INFORMATION FOR SEQ ID NO:165:

( i ) SEQUENCE CHARACTERISTICS:
  ( A ) LENGTH: 12 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:165:

Thr Leu Ile Tyr Trp Gln Pro Tyr Ser Val Gln Ile
1               5                   10

( 2 ) INFORMATION FOR SEQ ID NO:166:

( i ) SEQUENCE CHARACTERISTICS:
  ( A ) LENGTH: 12 amino acids
  ( B ) TYPE: amino acid
  ( C ) STRANDEDNESS: single (D) TOPOLOGY: linear (ii) MOLECULE TYPE: peptide (xi) SEQUENCE DESCRIPTION: SEQ ID NO:166:

Arg Phe Asp Tyr Trp Gln Pro Tyr Ser Asp Gln Thr
1               5                   10

(2) INFORMATION FOR SEQ ID NO:167:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:167:

Trp His Gln Phe Val Gln Pro Tyr Ala Leu Pro Leu
1               5                   10

(2) INFORMATION FOR SEQ ID NO:168:

(i) SEQUENCE CHARACTERISTICS:
    (A) LENGTH: 17 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:168:

Glu Trp Asp Ser Val Tyr Trp Gln Pro Tyr Ser Val Gln Thr Leu Leu
1               5                   10                  15

Arg (2) INFORMATION FOR SEQ ID NO:169:

(i) SEQUENCE CHARACTERISTICS:
    (A) LENGTH: 17 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:169:

Trp Glu Gln Asn Val Tyr Trp Gln Pro Tyr Ser Val Gln Ser Phe Ala
1               5                   10                  15

Asp (2) INFORMATION FOR SEQ ID NO:170:

(i) SEQUENCE CHARACTERISTICS:
    (A) LENGTH: 16 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:170:

Ser Asp Val Val Tyr Trp Gln Pro Tyr Ser Val Gln Ser Leu Glu Met
1               5                   10                  15

(2) INFORMATION FOR SEQ ID NO:171:

( i ) SEQUENCE CHARACTERISTICS:
   ( A ) LENGTH: 17 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:171:

Tyr Tyr Asp Gly Val Tyr Trp Gln Pro Tyr Ser Val Gln Val Met Pro
1               5                   10                  15
Ala ( 2 ) INFORMATION FOR SEQ ID NO:172:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:172:

Ser Asp Ile Trp Tyr Gln Pro Tyr Ala Leu Pro Leu
1               5                   10

( 2 ) INFORMATION FOR SEQ ID NO:173:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:173:

Gln Arg Ile Trp Trp Gln Pro Tyr Ala Leu Pro Leu
1               5                   10

( 2 ) INFORMATION FOR SEQ ID NO:174:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:174:

Ser Arg Ile Trp Trp Gln Pro Tyr Ala Leu Pro Leu
1               5                   10

( 2 ) INFORMATION FOR SEQ ID NO:175:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:175:

Arg Ser Leu Tyr Trp Gln Pro Tyr Ala Leu Pro Leu
1               5                   10

( 2 ) INFORMATION FOR SEQ ID NO:176:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:176:

```
Thr Ile Ile Trp Glu Gln Pro Tyr Ala Leu Pro Leu
1               5                   10
```

( 2 ) INFORMATION FOR SEQ ID NO:177:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:177:

```
Trp Glu Thr Trp Tyr Gln Pro Tyr Ala Leu Pro Leu
1               5                   10
```

( 2 ) INFORMATION FOR SEQ ID NO:178:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:178:

```
Ser Tyr Asp Trp Glu Gln Pro Tyr Ala Leu Pro Leu
1               5                   10
```

( 2 ) INFORMATION FOR SEQ ID NO:179:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:179:

```
Ser Arg Ile Trp Cys Gln Pro Tyr Ala Leu Pro Leu
1               5                   10
```

( 2 ) INFORMATION FOR SEQ ID NO:180:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:180:

```
Glu Ile Met Phe Trp Gln Pro Tyr Ala Leu Pro Leu
1               5                   10
```

( 2 ) INFORMATION FOR SEQ ID NO:181:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:181:

```
Asp Tyr Val Trp Gln Gln Pro Tyr Ala Leu Pro Leu
 1               5                   10
```

( 2 ) INFORMATION FOR SEQ ID NO:182:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:182:

```
Met Asp Leu Leu Val Gln Trp Tyr Gln Pro Tyr Ala Leu Pro Leu
 1               5                   10                  15
```

( 2 ) INFORMATION FOR SEQ ID NO:183:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:183:

```
Gly Ser Lys Val Ile Leu Trp Tyr Gln Pro Tyr Ala Leu Pro Leu
 1               5                   10                  15
```

( 2 ) INFORMATION FOR SEQ ID NO:184:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:184:

```
Arg Gln Gly Ala Asn Ile Trp Tyr Gln Pro Tyr Ala Leu Pro Leu
 1               5                   10                  15
```

( 2 ) INFORMATION FOR SEQ ID NO:185:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:185:

```
Gly Gly Gly Asp Glu Pro Trp Tyr Gln Pro Tyr Ala Leu Pro Leu
 1               5                   10                  15
```

( 2 ) INFORMATION FOR SEQ ID NO:186:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:186:

```
Ser Gln Leu Glu Arg Thr Trp Tyr Gln Pro Tyr Ala Leu Pro Leu
1               5                   10                  15
```

( 2 ) INFORMATION FOR SEQ ID NO:187:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:187:

```
Glu Thr Trp Val Arg Glu Trp Tyr Gln Pro Tyr Ala Leu Pro Leu
1               5                   10                  15
```

( 2 ) INFORMATION FOR SEQ ID NO:188:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:188:

```
Lys Lys Gly Ser Thr Gln Trp Tyr Gln Pro Tyr Ala Leu Pro Leu
1               5                   10                  15
```

( 2 ) INFORMATION FOR SEQ ID NO:189:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:189:

```
Leu Gln Ala Arg Met Asn Trp Tyr Gln Pro Tyr Ala Leu Pro Leu
1               5                   10                  15
```

( 2 ) INFORMATION FOR SEQ ID NO:190:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:190:

```
Glu Pro Arg Ser Gln Lys Trp Tyr Gln Pro Tyr Ala Leu Pro Leu
1               5                   10                  15
```

( 2 ) INFORMATION FOR SEQ ID NO:191:

( i ) SEQUENCE CHARACTERISTICS:
  ( A ) LENGTH: 15 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:191:

```
Val Lys Gln Lys Trp Arg Trp Tyr Gln Pro Tyr Ala Leu Pro Leu
1               5                   10                  15
```

( 2 ) INFORMATION FOR SEQ ID NO:192:

( i ) SEQUENCE CHARACTERISTICS:
  ( A ) LENGTH: 15 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:192:

```
Leu Arg Arg His Asp Tyr Trp Tyr Gln Pro Tyr Ala Leu Pro Leu
1               5                   10                  15
```

( 2 ) INFORMATION FOR SEQ ID NO:193:

( i ) SEQUENCE CHARACTERISTICS:
  ( A ) LENGTH: 15 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:193:

```
Arg Ser Thr Ala Ser Ile Trp Tyr Gln Pro Tyr Ala Leu Pro Leu
1               5                   10                  15
```

( 2 ) INFORMATION FOR SEQ ID NO:194:

( i ) SEQUENCE CHARACTERISTICS:
  ( A ) LENGTH: 15 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:194:

```
Glu Ser Lys Glu Asp Gln Trp Tyr Gln Pro Tyr Ala Leu Pro Leu
1               5                   10                  15
```

( 2 ) INFORMATION FOR SEQ ID NO:195:

( i ) SEQUENCE CHARACTERISTICS:
  ( A ) LENGTH: 15 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:195:

```
Glu Gly Leu Thr Met Lys Trp Tyr Gln Pro Tyr Ala Leu Pro Leu
1               5                   10                  15
```

( 2 ) INFORMATION FOR SEQ ID NO:196:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:196:

```
Glu Gly Ser Arg Glu Gly Trp Tyr Gln Pro Tyr Ala Leu Pro Leu
  1               5                  10                  15
```

( 2 ) INFORMATION FOR SEQ ID NO:197:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:197:

```
Val Ile Glu Trp Trp Gln Pro Tyr Ala Leu Pro Leu
  1               5                  10
```

( 2 ) INFORMATION FOR SEQ ID NO:198:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:198:

```
Val Trp Tyr Trp Glu Gln Pro Tyr Ala Leu Pro Leu
  1               5                  10
```

( 2 ) INFORMATION FOR SEQ ID NO:199:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:199:

```
Ala Ser Glu Trp Trp Gln Pro Tyr Ala Leu Pro Leu
  1               5                  10
```

( 2 ) INFORMATION FOR SEQ ID NO:200:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:200:

```
Phe Tyr Glu Trp Trp Gln Pro Tyr Ala Leu Pro Leu
  1               5                  10
```

( 2 ) INFORMATION FOR SEQ ID NO:201:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:201:

```
Glu  Gly  Trp  Trp  Val  Gln  Pro  Tyr  Ala  Leu  Pro  Leu
1                   5                        10
```

( 2 ) INFORMATION FOR SEQ ID NO:202:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:202:

```
Trp  Gly  Glu  Trp  Leu  Gln  Pro  Tyr  Ala  Leu  Pro  Leu
1                   5                        10
```

( 2 ) INFORMATION FOR SEQ ID NO:203:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:203:

```
Asp  Tyr  Val  Trp  Glu  Gln  Pro  Tyr  Ala  Leu  Pro  Leu
1                   5                        10
```

( 2 ) INFORMATION FOR SEQ ID NO:204:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:204:

```
Ala  His  Thr  Trp  Trp  Gln  Pro  Tyr  Ala  Leu  Pro  Leu
1                   5                        10
```

( 2 ) INFORMATION FOR SEQ ID NO:205:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:205:

```
Phe  Ile  Glu  Trp  Phe  Gln  Pro  Tyr  Ala  Leu  Pro  Leu
1                   5                        10
```

( 2 ) INFORMATION FOR SEQ ID NO:206:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:206:

```
Trp  Leu  Ala  Trp  Glu  Gln  Pro  Tyr  Ala  Leu  Pro  Leu
 1              5                             10
```

( 2 ) INFORMATION FOR SEQ ID NO:207:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:207:

```
Val  Met  Glu  Trp  Trp  Gln  Pro  Tyr  Ala  Leu  Pro  Leu
 1              5                             10
```

( 2 ) INFORMATION FOR SEQ ID NO:208:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:208:

```
Glu  Arg  Met  Trp  Gln  Pro  Tyr  Ala  Leu  Pro  Leu
 1              5                        10
```

( 2 ) INFORMATION FOR SEQ ID NO:209:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:209:

```
Asp  Xaa  Xaa  Trp  Xaa  Xaa  Pro  Tyr  Ala  Leu  Pro  Leu
 1              5                             10
```

( 2 ) INFORMATION FOR SEQ ID NO:210:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:210:

```
Trp  Gly  Asn  Trp  Tyr  Gln  Pro  Tyr  Ala  Leu  Pro  Leu
 1              5                             10
```

( 2 ) INFORMATION FOR SEQ ID NO:211:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:211:

```
Thr  Leu  Tyr  Trp  Glu  Gln  Pro  Tyr  Ala  Leu  Pro  Leu
1                  5                        10
```

( 2 ) INFORMATION FOR SEQ ID NO:212:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:212:

```
Val  Trp  Arg  Trp  Glu  Gln  Pro  Tyr  Ala  Leu  Pro  Leu
1                  5                        10
```

( 2 ) INFORMATION FOR SEQ ID NO:213:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:213:

```
Leu  Leu  Trp  Thr  Gln  Pro  Tyr  Ala  Leu  Pro  Leu
1                  5                   10
```

( 2 ) INFORMATION FOR SEQ ID NO:214:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:214:

```
Ser  Arg  Ile  Trp  Xaa  Xaa  Pro  Tyr  Ala  Leu  Pro  Leu
1                  5                        10
```

( 2 ) INFORMATION FOR SEQ ID NO:215:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:215:

```
Trp  Gly  Tyr  Tyr  Xaa  Xaa  Pro  Tyr  Ala  Leu  Pro  Leu
1                  5                        10
```

( 2 ) INFORMATION FOR SEQ ID NO:216:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:216:

Thr Ser Gly Trp Tyr Gln Pro Tyr Ala Leu Pro Leu
1               5                   10

( 2 ) INFORMATION FOR SEQ ID NO:217:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:217:

Val His Pro Tyr Xaa Xaa Pro Tyr Ala Leu Pro Leu
1               5                   10

( 2 ) INFORMATION FOR SEQ ID NO:218:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:218:

Glu His Ser Tyr Phe Gln Pro Tyr Ala Leu Pro Leu
1               5                   10

( 2 ) INFORMATION FOR SEQ ID NO:219:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:219:

Xaa Xaa Ile Trp Tyr Gln Pro Tyr Ala Leu Pro Leu
1               5                   10

( 2 ) INFORMATION FOR SEQ ID NO:220:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:220:

Ala Gln Leu His Ser Gln Pro Tyr Ala Leu Pro Leu
1               5                   10

( 2 ) INFORMATION FOR SEQ ID NO:221:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:221:

```
Trp Ala Asn Trp Phe Gln Pro Tyr Ala Leu Pro Leu
1               5                   10
```

( 2 ) INFORMATION FOR SEQ ID NO:222:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:222:

```
Ser Arg Leu Tyr Ser Gln Pro Tyr Ala Leu Pro Leu
1               5                   10
```

( 2 ) INFORMATION FOR SEQ ID NO:223:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:223:

```
Tyr Tyr Thr Trp Gln Gln Pro Tyr Ala Leu Pro Leu
1               5                   10
```

( 2 ) INFORMATION FOR SEQ ID NO:224:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:224:

```
Gly Val Thr Phe Ser Gln Pro Tyr Ala Leu Pro Leu
1               5                   10
```

( 2 ) INFORMATION FOR SEQ ID NO:225:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:225:

```
Gly Val Val Trp Tyr Gln Pro Tyr Ala Leu Pro Leu
1               5                   10
```

( 2 ) INFORMATION FOR SEQ ID NO:226:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:226:

```
Ser  Ile  Val  Trp  Ser  Gln  Pro  Tyr  Ala  Leu  Pro  Leu
1                   5                        10
```

( 2 ) INFORMATION FOR SEQ ID NO:227:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:227:

```
Tyr  Tyr  Ser  Trp  Gln  Pro  Tyr  Ala  Leu  Pro  Leu
1                   5                        10
```

( 2 ) INFORMATION FOR SEQ ID NO:228:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:228:

```
Ser  Arg  Asp  Leu  Val  Gln  Pro  Tyr  Ala  Leu  Pro  Leu
1                   5                        10
```

( 2 ) INFORMATION FOR SEQ ID NO:229:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:229:

```
His  Trp  Gly  His  Val  Tyr  Trp  Gln  Pro  Tyr  Ser  Val  Gln  Asp  Asp  Leu
1                   5                        10                       15

Gly
```

( 2 ) INFORMATION FOR SEQ ID NO:230:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:230:

```
Ser  Trp  His  Ser  Val  Tyr  Trp  Gln  Pro  Tyr  Ser  Val  Gln  Ser  Val  Pro
1                   5                        10                       15
```

Glu (2) INFORMATION FOR SEQ ID NO:231:

(i) SEQUENCE CHARACTERISTICS:
(A) LENGTH: 17 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:231:

Trp Arg Asp Ser Val Tyr Trp Gln Pro Tyr Ser Val Gln Pro Glu Ser
1               5                   10                  15
Ala (2) INFORMATION FOR SEQ ID NO:232:

(i) SEQUENCE CHARACTERISTICS:
(A) LENGTH: 17 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:232:

Thr Trp Asp Ala Val Tyr Trp Gln Pro Tyr Ser Val Gln Lys Trp Leu
1               5                   10                  15
Asp (2) INFORMATION FOR SEQ ID NO:233:

(i) SEQUENCE CHARACTERISTICS:
(A) LENGTH: 17 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:233:

Thr Pro Pro Trp Val Tyr Trp Gln Pro Tyr Ser Val Gln Ser Leu Asp
1               5                   10                  15
Pro (2) INFORMATION FOR SEQ ID NO:234:

(i) SEQUENCE CHARACTERISTICS:
(A) LENGTH: 17 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:234:

Tyr Trp Ser Ser Val Tyr Trp Gln Pro Tyr Ser Val Gln Ser Val His
1               5                   10                  15
Ser (2) INFORMATION FOR SEQ ID NO:235:

(i) SEQUENCE CHARACTERISTICS:
(A) LENGTH: 10 amino acids

```
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:235:

Tyr  Trp  Tyr  Gln  Pro  Tyr  Ala  Leu  Gly  Leu
    1                   5                        10
```

( 2 ) INFORMATION FOR SEQ ID NO:236:

```
    ( i ) SEQUENCE CHARACTERISTICS:
            ( A ) LENGTH: 10 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:236:

Tyr  Trp  Tyr  Gln  Pro  Tyr  Ala  Leu  Pro  Leu
    1                   5                        10
```

( 2 ) INFORMATION FOR SEQ ID NO:237:

```
    ( i ) SEQUENCE CHARACTERISTICS:
            ( A ) LENGTH: 10 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:237:

Glu  Trp  Ile  Gln  Pro  Tyr  Ala  Thr  Gly  Leu
    1                   5                        10
```

( 2 ) INFORMATION FOR SEQ ID NO:238:

```
    ( i ) SEQUENCE CHARACTERISTICS:
            ( A ) LENGTH: 10 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:238:

Asn  Trp  Glu  Gln  Pro  Tyr  Ala  Lys  Pro  Leu
    1                   5                        10
```

( 2 ) INFORMATION FOR SEQ ID NO:239:

```
    ( i ) SEQUENCE CHARACTERISTICS:
            ( A ) LENGTH: 10 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:239:

Ala  Phe  Tyr  Gln  Pro  Tyr  Ala  Leu  Pro  Leu
    1                   5                        10
```

( 2 ) INFORMATION FOR SEQ ID NO:240:

```
    ( i ) SEQUENCE CHARACTERISTICS:
            ( A ) LENGTH: 10 amino acids
```

(B) TYPE: amino acid
(C) STRANDEDNESS: single
(D) TOPOLOGY: linear (ii) MOLECULE TYPE: peptide (xi) SEQUENCE DESCRIPTION: SEQ ID NO:240:

Phe Leu Tyr Gln Pro Tyr Ala Leu Pro Leu
1               5                   10

(2) INFORMATION FOR SEQ ID NO:241:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:241:

Val Cys Lys Gln Pro Tyr Leu Glu Trp Cys
1               5                   10

(2) INFORMATION FOR SEQ ID NO:242:

(i) SEQUENCE CHARACTERISTICS:
    (A) LENGTH: 21 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:242:

Ser Val Gly Glu Asp His Asn Phe Trp Thr Ser Glu Tyr Trp Gln Pro
1               5                   10                  15

Tyr Ala Leu Pro Leu
                20

(2) INFORMATION FOR SEQ ID NO:243:

(i) SEQUENCE CHARACTERISTICS:
    (A) LENGTH: 21 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:243:

Met Asn Asp Gln Thr Ser Glu Val Ser Thr Phe Pro Tyr Trp Gln Pro
1               5                   10                  15

Tyr Ala Leu Pro Leu
                20

(2) INFORMATION FOR SEQ ID NO:244:

(i) SEQUENCE CHARACTERISTICS:
    (A) LENGTH: 21 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:244:

Ser Trp Ser Glu Ala Phe Glu Gln Pro Arg Asn Leu Tyr Trp Gln Pro
1               5                   10                  15

Tyr Ala Leu Pro Leu
20

( 2 ) INFORMATION FOR SEQ ID NO:245:

( i ) SEQUENCE CHARACTERISTICS:
    ( A ) LENGTH: 21 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:245:

Gln Tyr Ala Glu Pro Ser Ala Leu Asn Asp Trp Gly Tyr Trp Gln Pro
1               5                   10                  15

Tyr Ala Leu Pro Leu
20

( 2 ) INFORMATION FOR SEQ ID NO:246:

( i ) SEQUENCE CHARACTERISTICS:
    ( A ) LENGTH: 21 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:246:

Asn Gly Asp Trp Ala Thr Ala Asp Trp Ser Asn Tyr Tyr Trp Gln Pro
1               5                   10                  15

Tyr Ala Leu Pro Leu
20

( 2 ) INFORMATION FOR SEQ ID NO:247:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:247:

Thr His Asp Glu His Ile Tyr Trp Gln Pro Tyr Ala Leu Pro Leu
1               5                   10                  15

( 2 ) INFORMATION FOR SEQ ID NO:248:

( i ) SEQUENCE CHARACTERISTICS:
    ( A ) LENGTH: 21 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:248:

Met Leu Glu Lys Thr Tyr Thr Thr Trp Thr Pro Gly Tyr Trp Gln Pro
1               5                   10                  15

Tyr Ala Leu Pro Leu
20

( 2 ) INFORMATION FOR SEQ ID NO:249:

( i ) SEQUENCE CHARACTERISTICS:
  ( A ) LENGTH: 20 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:249:

Trp Ser Asp Pro Leu Thr Arg Asp Ala Asp Leu Tyr Trp Gln Pro Tyr
1               5                   10                  15

Ala Leu Pro Leu
            20

( 2 ) INFORMATION FOR SEQ ID NO:250:

( i ) SEQUENCE CHARACTERISTICS:
    ( A ) LENGTH: 21 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:250:

Ser Asp Ala Phe Thr Thr Gln Asp Ser Gln Ala Met Tyr Trp Gln Pro
1               5                   10                  15

Tyr Ala Leu Pro Leu
            20

( 2 ) INFORMATION FOR SEQ ID NO:251:

( i ) SEQUENCE CHARACTERISTICS:
    ( A ) LENGTH: 21 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:251:

Gly Asp Asp Ala Ala Trp Arg Thr Asp Ser Leu Thr Tyr Trp Gln Pro
1               5                   10                  15

Tyr Ala Leu Pro Leu
            20

( 2 ) INFORMATION FOR SEQ ID NO:252:

( i ) SEQUENCE CHARACTERISTICS:
    ( A ) LENGTH: 21 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:252:

Ala Ile Ile Arg Gln Leu Tyr Arg Trp Ser Glu Met Tyr Trp Gln Pro
1               5                   10                  15

Tyr Ala Leu Pro Leu
            20

( 2 ) INFORMATION FOR SEQ ID NO:253:

( i ) SEQUENCE CHARACTERISTICS:
    ( A ) LENGTH: 21 amino acids
    ( B ) TYPE: amino acid
    ( C ) STRANDEDNESS: single -continued (D) TOPOLOGY: linear (i i) MOLECULE TYPE: peptide (x i) SEQUENCE DESCRIPTION: SEQ ID NO:253:

Glu Asn Thr Tyr Ser Pro Asn Trp Ala Asp Ser Met Tyr Trp Gln Pro
1               5                   10                  15

Tyr Ala Leu Pro Leu
            20

(2) INFORMATION FOR SEQ ID NO:254:

(i) SEQUENCE CHARACTERISTICS:
    (A) LENGTH: 21 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:254:

Glu Thr Pro Phe Thr Trp Glu Glu Ser Asn Ala Tyr Tyr Trp Gln Pro
1               5                   10                  15

Tyr Ala Leu Pro Leu
            20

(2) INFORMATION FOR SEQ ID NO:255:

(i) SEQUENCE CHARACTERISTICS:
    (A) LENGTH: 21 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:255:

Asp Gly Tyr Asp Arg Trp Arg Gln Ser Gly Glu Arg Tyr Trp Gln Pro
1               5                   10                  15

Tyr Ala Leu Pro Leu
            20

(2) INFORMATION FOR SEQ ID NO:256:

(i) SEQUENCE CHARACTERISTICS:
    (A) LENGTH: 21 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:256:

Thr Ala Asn Val Ser Ser Phe Glu Trp Thr Pro Tyr Tyr Trp Gln Pro
1               5                   10                  15

Tyr Ala Leu Pro Leu
            20

(2) INFORMATION FOR SEQ ID NO:257:

(i) SEQUENCE CHARACTERISTICS:
    (A) LENGTH: 21 amino acids
    (B) TYPE: amino acid
    (C) STRANDEDNESS: single
    (D) TOPOLOGY: linear (i i) MOLECULE TYPE: peptide ( x i ) SEQUENCE DESCRIPTION: SEQ ID NO:257:

Gln Thr Pro Phe Thr Trp Glu Glu Ser Asn Ala Tyr Tyr Trp Gln Pro
1               5                   10                  15

Tyr Ala Leu Pro Leu
            20

( 2 ) INFORMATION FOR SEQ ID NO:258:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:258:

Glu Asn Pro Phe Thr Trp Gln Glu Ser Asn Ala Tyr Tyr Trp Gln Pro
1               5                   10                  15

Tyr Ala Leu Pro Leu
            20

( 2 ) INFORMATION FOR SEQ ID NO:259:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:259:

Val Thr Pro Phe Thr Trp Glu Asp Ser Asn Val Phe Tyr Trp Gln Pro
1               5                   10                  15

Tyr Ala Leu Pro Leu
            20

( 2 ) INFORMATION FOR SEQ ID NO:260:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:260:

Gln Ile Pro Phe Thr Trp Glu Gln Ser Asn Ala Tyr Tyr Trp Gln Pro
1               5                   10                  15

Tyr Ala Leu Pro Leu
            20

( 2 ) INFORMATION FOR SEQ ID NO:261:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:261:

Gln Ala Pro Leu Thr Trp Gln Glu Ser Ala Ala Tyr Tyr Trp Gln Pro
1               5                   10                  15

Tyr Ala Leu Pro Leu
                20

( 2 ) INFORMATION FOR SEQ ID NO:262:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:262:

Glu Pro Thr Phe Thr Trp Glu Glu Ser Lys Ala Thr Tyr Trp Gln Pro
1                 5                   10                  15

Tyr Ala Leu Pro Leu
                20

( 2 ) INFORMATION FOR SEQ ID NO:263:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:263:

Thr Thr Thr Leu Thr Trp Glu Glu Ser Asn Ala Tyr Tyr Trp Gln Pro
1                 5                   10                  15

Tyr Ala Leu Pro Leu
                20

( 2 ) INFORMATION FOR SEQ ID NO:264:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:264:

Glu Ser Pro Leu Thr Trp Glu Glu Ser Ser Ala Leu Tyr Trp Gln Pro
1                 5                   10                  15

Tyr Ala Leu Pro Leu
                20

( 2 ) INFORMATION FOR SEQ ID NO:265:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:265:

Glu Thr Pro Leu Thr Trp Glu Glu Ser Asn Ala Tyr Tyr Trp Gln Pro
1                 5                   10                  15

Tyr Ala Leu Pro Leu
                20

( 2 ) INFORMATION FOR SEQ ID NO:266:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:266:

```
Glu  Ala  Thr  Phe  Thr  Trp  Ala  Glu  Ser  Asn  Ala  Tyr  Tyr  Trp  Gln  Pro
1                   5                        10                       15
Tyr  Ala  Leu  Pro  Leu
                20
```

( 2 ) INFORMATION FOR SEQ ID NO:267:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:267:

```
Glu  Ala  Leu  Phe  Thr  Trp  Lys  Glu  Ser  Thr  Ala  Tyr  Tyr  Trp  Gln  Pro
1                   5                        10                       15
Tyr  Ala  Leu  Pro  Leu
                20
```

( 2 ) INFORMATION FOR SEQ ID NO:268:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:268:

```
Ser  Thr  Pro  Thr  Trp  Glu  Glu  Ser  Asn  Ala  Tyr  Tyr  Trp  Gln  Pro  Tyr
1                   5                        10                       15
Ala  Leu  Pro  Leu
                20
```

( 2 ) INFORMATION FOR SEQ ID NO:269:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:269:

```
Glu  Thr  Pro  Phe  Thr  Trp  Glu  Glu  Ser  Asn  Ala  Tyr  Tyr  Trp  Gln  Pro
1                   5                        10                       15
Tyr  Ala  Leu  Pro  Leu
                20
```

( 2 ) INFORMATION FOR SEQ ID NO:270:

( i ) SEQUENCE CHARACTERISTICS:

(A) LENGTH: 21 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:270:

Lys Ala Pro Phe Thr Trp Glu Glu Ser Gln Ala Tyr Tyr Trp Gln Pro
1               5                   10                  15

Tyr Ala Leu Pro Leu
            20

(2) INFORMATION FOR SEQ ID NO:271:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:271:

Ser Thr Ser Phe Thr Trp Glu Glu Ser Asn Ala Tyr Tyr Trp Gln Pro
1               5                   10                  15

Tyr Ala Leu Pro Leu
            20

(2) INFORMATION FOR SEQ ID NO:272:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:272:

Asp Ser Thr Phe Thr Trp Glu Glu Ser Asn Ala Tyr Tyr Trp Gln Pro
1               5                   10                  15

Tyr Ala Leu Pro Leu
            20

(2) INFORMATION FOR SEQ ID NO:273:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:273:

Tyr Ile Pro Phe Thr Trp Glu Glu Ser Asn Ala Tyr Tyr Trp Gln Pro
1               5                   10                  15

Tyr Ala Leu Pro Leu
            20

(2) INFORMATION FOR SEQ ID NO:274:

(i) SEQUENCE CHARACTERISTICS:
            (A) LENGTH: 21 amino acids
            (B) TYPE: amino acid
            (C) STRANDEDNESS: single
            (D) TOPOLOGY: linear ( i i ) MOLECULE TYPE: peptide ( x i ) SEQUENCE DESCRIPTION: SEQ ID NO:274:

Gln Thr Ala Phe Thr Trp Glu Glu Ser Asn Ala Tyr Tyr Trp Gln Pro
1               5                   10                  15

Tyr Ala Leu Pro Leu
            20

( 2 ) INFORMATION FOR SEQ ID NO:275:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:275:

Glu Thr Leu Phe Thr Trp Glu Glu Ser Asn Ala Thr Tyr Trp Gln Pro
1               5                   10                  15

Tyr Ala Leu Pro Leu
            20

( 2 ) INFORMATION FOR SEQ ID NO:276:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:276:

Val Ser Ser Phe Thr Trp Glu Glu Ser Asn Ala Tyr Tyr Trp Gln Pro
1               5                   10                  15

Tyr Ala Leu Pro Leu
            20

( 2 ) INFORMATION FOR SEQ ID NO:277:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:277:

Ala Asp Val Leu Tyr Trp Gln Pro Tyr Ala Pro Val Thr Leu Trp Val
1               5                   10                  15

( 2 ) INFORMATION FOR SEQ ID NO:278:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:278:

Gly Asp Val Ala Glu Tyr Trp Gln Pro Tyr Ala Leu Pro Leu Thr Ser
1               5                   10                  15

Leu (2) INFORMATION FOR SEQ ID NO:279:

(i) SEQUENCE CHARACTERISTICS:
　　　　(A) LENGTH: 18 amino acids
　　　　(B) TYPE: amino acid
　　　　(C) STRANDEDNESS: single
　　　　(D) TOPOLOGY: linear (ii) MOLECULE TYPE: peptide (xi) SEQUENCE DESCRIPTION: SEQ ID NO:279:

Ser Trp Thr Asp Tyr Gly Tyr Trp Gln Pro Tyr Ala Leu Pro Ile Ser
1               5                   10                  15

Gly Leu (2) INFORMATION FOR SEQ ID NO:280:

(i) SEQUENCE CHARACTERISTICS:
　　　　(A) LENGTH: 11 amino acids
　　　　(B) TYPE: amino acid
　　　　(C) STRANDEDNESS: single
　　　　(D) TOPOLOGY: linear (ii) MOLECULE TYPE: peptide (xi) SEQUENCE DESCRIPTION: SEQ ID NO:280:

Asp Asn Ser Ser Trp Tyr Asp Ser Phe Leu Leu
1               5                   10

(2) INFORMATION FOR SEQ ID NO:281:

(i) SEQUENCE CHARACTERISTICS:

(xi) SEQUENCE DESCRIPTION: SEQ ID NO:281:

This sequence has been intentionally skipped (2) INFORMATION FOR SEQ ID NO:282:

(i) SEQUENCE CHARACTERISTICS:
　　　　(A) LENGTH: 12 amino acids
　　　　(B) TYPE: amino acid
　　　　(C) STRANDEDNESS: single
　　　　(D) TOPOLOGY: linear (ii) MOLECULE TYPE: peptide (ix) FEATURE:
　　　　(A) NAME/KEY: Region
　　　　(B) LOCATION: 5
　　　　(D) OTHER INFORMATION: /note="naphthylalanine."

(xi) SEQUENCE DESCRIPTION: SEQ ID NO:282:

Ser His Leu Tyr Ala Gln Pro Tyr Ser Val Gln Met
1               5                   10

(2) INFORMATION FOR SEQ ID NO:283:

(i) SEQUENCE CHARACTERISTICS:
　　　　(A) LENGTH: 12 amino acids
　　　　(B) TYPE: amino acid
　　　　(C) STRANDEDNESS: single
　　　　(D) TOPOLOGY: linear (ii) MOLECULE TYPE: peptide (ix) FEATURE:
　　　　(A) NAME/KEY: Region ( B ) LOCATION: 5
                ( D ) OTHER INFORMATION: /note="naphthylalanine."

( x i ) SEQUENCE DESCRIPTION: SEQ ID NO:283:

Thr  Leu  Val  Tyr  Ala  Gln  Pro  Tyr  Ser  Leu  Gln  Thr
    1                   5                        10

( 2 ) INFORMATION FOR SEQ ID NO:284:

( i ) SEQUENCE CHARACTERISTICS:
                ( A ) LENGTH: 12 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: Region
                ( B ) LOCATION: 5
                ( D ) OTHER INFORMATION: /note="naphthylalanine."

( x i ) SEQUENCE DESCRIPTION: SEQ ID NO:284:

Arg  Gly  Asp  Tyr  Ala  Gln  Pro  Tyr  Ser  Val  Gln  Ser
    1                   5                        10

( 2 ) INFORMATION FOR SEQ ID NO:285:

( i ) SEQUENCE CHARACTERISTICS:
                ( A ) LENGTH: 12 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: Region
                ( B ) LOCATION: 5
                ( D ) OTHER INFORMATION: /note="naphthylalanine."

( x i ) SEQUENCE DESCRIPTION: SEQ ID NO:285:

Asn  Met  Val  Tyr  Ala  Gln  Pro  Tyr  Ser  Ile  Gln  Thr
    1                   5                        10

( 2 ) INFORMATION FOR SEQ ID NO:286:

( i ) SEQUENCE CHARACTERISTICS:
                ( A ) LENGTH: 9 amino acids
                ( B ) TYPE: amino acid
                ( C ) STRANDEDNESS: single
                ( D ) TOPOLOGY: linear ( i i ) MOLECULE TYPE: peptide ( x i ) SEQUENCE DESCRIPTION: SEQ ID NO:286:

Val  Tyr  Trp  Gln  Pro  Tyr  Ser  Val  Gln
    1                   5

( 2 ) INFORMATION FOR SEQ ID NO:287:

( i ) SEQUENCE CHARACTERISTICS:
                ( A ) LENGTH: 9 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: Region
                ( B ) LOCATION: 3

(D) OTHER INFORMATION: /note="naphthylalanine."

(x i) SEQUENCE DESCRIPTION: SEQ ID NO:287:

Val Tyr Ala Gln Pro Tyr Ser Val Gln
1               5

(2) INFORMATION FOR SEQ ID NO:288:

(i) SEQUENCE CHARACTERISTICS:
      (A) LENGTH: 12 amino acids
      (B) TYPE: amino acid
      (C) STRANDEDNESS: single
      (D) TOPOLOGY: linear (i i) MOLECULE TYPE: peptide (i x) FEATURE:
      (A) NAME/KEY: Region
      (B) LOCATION: 7
      (D) OTHER INFORMATION: /note="Xaa is azetidine."

(x i) SEQUENCE DESCRIPTION: SEQ ID NO:288:

Thr Phe Val Tyr Trp Gln Xaa Tyr Ala Leu Pro Leu
1               5                   10

(2) INFORMATION FOR SEQ ID NO:289:

(i) SEQUENCE CHARACTERISTICS:
      (A) LENGTH: 9 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:289:

Val Tyr Trp Gln Pro Tyr Ser Val Gln
1               5

(2) INFORMATION FOR SEQ ID NO:290:

(i) SEQUENCE CHARACTERISTICS:
      (A) LENGTH: 12 amino acids
      (B) TYPE: amino acid
      (C) STRANDEDNESS: single
      (D) TOPOLOGY: linear (i i) MOLECULE TYPE: peptide (i x) FEATURE:
      (A) NAME/KEY: Region
      (B) LOCATION: 5
      (D) OTHER INFORMATION: /note="naphthylalanine."

(x i) SEQUENCE DESCRIPTION: SEQ ID NO:290:

Arg Leu Val Tyr Ala Gln Pro Tyr Ser Val Gln Arg
1               5                   10

(2) INFORMATION FOR SEQ ID NO:291:

(i) SEQUENCE CHARACTERISTICS:
      (A) LENGTH: 12 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:291:

Arg Leu Asp Tyr Trp Gln Pro Tyr Ser Val Gln Arg
1               5                   10

( 2 ) INFORMATION FOR SEQ ID NO:292:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:292:

```
Arg Leu Val Trp Phe Gln Pro Tyr Ser Val Gln Arg
1               5                   10
```

( 2 ) INFORMATION FOR SEQ ID NO:293:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:293:

```
Arg Leu Val Tyr Trp Gln Pro Tyr Ser Ile Gln Arg
1               5                   10
```

( 2 ) INFORMATION FOR SEQ ID NO:294:

( i ) SEQUENCE CHARACTERISTICS:

( x i ) SEQUENCE DESCRIPTION: SEQ ID NO:294:

This application has been intentionally skipped ( 2 ) INFORMATION FOR SEQ ID NO:295:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:295:

```
Trp Trp Thr Asp Asp Gly Leu Trp Ala Ser Gly Ser
1               5                   10
```

( 2 ) INFORMATION FOR SEQ ID NO:296:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:296:

```
Ala Ser Gly Ser
1
```

( 2 ) INFORMATION FOR SEQ ID NO:297:

( i ) SEQUENCE CHARACTERISTICS:
        ( A ) LENGTH: 12 amino acids
        ( B ) TYPE: amino acid (C) STRANDEDNESS: single
            (D) TOPOLOGY: linear (ii) MOLECULE TYPE: peptide (ix) FEATURE:
            (A) NAME/KEY: Region
            (B) LOCATION: 12
            (D) OTHER INFORMATION: /note="C-terminal Ile is amidated."

(xi) SEQUENCE DESCRIPTION: SEQ ID NO:297:

Tyr Trp Asp Thr Arg Gly Leu Trp Val Tyr Thr Ile
1               5                   10

(2) INFORMATION FOR SEQ ID NO:298:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Region
            (B) LOCATION: 1
            (D) OTHER INFORMATION: /note="Xaa is Asp, Glu, Gln, Ser, Thr,
                Val or Tyr."

(ix) FEATURE:
            (A) NAME/KEY: Region
            (B) LOCATION: 2
            (D) OTHER INFORMATION: /note="Xaa is Ala, Asp, Gly, Ile, Asn,
                Ser, Thr, Val."

(ix) FEATURE:
            (A) NAME/KEY: Region
            (B) LOCATION: 3
            (D) OTHER INFORMATION: /note="Xaa is Ala, Gly, Leu, Asn,
                Pro, Ser, Thr, or Tyr."

(ix) FEATURE:
            (A) NAME/KEY: Region
            (B) LOCATION: 4
            (D) OTHER INFORMATION: /note="Xaa is Asp, Glu, Phe, Leu,
                Val or Tyr."

(ix) FEATURE:
            (A) NAME/KEY: Region
            (B) LOCATION: 5
            (D) OTHER INFORMATION: /note="Xaa is Asp, Arg, Ser or Thr."

(ix) FEATURE:
            (A) NAME/KEY: Region
            (B) LOCATION: 6
            (D) OTHER INFORMATION: /note="Xaa is His, Pro, Ser or Trp."

(ix) FEATURE:
            (A) NAME/KEY: Region
            (B) LOCATION: 7
            (D) OTHER INFORMATION: /note="Xaa is Glu, Phe, Asn,
                Gln, Arg, Ser."

(ix) FEATURE:
            (A) NAME/KEY: Region
            (B) LOCATION: 8
            (D) OTHER INFORMATION: /note="Xaa is Asp, Glu, Phe, Gln or
                Trp."

(ix) FEATURE:
            (A) NAME/KEY: Region
            (B) LOCATION: 9
            (D) OTHER INFORMATION: /note="Xaa is Ser, Thr or Trp."

(ix) FEATURE:
            (A) NAME/KEY: Region
            (B) LOCATION: 10

( D ) OTHER INFORMATION: /note="Xaa is Asp, Gly, Lys, Asn,
Gln, Ser or Thr."

( i x ) FEATURE:
    ( A ) NAME/KEY: Region
    ( B ) LOCATION: 11
    ( D ) OTHER INFORMATION: /note="Xaa is Ala, Glu, Pro, Ser or
Tyr."

( i x ) FEATURE:
    ( A ) NAME/KEY: Region
    ( B ) LOCATION: 12
    ( D ) OTHER INFORMATION: /note="Xaa is Val, Leu, Ile, Glu, Pro,
Gly, Tyr, Met, Thr or Asp."

( i x ) FEATURE:
    ( A ) NAME/KEY: Region
    ( B ) LOCATION: 13
    ( D ) OTHER INFORMATION: /note="Xaa is Tyr, Trp or Phe."

( i x ) FEATURE:
    ( A ) NAME/KEY: Region
    ( B ) LOCATION: 14
    ( D ) OTHER INFORMATION: /note="Xaa is Tyr, Trp or Phe."

( i x ) FEATURE:
    ( A ) NAME/KEY: Region
    ( B ) LOCATION: 16
    ( D ) OTHER INFORMATION: /note="Xaa is Pro or Azetidine."

( i x ) FEATURE:
    ( A ) NAME/KEY: Region
    ( B ) LOCATION: 18
    ( D ) OTHER INFORMATION: /note="Xaa is Ser, Ala, Val, or Leu."

( i x ) FEATURE:
    ( A ) NAME/KEY: Region
    ( B ) LOCATION: 19
    ( D ) OTHER INFORMATION: /note="Xaa is Val, Leu, Ile or Glu."

( i x ) FEATURE:
    ( A ) NAME/KEY: Region
    ( B ) LOCATION: 20
    ( D ) OTHER INFORMATION: /note="Xaa is Gln or Pro."

( x i ) SEQUENCE DESCRIPTION: SEQ ID NO:298:

Xaa Xaa Xaa Xaa Xaa Xaa Xaa Xaa Xaa Xaa Xaa Xaa Xaa Xaa Gln Xaa
1                        5                                10                          15

Tyr Xaa Xaa Xaa Leu
              20

( 2 ) INFORMATION FOR SEQ ID NO:299:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 7
        ( D ) OTHER INFORMATION: /note="Xaa is Azetidine."

( x i ) SEQUENCE DESCRIPTION: SEQ ID NO:299:

Thr Phe Val Tyr Trp Gln Xaa Ala Leu Pro Leu
1                     5                              10

( 2 ) INFORMATION FOR SEQ ID NO:300:

( i ) SEQUENCE CHARACTERISTICS:
        ( A ) LENGTH: 12 amino acids
        ( B ) TYPE: amino acid ( C ) STRANDEDNESS: single
( D ) TOPOLOGY: linear ( i i ) MOLECULE TYPE: peptide ( x i ) SEQUENCE DESCRIPTION: SEQ ID NO:300:

```
Xaa Xaa Xaa Xaa Xaa Xaa Pro Tyr Ser Val Gln Arg
1               5                   10
```

( 2 ) INFORMATION FOR SEQ ID NO:301:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:301:

```
Arg Leu Val Tyr Trp Gln Xaa Xaa Xaa Xaa Xaa Xaa
1               5                   10
```

( 2 ) INFORMATION FOR SEQ ID NO:302:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:302:

```
Ser Arg Val Trp Tyr Gln Xaa Xaa Xaa Xaa Xaa Xaa
1               5                   10
```

( 2 ) INFORMATION FOR SEQ ID NO:303:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:303:

```
Xaa Xaa Xaa Xaa Xaa Xaa Pro Tyr Ala Leu Pro Leu
1               5                   10
```

( 2 ) INFORMATION FOR SEQ ID NO:304:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:304:

```
Arg Leu Val Tyr Trp Gln Pro Tyr Ser Val Gln Arg
1               5                   10
```

( 2 ) INFORMATION FOR SEQ ID NO:305:

( i ) SEQUENCE CHARACTERISTICS:
        ( A ) LENGTH: 9 amino acids
        ( B ) TYPE: amino acid ( C ) STRANDEDNESS: single
( D ) TOPOLOGY: linear ( i i ) MOLECULE TYPE: peptide ( x i ) SEQUENCE DESCRIPTION: SEQ ID NO:305:

Xaa Xaa Gln Pro Tyr Xaa Xaa Xaa Xaa
1               5

( 2 ) INFORMATION FOR SEQ ID NO:306:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:306:

Xaa Xaa Xaa Gln Pro Tyr Xaa Xaa Xaa Xaa
1               5                   10

( 2 ) INFORMATION FOR SEQ ID NO:307:

( i ) SEQUENCE CHARACTERISTICS:
( A ) LENGTH: 20 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:307:

Thr Phe Val Tyr Trp Gln Pro Tyr Xaa Xaa Xaa Xaa Xaa Xaa Xaa Xaa
1               5                   10                      15

Xaa Xaa Xaa Xaa
            20

( 2 ) INFORMATION FOR SEQ ID NO:308:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:308:

Xaa Xaa Xaa Gln Pro Tyr Xaa Xaa Xaa Xaa Xaa Xaa
1               5                   10

( 2 ) INFORMATION FOR SEQ ID NO:309:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:309:

Xaa Xaa Xaa Xaa Val Tyr Trp Gln Pro Tyr Ser Val Gln Xaa Xaa Xaa
1               5                   10                      15

Xaa ( 2 ) INFORMATION FOR SEQ ID NO:310:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:310:

Xaa Xaa Xaa Xaa Xaa Xaa Pro Tyr Ala Leu Pro Leu
1               5                   10

( 2 ) INFORMATION FOR SEQ ID NO:311:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:311:

Xaa Xaa Xaa Xaa Xaa Xaa Trp Tyr Gln Pro Tyr Ala Leu Pro Leu
1               5                   10                  15

( 2 ) INFORMATION FOR SEQ ID NO:312:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:312:

Xaa Xaa Xaa Xaa Xaa Xaa Xaa Xaa Xaa Xaa Xaa Xaa Tyr Trp Gln Pro
1               5                   10                  15

Tyr Ala Leu Pro Leu
                20

( 2 ) INFORMATION FOR SEQ ID NO:313:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 13
        ( D ) OTHER INFORMATION: /note="Xaa is Azetidine."

( i x ) FEATURE:
        ( A ) NAME/KEY: Region
        ( B ) LOCATION: 14
        ( D ) OTHER INFORMATION: /note="C-terminal Tyr is amidated."

( x i ) SEQUENCE DESCRIPTION: SEQ ID NO:313:

Phe Thr Trp Glu Glu Ser Asn Ala Tyr Tyr Trp Gln Xaa Tyr
1               5                   10

( 2 ) INFORMATION FOR SEQ ID NO:314:

( i ) SEQUENCE CHARACTERISTICS:

( A ) LENGTH: 11 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: Region
                ( B ) LOCATION: 1
                ( D ) OTHER INFORMATION: /note="Xaa is Asp or Tyr."

( i x ) FEATURE:
                ( A ) NAME/KEY: Region
                ( B ) LOCATION: 3
                ( D ) OTHER INFORMATION: /note="Xaa is Asp or Ser."

( i x ) FEATURE:
                ( A ) NAME/KEY: Region
                ( B ) LOCATION: one-of (5,8)
                ( D ) OTHER INFORMATION: /note="Xaa is Ser or Trp."

( i x ) FEATURE:
                ( A ) NAME/KEY: Region
                ( B ) LOCATION: 6
                ( D ) OTHER INFORMATION: /note="Xaa is Ser or Tyr."

( i x ) FEATURE:
                ( A ) NAME/KEY: Region
                ( B ) LOCATION: 7
                ( D ) OTHER INFORMATION: /note="Xaa is Asp or Val."

( i x ) FEATURE:
                ( A ) NAME/KEY: Region
                ( B ) LOCATION: 8
                ( D ) OTHER INFORMATION: /note="Xaa is Ser or Trp."

( i x ) FEATURE:
                ( A ) NAME/KEY: Region
                ( B ) LOCATION: 9
                ( D ) OTHER INFORMATION: /note="Xaa is Phe or Leu."

( i x ) FEATURE:
                ( A ) NAME/KEY: Region
                ( B ) LOCATION: 10
                ( D ) OTHER INFORMATION: /note="Xaa is Asp or Leu."

( x i ) SEQUENCE DESCRIPTION: SEQ ID NO:314:

Xaa  Asn  Xaa  Ser  Xaa  Xaa  Xaa  Xaa  Xaa  Xaa  Leu
        1                   5                             10

( 2 ) INFORMATION FOR SEQ ID NO:315:

( i ) SEQUENCE CHARACTERISTICS:
                ( A ) LENGTH: 11 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: Region
                ( B ) LOCATION: 11
                ( D ) OTHER INFORMATION: /note="C-terminal Tyr is amidated."

( x i ) SEQUENCE DESCRIPTION: SEQ ID NO:315:

Phe  Glu  Trp  Thr  Pro  Gly  Tyr  Trp  Gln  Pro  Tyr
        1                   5                             10

( 2 ) INFORMATION FOR SEQ ID NO:316:

( i ) SEQUENCE CHARACTERISTICS:
                ( A ) LENGTH: 11 amino acids
                ( B ) TYPE: amino acid
                ( C ) STRANDEDNESS: single ( D ) TOPOLOGY: linear ( i i ) MOLECULE TYPE: peptide ( i x ) FEATURE:
    ( A ) NAME/KEY: Region
    ( B ) LOCATION: 10
    ( D ) OTHER INFORMATION: /note="Xaa is Azetidine."

( i x ) FEATURE:
    ( A ) NAME/KEY: Region
    ( B ) LOCATION: 11
    ( D ) OTHER INFORMATION: /note="C-terminal Tyr is amidated."

( x i ) SEQUENCE DESCRIPTION: SEQ ID NO:316:

Phe Glu Trp Thr Pro Gly Tyr Trp Gln Xaa Tyr
1               5                   10

( 2 ) INFORMATION FOR SEQ ID NO:317:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Region
    ( B ) LOCATION: 10
    ( D ) OTHER INFORMATION: /note="Xaa is Azetidine."

( i x ) FEATURE:
    ( A ) NAME/KEY: Region
    ( B ) LOCATION: 11
    ( D ) OTHER INFORMATION: /note="C-terminal Tyr is amidated."

( x i ) SEQUENCE DESCRIPTION: SEQ ID NO:317:

Phe Glu Trp Thr Pro Gly Trp Tyr Gln Xaa Tyr
1               5                   10

( 2 ) INFORMATION FOR SEQ ID NO:318:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Region
    ( B ) LOCATION: 1
    ( D ) OTHER INFORMATION: /note="N-terminal Phe is
        acetylated."

( i x ) FEATURE:
    ( A ) NAME/KEY: Region
    ( B ) LOCATION: 10
    ( D ) OTHER INFORMATION: /note="Xaa is Azetidine."

( i x ) FEATURE:
    ( A ) NAME/KEY: Region
    ( B ) LOCATION: 11
    ( D ) OTHER INFORMATION: /note="C-terminal Tyr is amidated."

( x i ) SEQUENCE DESCRIPTION: SEQ ID NO:318:

Phe Glu Trp Thr Pro Gly Trp Tyr Gln Xaa Tyr
1               5                   10

( 2 ) INFORMATION FOR SEQ ID NO:319:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Region
    ( B ) LOCATION: 8
    ( D ) OTHER INFORMATION: /note="Xaa is phosphotyrosine."

( i x ) FEATURE:
    ( A ) NAME/KEY: Region
    ( B ) LOCATION: 10
    ( D ) OTHER INFORMATION: /note="Xaa is Azetidine."

( i x ) FEATURE:
    ( A ) NAME/KEY: Region
    ( B ) LOCATION: 11
    ( D ) OTHER INFORMATION: /note="C-terminal Tyr is amidated."

( x i ) SEQUENCE DESCRIPTION: SEQ ID NO:319:

```
Phe  Glu  Trp  Thr  Pro  Gly  Trp  Xaa  Gln  Xaa  Tyr
1                  5                        10
```

( 2 ) INFORMATION FOR SEQ ID NO:320:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Region
    ( B ) LOCATION: 10
    ( D ) OTHER INFORMATION: /note="Xaa is Azetidine."

( i x ) FEATURE:
    ( A ) NAME/KEY: Region
    ( B ) LOCATION: 11
    ( D ) OTHER INFORMATION: /note="C-terminal Tyr is amidated."

( x i ) SEQUENCE DESCRIPTION: SEQ ID NO:320:

```
Phe  Ala  Trp  Thr  Pro  Gly  Tyr  Trp  Gln  Xaa  Tyr
1                  5                        10
```

( 2 ) INFORMATION FOR SEQ ID NO:321:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Region
    ( B ) LOCATION: 10
    ( D ) OTHER INFORMATION: /note="Xaa is Azetidine."

( i x ) FEATURE:
    ( A ) NAME/KEY: Region
    ( B ) LOCATION: 11
    ( D ) OTHER INFORMATION: /note="C-terminal Tyr is amidated."

( x i ) SEQUENCE DESCRIPTION: SEQ ID NO:321:

```
Phe  Glu  Trp  Ala  Pro  Gly  Tyr  Trp  Gln  Xaa  Tyr
1                  5                        10
```

( 2 ) INFORMATION FOR SEQ ID NO:322:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 10
        ( D ) OTHER INFORMATION: /note="Xaa is Azetidine."

( i x ) FEATURE:
        ( A ) NAME/KEY: Region
        ( B ) LOCATION: 11
        ( D ) OTHER INFORMATION: /note="C-terminal Tyr is amidated."

( x i ) SEQUENCE DESCRIPTION: SEQ ID NO:322:

```
Phe Glu Trp Val Pro Gly Tyr Trp Gln Xaa Tyr
 1           5                   10
```

( 2 ) INFORMATION FOR SEQ ID NO:323:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 10
        ( D ) OTHER INFORMATION: /note="Xaa is Azetidine."

( i x ) FEATURE:
        ( A ) NAME/KEY: Region
        ( B ) LOCATION: 11
        ( D ) OTHER INFORMATION: /note="C-terminal Tyr is amidated."

( x i ) SEQUENCE DESCRIPTION: SEQ ID NO:323:

```
Phe Glu Trp Thr Pro Gly Tyr Trp Gln Xaa Tyr
 1           5                   10
```

( 2 ) INFORMATION FOR SEQ ID NO:324:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 1
        ( D ) OTHER INFORMATION: /note="N-terminal Phe is
            acetylated."

( i x ) FEATURE:
        ( A ) NAME/KEY: Region
        ( B ) LOCATION: 10
        ( D ) OTHER INFORMATION: /note="Xaa is Azetidine."

( i x ) FEATURE:
        ( A ) NAME/KEY: Region
        ( B ) LOCATION: 11
        ( D ) OTHER INFORMATION: /note="C-terminal Tyr is amidated."

( x i ) SEQUENCE DESCRIPTION: SEQ ID NO:324:

```
Phe Glu Trp Thr Pro Gly Tyr Trp Gln Xaa Tyr
1               5                   10
```

( 2 ) INFORMATION FOR SEQ ID NO:325:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 10
        ( D ) OTHER INFORMATION: /note="Xaa is Azetidine."

( i x ) FEATURE:
        ( A ) NAME/KEY: Region
        ( B ) LOCATION: 11
        ( D ) OTHER INFORMATION: /note="C-terminal is amidated p-
        benzoyl-L- phenylalanine."

( x i ) SEQUENCE DESCRIPTION: SEQ ID NO:325:

```
Phe Glu Trp Thr Pro Gly Tyr Tyr Gln Xaa Xaa
1               5                   10
```

( 2 ) INFORMATION FOR SEQ ID NO:326:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 6
        ( D ) OTHER INFORMATION: /note="Xaa is sarcosine."

( i x ) FEATURE:
        ( A ) NAME/KEY: Region
        ( B ) LOCATION: 10
        ( D ) OTHER INFORMATION: /note="Xaa is Azetidine."

( i x ) FEATURE:
        ( A ) NAME/KEY: Region
        ( B ) LOCATION: 11
        ( D ) OTHER INFORMATION: /note="C-terminal Tyr is amidated."

( x i ) SEQUENCE DESCRIPTION: SEQ ID NO:326:

```
Phe Glu Trp Thr Pro Xaa Trp Tyr Gln Xaa Tyr
1               5                   10
```

( 2 ) INFORMATION FOR SEQ ID NO:327:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 11
        ( D ) OTHER INFORMATION: /note="C-terminal Tyr is amidated."

( x i ) SEQUENCE DESCRIPTION: SEQ ID NO:327:

```
Phe Glu Trp Thr Pro Gly Tyr Tyr Gln Pro Tyr
 1           5                   10
```

( 2 ) INFORMATION FOR SEQ ID NO:328:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 11
        ( D ) OTHER INFORMATION: /note="C-terminal Tyr is amidated."

( x i ) SEQUENCE DESCRIPTION: SEQ ID NO:328:

```
Phe Glu Trp Thr Pro Gly Trp Trp Gln Pro Tyr
 1           5                   10
```

( 2 ) INFORMATION FOR SEQ ID NO:329:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 11
        ( D ) OTHER INFORMATION: /note="C-terminal Tyr is amidated."

( x i ) SEQUENCE DESCRIPTION: SEQ ID NO:329:

```
Phe Glu Trp Thr Pro Asn Tyr Trp Gln Pro Tyr
 1           5                   10
```

( 2 ) INFORMATION FOR SEQ ID NO:330:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(1, 3)
        ( D ) OTHER INFORMATION: /note="Xaa is phosphotyrosine."

( i x ) FEATURE:
        ( A ) NAME/KEY: Region
        ( B ) LOCATION: 5
        ( D ) OTHER INFORMATION: /note="Xaa is Azetidine."

( i x ) FEATURE:
        ( A ) NAME/KEY: Region
        ( B ) LOCATION: 2
        ( D ) OTHER INFORMATION: /note="Xaa is naphthylalanine."

( x i ) SEQUENCE DESCRIPTION: SEQ ID NO:330:

```
Xaa Xaa Xaa Gln Xaa Tyr Ala Leu Pro Leu
 1           5                   10
```

( 2 ) INFORMATION FOR SEQ ID NO:331:

( i ) SEQUENCE CHARACTERISTICS:

( A ) LENGTH: 15 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:331:

Phe Glu Trp Thr Pro Gly Tyr Trp Gln Pro Tyr Ala Leu Pro Leu
1               5                   10                  15

( 2 ) INFORMATION FOR SEQ ID NO:332:

( i ) SEQUENCE CHARACTERISTICS:
( A ) LENGTH: 18 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Region
( B ) LOCATION: 13
( D ) OTHER INFORMATION: /note="Xaa is Azetidine."

( x i ) SEQUENCE DESCRIPTION: SEQ ID NO:332:

Phe Thr Trp Glu Glu Ser Asn Ala Tyr Tyr Trp Gln Xaa Tyr Ala Leu
1               5                   10                  15

Pro Leu ( 2 ) INFORMATION FOR SEQ ID NO:333:

( i ) SEQUENCE CHARACTERISTICS:
( A ) LENGTH: 14 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Region
( B ) LOCATION: 14
( D ) OTHER INFORMATION: /note="Xaa is tyrosinamide."

( x i ) SEQUENCE DESCRIPTION: SEQ ID NO:333:

Phe Thr Trp Glu Glu Ser Asn Ala Tyr Tyr Trp Gln Pro Xaa
1               5                   10

( 2 ) INFORMATION FOR SEQ ID NO:334:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:334:

Asp Asn Thr Ala Trp Tyr Glu Ser Phe Leu Ala
1               5                   10

( 2 ) INFORMATION FOR SEQ ID NO:335:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:335:

Asp Asn Thr Ala Trp Tyr Glu Asn Phe Leu Leu
1               5                   10

( 2 ) INFORMATION FOR SEQ ID NO:336:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Region
      ( B ) LOCATION: 10
      ( D ) OTHER INFORMATION: /note="Xaa is tyrosinamide."

( x i ) SEQUENCE DESCRIPTION: SEQ ID NO:336:

Glu Trp Thr Pro Gly Tyr Trp Gln Pro Xaa
1               5                   10

( 2 ) INFORMATION FOR SEQ ID NO:337:

( i ) SEQUENCE CHARACTERISTICS:
      ( A ) LENGTH: 11 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Region
      ( B ) LOCATION: 10
      ( D ) OTHER INFORMATION: /note="Xaa is azetidine."

( i x ) FEATURE:
      ( A ) NAME/KEY: Region
      ( B ) LOCATION: 11
      ( D ) OTHER INFORMATION: /note="Xaa is tyrosinamide."

( x i ) SEQUENCE DESCRIPTION: SEQ ID NO:337:

Ala Glu Trp Thr Pro Gly Tyr Trp Gln Xaa Xaa
1               5                   10

( 2 ) INFORMATION FOR SEQ ID NO:338:

( i ) SEQUENCE CHARACTERISTICS:
      ( A ) LENGTH: 11 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Region
      ( B ) LOCATION: 10
      ( D ) OTHER INFORMATION: /note="Xaa is azetidine."

( i x ) FEATURE:
      ( A ) NAME/KEY: Region
      ( B ) LOCATION: 11
      ( D ) OTHER INFORMATION: /note="Xaa is tyrosinamide."

( x i ) SEQUENCE DESCRIPTION: SEQ ID NO:338:

Phe Glu Ala Thr Pro Gly Tyr Trp Gln Xaa Xaa
1               5                   10

( 2 ) INFORMATION FOR SEQ ID NO:339:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 10
        ( D ) OTHER INFORMATION: /note="Xaa is azetidine."

( i x ) FEATURE:
        ( A ) NAME/KEY: Region
        ( B ) LOCATION: 11
        ( D ) OTHER INFORMATION: /note="Xaa is tyrosinamide."

( x i ) SEQUENCE DESCRIPTION: SEQ ID NO:339:

Phe Glu Trp Thr Ala Gly Tyr Trp Gln Xaa Xaa
1                 5                           10

( 2 ) INFORMATION FOR SEQ ID NO:340:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 10
        ( D ) OTHER INFORMATION: /note="Xaa is azetidine."

( i x ) FEATURE:
        ( A ) NAME/KEY: Region
        ( B ) LOCATION: 11
        ( D ) OTHER INFORMATION: /note="Xaa is tyrosinamide."

( x i ) SEQUENCE DESCRIPTION: SEQ ID NO:340:

Phe Glu Trp Thr Pro Ala Tyr Trp Gln Xaa Xaa
1                 5                           10

( 2 ) INFORMATION FOR SEQ ID NO:341:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 10
        ( D ) OTHER INFORMATION: /note="Xaa is azetidine."

( i x ) FEATURE:
        ( A ) NAME/KEY: Region
        ( B ) LOCATION: 11
        ( D ) OTHER INFORMATION: /note="Xaa is tyrosinamide."

( x i ) SEQUENCE DESCRIPTION: SEQ ID NO:341:

Phe Glu Trp Thr Pro Gly Ala Trp Gln Xaa Xaa
1                 5                           10

( 2 ) INFORMATION FOR SEQ ID NO:342:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 10
        ( D ) OTHER INFORMATION: /note="Xaa is azetidine."

( i x ) FEATURE:
        ( A ) NAME/KEY: Region
        ( B ) LOCATION: 11
        ( D ) OTHER INFORMATION: /note="Xaa is tyrosinamide."

( x i ) SEQUENCE DESCRIPTION: SEQ ID NO:342:

Phe Glu Trp Thr Pro Gly Tyr Ala Gln Xaa Xaa
1               5                   10

( 2 ) INFORMATION FOR SEQ ID NO:343:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 10
        ( D ) OTHER INFORMATION: /note="Xaa is azetidine."

( i x ) FEATURE:
        ( A ) NAME/KEY: Region
        ( B ) LOCATION: 11
        ( D ) OTHER INFORMATION: /note="Xaa is tyrosinamide."

( x i ) SEQUENCE DESCRIPTION: SEQ ID NO:343:

Phe Glu Trp Thr Pro Gly Tyr Trp Ala Xaa Xaa
1               5                   10

( 2 ) INFORMATION FOR SEQ ID NO:344:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 10
        ( D ) OTHER INFORMATION: /note="Xaa is azetidine."

( i x ) FEATURE:
        ( A ) NAME/KEY: Region
        ( B ) LOCATION: 11
        ( D ) OTHER INFORMATION: /note="C-terminal Ala is amidated."

( x i ) SEQUENCE DESCRIPTION: SEQ ID NO:344:

Phe Glu Trp Thr Pro Gly Tyr Trp Gln Xaa Ala
1               5                   10

( 2 ) INFORMATION FOR SEQ ID NO:345:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Region
    ( B ) LOCATION: 10
    ( D ) OTHER INFORMATION: /note="Xaa is azetidine."

( i x ) FEATURE:
    ( A ) NAME/KEY: Region
    ( B ) LOCATION: 11
    ( D ) OTHER INFORMATION: /note="Xaa is tyrosinamide."

( x i ) SEQUENCE DESCRIPTION: SEQ ID NO:345:

```
Phe  Glu  Trp  Thr  Gly  Gly  Tyr  Trp  Gln  Xaa  Ala
 1                  5                        10
```

( 2 ) INFORMATION FOR SEQ ID NO:346:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(5, 10)
        ( D ) OTHER INFORMATION: /note="Xaa is azetidine."

( i x ) FEATURE:
        ( A ) NAME/KEY: Region
        ( B ) LOCATION: 11
        ( D ) OTHER INFORMATION: /note="Xaa is tyrosinamide."

( x i ) SEQUENCE DESCRIPTION: SEQ ID NO:346:

```
Phe  Glu  Trp  Thr  Xaa  Gly  Tyr  Trp  Gln  Xaa  Xaa
 1                  5                        10
```

( 2 ) INFORMATION FOR SEQ ID NO:347:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 5
        ( D ) OTHER INFORMATION: /note="Xaa is pipecolic acid."

( i x ) FEATURE:
        ( A ) NAME/KEY: Region
        ( B ) LOCATION: 10
        ( D ) OTHER INFORMATION: /note="Xaa is Azetidine."

( i x ) FEATURE:
        ( A ) NAME/KEY: Region
        ( B ) LOCATION: 11
        ( D ) OTHER INFORMATION: /note="C-terminal Tyr is amidated."

( x i ) SEQUENCE DESCRIPTION: SEQ ID NO:347:

```
Phe  Glu  Trp  Thr  Xaa  Gly  Tyr  Trp  Gln  Xaa  Tyr
 1                  5                        10
```

( 2 ) INFORMATION FOR SEQ ID NO:348:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 6
        ( D ) OTHER INFORMATION: /note="Xaa is aminoisobutyric acid."

( i x ) FEATURE:
        ( A ) NAME/KEY: Region
        ( B ) LOCATION: 10
        ( D ) OTHER INFORMATION: /note="Xaa is Azetidine."

( i x ) FEATURE:
        ( A ) NAME/KEY: Region
        ( B ) LOCATION: 11
        ( D ) OTHER INFORMATION: /note="C-terminal Tyr is amidated."

( x i ) SEQUENCE DESCRIPTION: SEQ ID NO:348:

```
Phe Glu Trp Thr Pro Xaa Tyr Trp Gln Xaa Tyr
 1               5                   10
```

( 2 ) INFORMATION FOR SEQ ID NO:349:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 5
        ( D ) OTHER INFORMATION: /note="Xaa is sarcosine."

( i x ) FEATURE:
        ( A ) NAME/KEY: Region
        ( B ) LOCATION: 10
        ( D ) OTHER INFORMATION: /note="Xaa is Azetidine."

( i x ) FEATURE:
        ( A ) NAME/KEY: Region
        ( B ) LOCATION: 11
        ( D ) OTHER INFORMATION: /note="C-terminal Tyr is amidated."

( x i ) SEQUENCE DESCRIPTION: SEQ ID NO:349:

```
Phe Glu Trp Thr Xaa Gly Tyr Trp Gln Xaa Tyr
 1               5                   10
```

( 2 ) INFORMATION FOR SEQ ID NO:350:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 10
        ( D ) OTHER INFORMATION: /note="Xaa is azetidine."

( i x ) FEATURE:

(A) NAME/KEY: Region
(B) LOCATION: 11
(D) OTHER INFORMATION: /note="Xaa is tyrosinamide."

(xi) SEQUENCE DESCRIPTION: SEQ ID NO:350:

Phe Glu Trp Thr Pro Asn Tyr Trp Gln Xaa Xaa
1               5                   10

(2) INFORMATION FOR SEQ ID NO:351:

(i) SEQUENCE CHARACTERISTICS:
    (A) LENGTH: 11 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Region
    (B) LOCATION: 10
    (D) OTHER INFORMATION: /note="Xaa is azetidine."

(ix) FEATURE:
    (A) NAME/KEY: Region
    (B) LOCATION: 11
    (D) OTHER INFORMATION: /note="Xaa is tyrosinamide."

(xi) SEQUENCE DESCRIPTION: SEQ ID NO:351:

Phe Glu Trp Thr Val Pro Tyr Trp Gln Xaa Xaa
1               5                   10

(2) INFORMATION FOR SEQ ID NO:352:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Region
    (B) LOCATION: 7
    (D) OTHER INFORMATION: /note="Xaa is Azetidine."

(xi) SEQUENCE DESCRIPTION: SEQ ID NO:352:

Thr Phe Val Tyr Trp Gln Xaa Tyr Ala Leu Pro Leu
1               5                   10

(2) INFORMATION FOR SEQ ID NO:353:

(i) SEQUENCE CHARACTERISTICS:
    (A) LENGTH: 21 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:353:

Tyr Ile Pro Phe Thr Trp Glu Glu Ser Asn Ala Tyr Tyr Trp Gln Pro
1               5                   10                  15

Tyr Ala Leu Pro Leu
            20

(2) INFORMATION FOR SEQ ID NO:354:

(i) SEQUENCE CHARACTERISTICS:
    (A) LENGTH: 21 amino acids (B) TYPE: amino acid
(C) STRANDEDNESS: single
(D) TOPOLOGY: linear (i i) MOLECULE TYPE: peptide (x i) SEQUENCE DESCRIPTION: SEQ ID NO:354:

Asp Gly Tyr Asp Arg Trp Arg Gln Ser Gly Glu Arg Tyr Trp Gln Pro
1               5                   10                  15

Tyr Ala Leu Pro Leu
            20

(2) INFORMATION FOR SEQ ID NO:355:

(i) SEQUENCE CHARACTERISTICS:

(x i) SEQUENCE DESCRIPTION: SEQ ID NO:355:

This sequence has been intentionally skipped (2) INFORMATION FOR SEQ ID NO:356:

(i) SEQUENCE CHARACTERISTICS:
    (A) LENGTH: 15 amino acids
    (B) TYPE: amino acid
    (C) STRANDEDNESS: single
    (D) TOPOLOGY: linear (i i) MOLECULE TYPE: peptide (i x) FEATURE:
    (A) NAME/KEY: Region
    (B) LOCATION: 10
    (D) OTHER INFORMATION: /note="Xaa is Azetidine."

(x i) SEQUENCE DESCRIPTION: SEQ ID NO:356:

Phe Glu Trp Thr Pro Gly Tyr Trp Gln Xaa Tyr Ala Leu Pro Leu
1               5                   10                  15

(2) INFORMATION FOR SEQ ID NO:357:

(i) SEQUENCE CHARACTERISTICS:
    (A) LENGTH: 17 amino acids
    (B) TYPE: amino acid
    (C) STRANDEDNESS: single
    (D) TOPOLOGY: linear (i i) MOLECULE TYPE: peptide (i x) FEATURE:
    (A) NAME/KEY: Region
    (B) LOCATION: 17
    (D) OTHER INFORMATION: /note="C-terminal Asp is amidated."

(x i) SEQUENCE DESCRIPTION: SEQ ID NO:357:

Phe Glu Trp Thr Pro Gly Tyr Trp Gln Pro Tyr Ala Leu Pro Leu Ser
1               5                   10                  15

Asp (2) INFORMATION FOR SEQ ID NO:358:

(i) SEQUENCE CHARACTERISTICS:
    (A) LENGTH: 15 amino acids
    (B) TYPE: amino acid
    (C) STRANDEDNESS: single
    (D) TOPOLOGY: linear (i i) MOLECULE TYPE: peptide (i x) FEATURE:
    (A) NAME/KEY: Region ( B ) LOCATION: 10
                    ( D ) OTHER INFORMATION: /note="Xaa is Azetidine."

( x i ) SEQUENCE DESCRIPTION: SEQ ID NO:358:

Phe  Glu  Trp  Thr  Pro  Gly  Tyr  Tyr  Gln  Xaa  Tyr  Ala  Leu  Pro  Leu
1                   5                        10                       15

( 2 ) INFORMATION FOR SEQ ID NO:359:

( i ) SEQUENCE CHARACTERISTICS:
                    ( A ) LENGTH: 11 amino acids
                    ( B ) TYPE: amino acid
                    ( C ) STRANDEDNESS: single
                    ( D ) TOPOLOGY: linear ( i i ) MOLECULE TYPE: peptide ( i x ) FEATURE:
                    ( A ) NAME/KEY: Region
                    ( B ) LOCATION: 1
                    ( D ) OTHER INFORMATION: /note="N-terminal Phe is acetylated."

( i x ) FEATURE:
                    ( A ) NAME/KEY: Region
                    ( B ) LOCATION: 10
                    ( D ) OTHER INFORMATION: /note="Xaa is azetidine."

( i x ) FEATURE:
                    ( A ) NAME/KEY: Region
                    ( B ) LOCATION: 10
                    ( D ) OTHER INFORMATION: /note="Xaa is tyrosinamide."

( x i ) SEQUENCE DESCRIPTION: SEQ ID NO:359:

Phe  Glu  Trp  Thr  Pro  Gly  Tyr  Tyr  Gln  Xaa  Xaa
1                   5                        10

( 2 ) INFORMATION FOR SEQ ID NO:360:

( i ) SEQUENCE CHARACTERISTICS:
                    ( A ) LENGTH: 11 amino acids
                    ( B ) TYPE: amino acid
                    ( C ) STRANDEDNESS: single
                    ( D ) TOPOLOGY: linear ( i i ) MOLECULE TYPE: peptide ( i x ) FEATURE:
                    ( A ) NAME/KEY: Region
                    ( B ) LOCATION: 8
                    ( D ) OTHER INFORMATION: /note="Xaa is p-
                            benzoyl-L- phenylalanine."

( i x ) FEATURE:
                    ( A ) NAME/KEY: Region
                    ( B ) LOCATION: 10
                    ( D ) OTHER INFORMATION: /note="Xaa is Azetidine."

( i x ) FEATURE:
                    ( A ) NAME/KEY: Region
                    ( B ) LOCATION: 11
                    ( D ) OTHER INFORMATION: /note="Xaa is tyrosinamide."

( x i ) SEQUENCE DESCRIPTION: SEQ ID NO:360:

Phe  Glu  Trp  Thr  Pro  Gly  Tyr  Xaa  Gln  Xaa  Xaa
1                   5                        10

( 2 ) INFORMATION FOR SEQ ID NO:361:

( i ) SEQUENCE CHARACTERISTICS:
                    ( A ) LENGTH: 11 amino acids
                    ( B ) TYPE: amino acid
                    ( C ) STRANDEDNESS: single
                    ( D ) TOPOLOGY: linear ( i i ) MOLECULE TYPE: peptide ( i x ) FEATURE:
    ( A ) NAME/KEY: Region
    ( B ) LOCATION: 1
    ( D ) OTHER INFORMATION: /note="N-terminal Phe is acetylated."

( i x ) FEATURE:
    ( A ) NAME/KEY: Region
    ( B ) LOCATION: 10
    ( D ) OTHER INFORMATION: /note="Xaa is Azetidine."

( i x ) FEATURE:
    ( A ) NAME/KEY: Region
    ( B ) LOCATION: 11
    ( D ) OTHER INFORMATION: /note="C-terminal p-benzoyl-L- phenylalanine is amidated."

( x i ) SEQUENCE DESCRIPTION: SEQ ID NO:361:

Phe Glu Trp Thr Pro Gly Tyr Tyr Gln Xaa Xaa
1               5                   10

( 2 ) INFORMATION FOR SEQ ID NO:362:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 1
        ( D ) OTHER INFORMATION: /note="N-terminal Phe is acetylated."

( i x ) FEATURE:
        ( A ) NAME/KEY: Region
        ( B ) LOCATION: 8
        ( D ) OTHER INFORMATION: /note="Xaa is p-benzoyl-L- phenylalanine."

( i x ) FEATURE:
        ( A ) NAME/KEY: Region
        ( B ) LOCATION: 10
        ( D ) OTHER INFORMATION: /note="Xaa is Azetidine."

( i x ) FEATURE:
        ( A ) NAME/KEY: Region
        ( B ) LOCATION: 11
        ( D ) OTHER INFORMATION: /note="Xaa is tyrosinamide."

( x i ) SEQUENCE DESCRIPTION: SEQ ID NO:362:

Phe Glu Trp Thr Pro Gly Tyr Xaa Gln Xaa Xaa
1               5                   10

( 2 ) INFORMATION FOR SEQ ID NO:363:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 7
        ( D ) OTHER INFORMATION: /note="Xaa is p-benzoyl-L- phenylalanine."

( i x ) FEATURE:
    ( A ) NAME/KEY: Region
    ( B ) LOCATION: 10
    ( D ) OTHER INFORMATION: /note="Xaa is Azetidine."

( i x ) FEATURE:
    ( A ) NAME/KEY: Region
    ( B ) LOCATION: 11
    ( D ) OTHER INFORMATION: /note="Xaa is tyrosinamide."

( x i ) SEQUENCE DESCRIPTION: SEQ ID NO:363:

Phe Glu Trp Thr Pro Gly Xaa Tyr Gln Xaa Xaa
1               5                   10

( 2 ) INFORMATION FOR SEQ ID NO:364:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 1
        ( D ) OTHER INFORMATION: /note="N-terminal Phe is acetylated."

( i x ) FEATURE:
        ( A ) NAME/KEY: Region
        ( B ) LOCATION: 7
        ( D ) OTHER INFORMATION: /note="Xaa is p-benzoyl-L- phenylalanine."

( i x ) FEATURE:
        ( A ) NAME/KEY: Region
        ( B ) LOCATION: 10
        ( D ) OTHER INFORMATION: /note="Xaa is Azetidine."

( i x ) FEATURE:
        ( A ) NAME/KEY: Region
        ( B ) LOCATION: 11
        ( D ) OTHER INFORMATION: /note="Xaa is tyrosinamide."

( x i ) SEQUENCE DESCRIPTION: SEQ ID NO:364:

Phe Glu Trp Thr Pro Gly Xaa Tyr Gln Xaa Xaa
1               5                   10

( 2 ) INFORMATION FOR SEQ ID NO:365:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 1
        ( D ) OTHER INFORMATION: /note="Xaa is p-benzoyl-L- phenylalanine."

( i x ) FEATURE:
        ( A ) NAME/KEY: Region
        ( B ) LOCATION: 10
        ( D ) OTHER INFORMATION: /note="Xaa is Azetidine."

( i x ) FEATURE:
        ( A ) NAME/KEY: Region
        ( B ) LOCATION: 11
        ( D ) OTHER INFORMATION: /note="Xaa is tyrosinamide."

( x i ) SEQUENCE DESCRIPTION: SEQ ID NO:365:

Xaa Glu Trp Thr Pro Gly Tyr Tyr Gln Xaa Xaa
1               5                   10

( 2 ) INFORMATION FOR SEQ ID NO:366:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 1
        ( D ) OTHER INFORMATION: /note="Xaa is acetylated p-benzoyl-L- phenylalanine."

( i x ) FEATURE:
        ( A ) NAME/KEY: Region
        ( B ) LOCATION: 10
        ( D ) OTHER INFORMATION: /note="Xaa is Azetidine."

( i x ) FEATURE:
        ( A ) NAME/KEY: Region
        ( B ) LOCATION: 11
        ( D ) OTHER INFORMATION: /note="Xaa is tyrosinamide."

( x i ) SEQUENCE DESCRIPTION: SEQ ID NO:366:

Xaa Glu Trp Thr Pro Gly Tyr Tyr Gln Xaa Xaa
1               5                   10

( 2 ) INFORMATION FOR SEQ ID NO:367:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 1
        ( D ) OTHER INFORMATION: /note="Xaa is 1-naphthylalanine."

( i x ) FEATURE:
        ( A ) NAME/KEY: Region
        ( B ) LOCATION: 10
        ( D ) OTHER INFORMATION: /note="Xaa is Azetidine."

( i x ) FEATURE:
        ( A ) NAME/KEY: Region
        ( B ) LOCATION: 11
        ( D ) OTHER INFORMATION: /note="Xaa is tyrosinamide."

( x i ) SEQUENCE DESCRIPTION: SEQ ID NO:367:

Xaa Glu Trp Thr Pro Gly Tyr Tyr Gln Xaa Xaa
1               5                   10

( 2 ) INFORMATION FOR SEQ ID NO:368:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:

(A) NAME/KEY: Region
(B) LOCATION: 10
(D) OTHER INFORMATION: /note="Xaa is Azetidine."

(ix) FEATURE:
(A) NAME/KEY: Region
(B) LOCATION: 11
(D) OTHER INFORMATION: /note="Xaa is tyrosinamide."

(xi) SEQUENCE DESCRIPTION: SEQ ID NO:368:

Tyr Glu Trp Thr Pro Gly Tyr Tyr Gln Xaa Xaa
1               5                   10

(2) INFORMATION FOR SEQ ID NO:369:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (ix) FEATURE:
(A) NAME/KEY: Region
(B) LOCATION: 10
(D) OTHER INFORMATION: /note="Xaa is Azetidine."

(ix) FEATURE:
(A) NAME/KEY: Region
(B) LOCATION: 11
(D) OTHER INFORMATION: /note="Xaa is tyrosinamide."

(xi) SEQUENCE DESCRIPTION: SEQ ID NO:369:

Phe Glu Trp Val Pro Gly Tyr Tyr Gln Xaa Xaa
1               5                   10

(2) INFORMATION FOR SEQ ID NO:370:

(i) SEQUENCE CHARACTERISTICS:
(A) LENGTH: 21 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:370:

Gln Gly Trp Leu Thr Trp Gln Asp Ser Val Asp Met Tyr Trp Gln Pro
1               5                   10                  15
Tyr Ala Leu Pro Leu
            20

(2) INFORMATION FOR SEQ ID NO:371:

(i) SEQUENCE CHARACTERISTICS:
(A) LENGTH: 21 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:371:

Phe Ser Glu Ala Gly Tyr Thr Trp Pro Glu Asn Thr Tyr Trp Gln Pro
1               5                   10                  15
Tyr Ala Leu Pro Leu
            20

(2) INFORMATION FOR SEQ ID NO:372:

( i ) SEQUENCE CHARACTERISTICS:
  ( A ) LENGTH: 21 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:372:

Thr Glu Ser Pro Gly Gly Leu Asp Trp Ala Lys Ile Tyr Trp Gln Pro
1               5                   10                  15

Tyr Ala Leu Pro Leu
            20

( 2 ) INFORMATION FOR SEQ ID NO:373:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:373:

Gln Pro Tyr Ala Leu Pro Leu
1               5

( 2 ) INFORMATION FOR SEQ ID NO:374:

( i ) SEQUENCE CHARACTERISTICS:
    ( A ) LENGTH: 21 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:374:

Thr Ala Asn Val Ser Ser Phe Glu Trp Thr Pro Gly Tyr Trp Gln Pro
1               5                   10                  15

Tyr Ala Leu Pro Leu
            20

( 2 ) INFORMATION FOR SEQ ID NO:375:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Region
    ( B ) LOCATION: 10
    ( D ) OTHER INFORMATION: /note="Xaa is azetidine."

( x i ) SEQUENCE DESCRIPTION: SEQ ID NO:375:

Xaa Xaa Xaa Xaa Pro Gly Tyr Tyr Gln Xaa Tyr
1               5                   10

( 2 ) INFORMATION FOR SEQ ID NO:376:

( i ) SEQUENCE CHARACTERISTICS:
    ( A ) LENGTH: 11 amino acids
    ( B ) TYPE: amino acid
    ( C ) STRANDEDNESS: single ( D ) TOPOLOGY: linear ( i i ) MOLECULE TYPE: peptide ( i x ) FEATURE:
( A ) NAME/KEY: Region
( B ) LOCATION: 3
( D ) OTHER INFORMATION: /note="Xaa is p-benzoyl-L- phenylalanine."

( i x ) FEATURE:
( A ) NAME/KEY: Region
( B ) LOCATION: 10
( D ) OTHER INFORMATION: /note="Xaa is Azetidine."

( i x ) FEATURE:
( A ) NAME/KEY: Region
( B ) LOCATION: 11
( D ) OTHER INFORMATION: /note="Xaa is tyrosinamide."

( x i ) SEQUENCE DESCRIPTION: SEQ ID NO:376:

```
Phe Glu Xaa Thr Pro Gly Tyr Tyr Gln Xaa Xaa
1               5                   10
```

( 2 ) INFORMATION FOR SEQ ID NO:377:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Region
( B ) LOCATION: 1
( D ) OTHER INFORMATION: /note="N-terminal Phe is acetylated."

( i x ) FEATURE:
( A ) NAME/KEY: Region
( B ) LOCATION: 3
( D ) OTHER INFORMATION: /note="Xaa is p-benzoyl-L- phenylalanine."

( i x ) FEATURE:
( A ) NAME/KEY: Region
( B ) LOCATION: 10
( D ) OTHER INFORMATION: /note="Xaa is Azetidine."

( i x ) FEATURE:
( A ) NAME/KEY: Region
( B ) LOCATION: 11
( D ) OTHER INFORMATION: /note="Xaa is tyrosinamide."

( x i ) SEQUENCE DESCRIPTION: SEQ ID NO:377:

```
Phe Glu Xaa Thr Pro Gly Tyr Tyr Gln Xaa Xaa
1               5                   10
```

( 2 ) INFORMATION FOR SEQ ID NO:378:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Region
( B ) LOCATION: 1
( D ) OTHER INFORMATION: /note="Xaa is p-benzoyl-L- phenylalanine."

```
( i x ) FEATURE:
        ( A ) NAME/KEY: Region
        ( B ) LOCATION: 10
        ( D ) OTHER INFORMATION: /note="Xaa is Azetidine."

( i x ) FEATURE:
        ( A ) NAME/KEY: Region
        ( B ) LOCATION: 11
        ( D ) OTHER INFORMATION: /note="Xaa is tyrosinamide."

( x i ) SEQUENCE DESCRIPTION: SEQ ID NO:378:

Xaa  Glu  Trp  Thr  Pro  Gly  Tyr  Tyr  Gln  Xaa  Xaa
 1                    5                      10
```

( 2 ) INFORMATION FOR SEQ ID NO:379:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 1
        ( D ) OTHER INFORMATION: /note="Xaa is acetylated p-
                benzoyl-L- phenylalanine."

( i x ) FEATURE:
        ( A ) NAME/KEY: Region
        ( B ) LOCATION: 10
        ( D ) OTHER INFORMATION: /note="Xaa is Azetidine."

( i x ) FEATURE:
        ( A ) NAME/KEY: Region
        ( B ) LOCATION: 11
        ( D ) OTHER INFORMATION: /note="Xaa is tyrosinamide."

( x i ) SEQUENCE DESCRIPTION: SEQ ID NO:379:

```
Xaa  Glu  Trp  Thr  Pro  Gly  Tyr  Tyr  Gln  Xaa  Xaa
 1                    5                      10
```

( 2 ) INFORMATION FOR SEQ ID NO:380:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 7
        ( D ) OTHER INFORMATION: /note="Xaa is p-
                benzoyl-L- phenylalanine."

( i x ) FEATURE:
        ( A ) NAME/KEY: Region
        ( B ) LOCATION: 10
        ( D ) OTHER INFORMATION: /note="Xaa is Azetidine."

( i x ) FEATURE:
        ( A ) NAME/KEY: Region
        ( B ) LOCATION: 11
        ( D ) OTHER INFORMATION: /note="Xaa is tyrosinamide."

( x i ) SEQUENCE DESCRIPTION: SEQ ID NO:380:

```
Phe  Glu  Trp  Thr  Pro  Gly  Xaa  Tyr  Gln  Xaa  Xaa
 1                    5                      10
```

( 2 ) INFORMATION FOR SEQ ID NO:381:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 1
        ( D ) OTHER INFORMATION: /note="N-terminal Phe is
            acetylated."

( i x ) FEATURE:
        ( A ) NAME/KEY: Region
        ( B ) LOCATION: 7
        ( D ) OTHER INFORMATION: /note="Xaa is p-
            benzoyl-L- phenylalanine."

( i x ) FEATURE:
        ( A ) NAME/KEY: Region
        ( B ) LOCATION: 10
        ( D ) OTHER INFORMATION: /note="Xaa is Azetidine."

( i x ) FEATURE:
        ( A ) NAME/KEY: Region
        ( B ) LOCATION: 11
        ( D ) OTHER INFORMATION: /note="Xaa is tyrosinamide."

( x i ) SEQUENCE DESCRIPTION: SEQ ID NO:381:

```
Phe Glu Trp Thr Pro Gly Xaa Tyr Gln Xaa Xaa
1               5                   10
```

( 2 ) INFORMATION FOR SEQ ID NO:382:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:382:

```
Xaa Xaa Xaa Xaa Asp Asn Thr Ala Trp Tyr Glu Ser Phe Leu Leu Xaa
1               5                   10                  15
Xaa
```

( 2 ) INFORMATION FOR SEQ ID NO:383:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:383:

```
Pro Ala Arg Glu Asp Asn Thr Ala Trp Tyr Asp Ser Phe Leu Ile Trp
1               5                   10                  15
Cys
```

( 2 ) INFORMATION FOR SEQ ID NO:384:

( i ) SEQUENCE CHARACTERISTICS:
        ( A ) LENGTH: 17 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO:384:

Thr Ser Glu Tyr Asp Asn Thr Thr Trp Tyr Glu Lys Phe Leu Ala Ser
1               5                   10                  15

Gln (2) INFORMATION FOR SEQ ID NO:385:

(i) SEQUENCE CHARACTERISTICS:
      (A) LENGTH: 17 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:385:

Ser Gln Ile Pro Asp Asn Thr Ala Trp Tyr Gln Ser Phe Leu Leu His
1               5                   10                  15

Gly (2) INFORMATION FOR SEQ ID NO:386:

(i) SEQUENCE CHARACTERISTICS:
      (A) LENGTH: 17 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:386:

Ser Pro Phe Ile Asp Asn Thr Ala Trp Tyr Glu Asn Phe Leu Leu Thr
1               5                   10                  15

Tyr (2) INFORMATION FOR SEQ ID NO:387:

(i) SEQUENCE CHARACTERISTICS:
      (A) LENGTH: 17 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:387:

Glu Gln Ile Tyr Asp Asn Thr Ala Trp Tyr Asp His Phe Leu Leu Ser
1               5                   10                  15

Tyr (2) INFORMATION FOR SEQ ID NO:388:

(i) SEQUENCE CHARACTERISTICS:
      (A) LENGTH: 17 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:388:

Thr Pro Phe Ile Asp Asn Thr Ala Trp Tyr Glu Asn Phe Leu Leu Thr
1               5                   10                  15

Tyr (2) INFORMATION FOR SEQ ID NO:389:

(i) SEQUENCE CHARACTERISTICS:
    (A) LENGTH: 17 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:389:

```
Thr Tyr Thr Tyr Asp Asn Thr Ala Trp Tyr Glu Arg Phe Leu Met Ser
1               5                   10                  15
Tyr
```

(2) INFORMATION FOR SEQ ID NO:390:

(i) SEQUENCE CHARACTERISTICS:
    (A) LENGTH: 17 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:390:

```
Thr Met Thr Gln Asp Asn Thr Ala Trp Tyr Glu Asn Phe Leu Leu Ser
1               5                   10                  15
Tyr
```

(2) INFORMATION FOR SEQ ID NO:391:

(i) SEQUENCE CHARACTERISTICS:
    (A) LENGTH: 17 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:391:

```
Xaa Xaa Asp Asn Thr Ala Trp Tyr Glu Ser Phe Leu Leu Xaa Xaa Xaa
1               5                   10                  15
Xaa
```

(2) INFORMATION FOR SEQ ID NO:392:

(i) SEQUENCE CHARACTERISTICS:
    (A) LENGTH: 17 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:392:

```
Thr Ile Asp Asn Thr Ala Trp Tyr Ala Asn Leu Val Gln Thr Tyr Pro
1               5                   10                  15
Gln
```

(2) INFORMATION FOR SEQ ID NO:393:

(i) SEQUENCE CHARACTERISTICS:
    (A) LENGTH: 17 amino acids ( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:393:

Thr Ile Asp Asn Thr Ala Trp Tyr Glu Arg Phe Leu Ala Gln Tyr Pro
1               5                   10                  15
Asp ( 2 ) INFORMATION FOR SEQ ID NO:394:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:394:

His Ile Asp Asn Thr Ala Trp Tyr Glu Asn Phe Leu Leu Thr Tyr Thr
1               5                   10                  15
Pro ( 2 ) INFORMATION FOR SEQ ID NO:395:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:395:

Ser Gln Asp Asn Thr Ala Trp Tyr Glu Asn Phe Leu Leu Ser Tyr Lys
1               5                   10                  15
Ala ( 2 ) INFORMATION FOR SEQ ID NO:396:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:396:

Gln Ile Asp Asn Thr Ala Trp Tyr Glu Arg Phe Leu Leu Gln Tyr Asn
1               5                   10                  15
Ala ( 2 ) INFORMATION FOR SEQ ID NO:397:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:397:

```
         Asn  Gln  Asp  Asn  Thr  Ala  Trp  Tyr  Glu  Ser  Phe  Leu  Leu  Gln  Tyr  Asn
         1              5                        10                       15

Thr
```

( 2 ) INFORMATION FOR SEQ ID NO:398:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:398:

```
         Thr  Ile  Asp  Asn  Thr  Ala  Trp  Tyr  Glu  Asn  Phe  Leu  Leu  Asn  His  Asn
         1              5                        10                       15

Leu
```

( 2 ) INFORMATION FOR SEQ ID NO:399:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:399:

```
         His  Tyr  Asp  Asn  Thr  Ala  Trp  Tyr  Glu  Arg  Phe  Leu  Gln  Gln  Gly  Trp
         1              5                        10                       15

His
```

( 2 ) INFORMATION FOR SEQ ID NO:400:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 10
        ( D ) OTHER INFORMATION: /note="Xaa is azetidine."

( x i ) SEQUENCE DESCRIPTION: SEQ ID NO:400:

```
         Phe  Glu  Trp  Thr  Pro  Gly  Trp  Tyr  Gln  Xaa  Tyr  Ala  Leu  Pro  Leu
         1              5                        10                       15
```

( 2 ) INFORMATION FOR SEQ ID NO:401:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(1, 2, 7, 8)
        ( D ) OTHER INFORMATION: /note="Xaa is any amino acid."

( i x ) FEATURE:
        ( A ) NAME/KEY: Region ( B ) LOCATION: 4
                    ( D ) OTHER INFORMATION: /note="Xaa is Pro or Azetidine."

( i x ) FEATURE:
                    ( A ) NAME/KEY: Region
                    ( B ) LOCATION: 6
                    ( D ) OTHER INFORMATION: /note="Xaa is Ser, Ala, Val or Leu."

( x i ) SEQUENCE DESCRIPTION: SEQ ID NO:401:

Xaa Xaa Gln Xaa Tyr Xaa Xaa Xaa
1               5

( 2 ) INFORMATION FOR SEQ ID NO:402:

( i ) SEQUENCE CHARACTERISTICS:
                    ( A ) LENGTH: 15 amino acids
                    ( B ) TYPE: amino acid
                    ( C ) STRANDEDNESS: single
                    ( D ) TOPOLOGY: linear ( i i ) MOLECULE TYPE: peptide ( x i ) SEQUENCE DESCRIPTION: SEQ ID NO:402:

Phe Glu Trp Thr Pro Gly Trp Tyr Gln Pro Tyr Ala Leu Pro Leu
1               5                   10                  15

( 2 ) INFORMATION FOR SEQ ID NO:403:

( i ) SEQUENCE CHARACTERISTICS:
                    ( A ) LENGTH: 15 amino acids
                    ( B ) TYPE: amino acid
                    ( C ) STRANDEDNESS: single
                    ( D ) TOPOLOGY: linear ( i i ) MOLECULE TYPE: peptide ( x i ) SEQUENCE DESCRIPTION: SEQ ID NO:403:

Phe Glu Trp Thr Pro Gly Tyr Tyr Gln Pro Tyr Ala Leu Pro Leu
1               5                   10                  15

( 2 ) INFORMATION FOR SEQ ID NO:404:

( i ) SEQUENCE CHARACTERISTICS:
                    ( A ) LENGTH: 14 amino acids
                    ( B ) TYPE: amino acid
                    ( C ) STRANDEDNESS: single
                    ( D ) TOPOLOGY: linear ( i i ) MOLECULE TYPE: peptide ( i x ) FEATURE:
                    ( A ) NAME/KEY: Region
                    ( B ) LOCATION: 13
                    ( D ) OTHER INFORMATION: /note="Xaa is Azetidine."

( i x ) FEATURE:
                    ( A ) NAME/KEY: Region
                    ( B ) LOCATION: 14
                    ( D ) OTHER INFORMATION: /note="Xaa is amidated p-
                            benzoyl-L- phenylalanine."."

( x i ) SEQUENCE DESCRIPTION: SEQ ID NO:404:

Phe Glu Trp Thr Pro Gly Tyr Tyr Gly Tyr Tyr Gln Xaa Xaa
1               5                   10

( 2 ) INFORMATION FOR SEQ ID NO:405:

( i ) SEQUENCE CHARACTERISTICS:
                    ( A ) LENGTH: 11 amino acids
                    ( B ) TYPE: amino acid
                    ( C ) STRANDEDNESS: single
                    ( D ) TOPOLOGY: linear (i i) MOLECULE TYPE: peptide (i x) FEATURE:
(A) NAME/KEY: Region
(B) LOCATION: 10
(D) OTHER INFORMATION: /note="Xaa is Azetidine."

(x i) SEQUENCE DESCRIPTION: SEQ ID NO:405:

| Phe | Glu | Trp | Thr | Pro | Gly | Tyr | Tyr | Gln | Xaa | Tyr |
|-----|-----|-----|-----|-----|-----|-----|-----|-----|-----|-----|
| 1   |     |     |     | 5   |     |     |     |     | 10  |     |

PEPTIDES AND COMPOUNDS THAT BIND TO THE IL-1 RECEPTOR

CROSS-REFERENCE

This application is a continuation-in-part of U.S. patent application No. 08/383,474, filed Feb. 1, 1995, which is a continuation-in-part of U.S. patent application No. 08/190,788, filed on Feb. 2, 1994, now U.S. Pat. No. 5,608,035 each of which is incorporated herein by reference for all purposes.

BACKGROUND OF THE INVENTION

The present invention provides peptides and compounds that bind the interleukin 1 receptor (IL-1R), methods for assaying interleukin 1 (IL-1), and methods for inhibiting the binding of IL-1 to the IL-1R. The invention has application in the fields of biochemistry and medicinal chemistry and particularly provides IL-1 antagonists for use in the treatment of human disease.

IL-1 is a polypeptide hormone, a cytokine, that exists in various forms, the genes for two of which, IL-1α and IL-1β, have been cloned. Unless otherwise noted, "IL-1" refers to either or both IL-1α and IL-1β. These two genes are both located in chromosome 2; each gene contains 7 exons, and the two genes are homologous in a region of the sixth exon. Both IL-1α and IL-1β initially exist as 31 kD precursors but are processed by proteases to produce the amino terminus of the 17.5 kD mature proteins. Receptors for IL-1 recognize the α and β forms, and both forms have similar biological properties. See Dinarello (1991) *Blood* 77(8):1627–1652, incorporated herein by reference.

The biological properties of IL-1 include mediating many immunological and inflammatory responses to infection and tissue injury. Because of the role of IL-1 in these important processes, the therapeutic benefits of IL-1 and derivatives of IL-1 have been extensively studied. See U.S. Pat. Nos. 5,075,288 and 5,077,219, incorporated herein by reference. Inappropriate production or response to IL-1 plays a role in many chronic inflammatory diseases, such as rheumatoid arthritis, osteoarthritis, psoriasis, inflammatory bowel disease, encephalitis, glomerulonephritis, and respiratory distress syndrome. See Bender and Lee (1989) *Ann. Rep. Med. Chem.* 25:185–193; and U.S. Pat. No. 5,075,222, particularly columns 1 to 3, each of which is incorporated herein by reference.

Because of the important biological properties of IL-1, IL-1 inhibitors have been extensively studied, as reviewed in Larrick (1989) *Immunol. Today* 10 (2):61–66, incorporated herein by reference. IL-1 inhibitors include the naturally occurring IL-1ra protein and soluble IL-1 receptor, as well as derivatives of IL-1α and IL-1β produced by recombinant DNA technology, as discussed in Dinarello, supra. See also PCT patent publication Nos. 91/08285, published Jun. 13, 1991, and 91/02127, published Nov. 14, 1991, incorporated herein by reference.

In similar fashion, scientists have studied the IL-1R, as reviewed in Dower and Urdal (1987) *Immunol. Today* 8(2):46–51, incorporated herein by reference. Two distinct naturally occurring types of the IL-1R are known to exist, and the corresponding genes have been cloned and expressed, as reported in Dower et al., (1990) *J. Clin. Immunol.* 10 (6):289–299; PCT patent publication No. 91/00742; U.S. Pat. No. 4,968,607, and McMahon et al.,(1991) *EMBO J.* 10(10):2821–2832, each of which is incorporated herein by reference. The type I receptor (IL-1RtI) is 80 kD in size, while the type II receptor (IL-1RtII) is 60 kD in size. A number of studies regarding whether IL-1RtI and IL-1RtII have different affinities for ligands have been conducted; see Slack et al. (1993) *J. Biol. Chem.* 268:2513–2524 and Hannum et al., (1990) *Nature* 343:336–340.

The availability of cloned genes for IL-1RtI and IL1RtII, including a soluble IL-1RtI derivative, facilitates the search for agonists and antagonists of these important receptors. The availability of the recombinant receptor protein allows the study of receptor-ligand interaction in a variety of random and semi-random peptide diversity generation systems. These systems include the "peptides on plasmids" system described in U.S. Pat. No. 5,270,170, the "peptides on phage" system described in U.S. patent application Ser. No. 718,577, filed Jun. 20, 1991, and in Cwirla et al., (1990) *Proc. Natl. Acad. Sci. USA* 87:6378–6382, and the "very large scale immobilized polymer synthesis" system described in U.S. Pat. No. 5,143,854; PCT patent publication No. 90/15070, published Dec. 13, 1990; U.S. patent application Ser. No. 624,120, filed Dec. 6, 1990; Fodor et al., Feb. 15, 1991, *Science* 251:767–773; Dower and Fodor (1991) *Ann. Rep. Med. Chem.* 26 :271–180; and U.S. patent application Ser. No. 805,727, filed Dec. 6, 1991; each of the foregoing patent applications and publications is incorporated herein by reference.

There remains a need, however, for compounds that bind to or otherwise interact with the IL-1R, both for studies of the important biological activities mediated by this receptor and for treatment of disease. The present invention provides such compounds.

SUMMARY OF THE INVENTION

In one embodiment, the invention provides compounds that bind to IL-1RtI. These compounds generally comprise a molecular weight less than about 3000 Daltons, a binding affinity to an interleukin type I receptor as expressed by an IC50 standard of no more than about 2.5 mM. Further, the binding of the compound to the IL-1 receptor is competitively inhibited by a second compound having from seven to forty amino acids in length, which comprises a core sequence of amino acids XXQZ$_5$YZ$_6$XX where X can be selected from any one of the 20 genetically coded L-amino acids; Z$_5$ is P or Aze where Aze is azetidine; and Z$_6$ is S, A, V, or L (SEQ ID NO:6); or a sequence of amino acids WXXXGZ$_1$W where each amino acid is indicated by standard one letter abbreviation; each X can be selected from any one of the 20 genetically coded L-amino acids; and Z$_1$ is L, I, A, or Q (SEQ ID NO:1). In an alternative embodiment, the binding of the compound to the IL-1 type I receptor is competitively inhibited by a compound of 11 to 40 amino acids in length that binds to the interleukin-1 type I receptor and comprises a core sequence of amino acids Z$_{23}$NZ$_{24}$Z$_{39}$Z$_{25}$Z$_{26}$Z$_{27}$Z$_{28}$Z$_{29}$Z$_{30}$Z$_{40}$, where Z$_{23}$ is D or Y; Z$_{24}$ is D, S or T; Z$_{39}$ is S, T or A; Z$_{25}$ is S or W; Z$_{26}$ is S or Y; Z$_{27}$ is D, Q, E or V; Z$_{28}$ is N, S, K, H or W; Z$_{29}$ is F or L; Z$_{30}$ is D, N, S or L; and Z$_{40}$ is L, I, Q, M or A (SEQ ID NO:16).

In a further embodiment, peptides are seven to forty or more amino acid residues in length, preferably seven to twenty-five amino acid residues in length, and comprise a core sequence of amino acids WXXXGZ$_1$W where each amino acid is indicated by the standard one letter abbreviation; each X can be selected from any one of the 20 genetically coded L-amino acids or the stereoisomeric D-amino acids; and Z$_1$ is L, I, A, or Q (SEQ ID NO:1). More preferably, the core sequence of amino acids will comprise WZ$_2$XXGZ$_1$W where X can be selected from any one of the 20 genetically coded L-amino acids; Z$_1$ is L, I, A, or Q; and $Z_2$ is D, G, N, S, or T (SEQ ID NO:2). In a more preferred embodiment, the core sequence of amino acids will comprise $WZ_2Z_3Z_4GZ_1W$ where $Z_1$ is L, I, A, or Q; $Z_2$ is D, G, N, S, or T; $Z_3$, is D, E, H, M, N, Q, R, S, T, or V; and $Z_4$ is A, D, F, H, K, N, Q, R, T, or Y (SEQ ID NO:3). Most preferably, the core sequence of amino acids comprise $WZ_2Z_3Z_4GZ_1W$ where $Z_1$ is L or I; $Z_2$ is D, S, or T; $Z_3$ is D, E, or T; and $Z_4$ is D, H, N, R, or T (SEQ ID NO:4). An especially preferred embodiment is one having the substitution patterns just described, but comprising 8, 10, or 12 amino acid residues. An especially preferred peptide has the sequence SWDTRGLWVE (SEQ ID NO:5).

According to another embodiment, the peptides are eight to forty or more amino acid residues in length, preferably eight to twenty-five amino acid residues in length, and comprise a core sequence of amino acids $XXQZ_5YZ_6XX$ where X can be selected from any one of the 20 genetically coded L-amino acids or the stereoisomeric D-amino acids or unnatural amino acids; $Z_5$ is P or Aze where Aze (or J) is azetidine; and $Z_6$ is S, A, V, or L (SEQ ID NO:6). More preferably, the sequence of amino acids will comprise $Z_7XQZ_5YZ_6XX$ where X can be selected from any one of the 20 genetically coded L-amino acids; $Z_5$ is P or J; $Z_6$ is S, A, V, or L; and $Z_7$ is Y, W, or F (SEQ ID NO:7). In a more preferred embodiment, the core sequence of amino acids will comprise $Z_7Z_8QZ_5YZ_6Z_9Z_{10}$ where $Z_5$ is P or Aze where Aze is azetidine; $Z_6$ is S, A, V, or L; $Z_7$ is Y, W, or F; $Z_8$ is E, F, V, W, or Y; $Z_9$ is M, F, V, R, Q, K, T, S, D, L, I, or E; and $Z_{10}$ is E, L, W, V, H, I, G, A, D, L, Y, N, Q or P (SEQ ID NO:8). More preferably, $Z_9$ is V, L, I, or E; and $Z_{10}$ is Q or P. Most preferably, the core peptide will comprise a sequence of amino acids $Z_{11}Z_7Z_8QZ_5YZ_6Z_9Z_{10}$, where $Z_8$ is Y, W or F; and $Z_{11}$ is V, L, I, E, P, G, Y, M, T, or, D (SEQ ID NO:9).

Preferred peptides include FEWTPGYWQPYALPL (SEQ ID NO:331), FEWTPGYWQJYALPL (SEQ ID NO:356), FEWTPGWYQPYALPL (SEQ ID NO:402), FEWTPGWYQJYALPL (SEQ ID NO:400), FEWTPGYYQPYALPL (SEQ ID NO:403) and FEWTPGYYQJYALPL (SEQ ID NO:358).

An especially preferred embodiment is one having the substitution patterns just described, but comprising 21 amino acid residues. Particularly preferred is the peptide comprising the sequence of amino acids $Z_{12}Z_{13}Z_{14}Z_{15}Z_{16}Z_{17}Z_{18}Z_{19}Z_{20}Z_{21}Z_{22}Z_{11}Z_7Z_8QZ_5YZ_6Z_9Z_{10}L$, where $Z_8$ is Y, W or F; $Z_{11}$ is V, L, I, E, P, G, Y, M, T, or, D; $Z_{12}$ is A, D, E, F, G, K, Q, S, T, V, or Y; $Z_{13}$ is A, D, G, I, N, P, S, T, V, or W; $Z_{14}$ is A, D, G, L, N, P, S, T, W, or Y; $Z_{15}$ is A, D, E, F, L, N, R, V, or Y; $Z_{16}$ is A, D, E, Q, R, S, or T; $Z_{17}$ is H, I, L, P, S, T, or, W; $Z_{18}$ is A, E, F, K, N, Q, R, S, or Y; $Z_{19}$ is D, E, F, Q, R, T, or W; $Z_{20}$ is A, D, P, S, T, or W; $Z_{21}$ is A, D, G, K, N, Q, S, or T; and $Z_{22}$ is A, E, L, P, S, T, V or Y (SEQ ID NO:10). More preferably, $Z_8$ is Y, W or F; $Z_{11}$, is V, L, I, E, P, G, Y, M, T, or, D; $Z_{12}$ is D, E, Q, S, T, V, or Y; $Z_{13}$ is A, D, G, I, N, S, T or V; $Z_{14}$ is A, G, L, N, P, S, T, or Y; $Z_{15}$ is D, E, F, L, V, or Y; $Z_{16}$ is D, R, S or T; $Z_{17}$ is H, P, S, or W; $Z_{18}$ is E, F, N, R, Q, or S; $Z_{19}$ is D, E, F, Q, or W; $Z_{20}$ is S, T, or W; $Z_{21}$ is D, G, K, N, Q, S, or T; and $Z_{22}$ is A, E, P, S, or Y (SEQ ID NO:298).

Particularly preferred peptides include TANVSSFEWTPGYWQPYALPL (SEQ ID NO:11); SWTDYGYWQPY-ALPISGL (SEQ ID NO:12); ETPFTWEESNAYYWQPY-ALPL (SEQ ID NO:13); ENTYSPNWADSMYWQPYALPL (SEQ ID NO:14); SVGEDHNFWTSEYWQPYALPL (SEQ ID NO:15); and DGYDRWRQSGERYWQPYALPL (SEQ ID NO:16).

In a related embodiment, the present invention also provides peptides which bind to IL-1RtI, which are fourteen to forty or more amino acid residues in length, preferably fourteen to twenty-five amino acid residues in length, and which comprise a core amino acid sequence FTWEESNAYYWQJY-NH$_2$ (SEQ ID NO:313).

According to another embodiment, the invention provides peptides which bind to IL-1RtI, which are seven to forty or more amino acid residues in length, preferably seven to twenty-five amino acid residues in length, and which comprise a core sequence of amino acids $Z_{23}NZ_{24}SZ_{25}Z_{26}Z_{27}Z_{28}Z_{29}Z_{30}L$ where $Z_{23}$ is D or Y; $Z_{24}$ is D or S; $Z_{25}$ is S or W; $Z_{26}$ is S or Y; $Z_{27}$ is D or V; $Z_{28}$ is S or W; $Z_{29}$ is F or L; and $Z_{30}$ is D or L (SEQ ID NO:325).

A further embodiment of the present invention provides peptides which bind to the IL-1RtI, which are 11 to 40 amino acids in length, which comprise the core sequence of amino acids $Z_{31}XWZ_{32}Z_{33}Z_{34}Z_{35}Z_{36}QZ_{37}Z_{38}$, where each letter represents the standard one letter abbreviation for an amino acid or an analog thereof; X is selected from the group of natural or unnatural amino acids; $Z_{31}$ is selected from phenylalanine, acetylated phenylalanine, tyrosine, acetylated tyrosine, 1-naphthylalanine ("1Nap"), acetylated 1-naphthylalanine ("Ac1Nap"), p-benzoyl-L-phenylalanine ("Bpa") and acetylated p-benzoyl-L-phenylalanine ("AcBpa"); $Z_{32}$ is a natural or unnatural amino acid; $Z_{33}$ is selected from proline and pipecolic acid which is represented by Pec; $Z_{34}$ is selected from glycine, d-alanine, d-valine, sarcosine, and aminoisobutyric acid, represented by Sar and Aib, respectively; $Z_{35}$ is a natural or unnatural amino acid; $Z_{36}$ is selected from tyrosine, phosphotyrosine, phenylalanine, tryptophan, 1-naphthylalanine and p-benzoyl-L-phenylalanine; $Z_{37}$ is selected from proline or azetidine, represented as J; and $Z_{38}$ is selected from tyrosine, tyrosinamide, substituted tyrosinamide and p-benzoyl-L-phenylalanine.

More preferred are those peptides wherein $Z_{32}$ is selected from alanine, threonine and valine; and $Z_{35}$ and $Z_{36}$ are selected independently from the group consisting of tyrosine, phosphotyrosine, phenylalanine, tryptophan, 1-naphthylalanine and p-benzoyl-L-phenylalanine.

Particularly preferred peptides are those selected from the group consisting of the following peptides and amides and esters thereof: FEWTPGYWQPY-NH2 (SEQ ID NO:315); FEWTPGYWQJY-NH2 (SEQ ID NO:316); FEWTPGWYQJY-NH2 (SEQ ID NO:317); AcFEWTPGWYQJY-NH2 (SEQ ID NO:318); FEWTPGW-pY-QJY-NH2 (SEQ ID NO:319); FAWTPGYWQJY-NH2 (SEQ ID NO:320); FEWAPGYWQJY-NH2 (SEQ ID NO:321); FEWVPGYWQJY-NH2 (SEQ ID NO:322); FEWTPGYWQJY-NH2 (SEQ ID NO:323); AcFEWTPGYWQJY-NH2 (SEQ ID NO:324); FEWTPaWYQJY-NH2; FEWTP-Sar-WYQJY-NH2 (SEQ ID NO:326); FEWTPGYYQPY-NH2 (SEQ ID NO:327); FEWTPGWWQPY-NH2 (SEQ ID NO:328); FEWTPNYWQPY-NH2 (SEQ ID NO:329); FEWTPvYWQJY-NH2; FEWT-Pec-GYWQJY-NH$_2$ (SEQ ID NO:347); FEWTP-Aib-YWQJY-NH$_2$ (SEQ ID NO:348); FEWT-Sar-GYWQJY-NH$_2$ (SEQ ID NO:349); FEWTPGY-WQPYALPL (SEQ ID NO:331); FEWTPGYYQJ-Bpa-NH$_2$ (SEQ ID NO:404); AcFEWTPGYYQJ-Bpa-NH$_2$ (SEQ ID NO:361), FEWTPGY-Bpa-QJY-NH$_2$ (SEQ ID NO:360); AcFEWTPGY-Bpa-QJY-NH$_2$ (SEQ ID NO:362); FEWTPG-Bpa-YQJY-NH$_2$ (SEQ ID NO:363); AcFEWTPG-Bpa-YQJY-NH$_2$ (SEQ ID NO:364); Bpa-EWTPGYYQJY-NH$_2$ (SEQ ID NO:365); AcBpa-EWTPGYYQJY-NH$_2$ (SEQ ID NO:366); 1Nap- EWTPGYYQJY-NH2 (SEQ ID NO:367);
YEWTPGYYQJY-NH₂ (SEQ ID NO:368);
FEWVPGYYQJY-NH₂ (SEQ ID NO:369);
FEWTPsYYQJY-NH₂ and FEWTPnYYQJY-NH₂; where AcF is acetylated phenylalanine, Y-NH2 is tyrosinamide, -pY- is phosphotyrosine, -Sar- is sarcosine, -Pec- is pipecolic acid, -Aib- is aminoisobutyric acid, 1Nap is 1-naphthylalanine, Bpa is p-benzoyl-L-phenylalanine and AcBpa is acetylated p-benzoyl-L-phenylalanine.

The present invention also provides conjugates of these peptides and derivatives and peptidomimetics of the peptides that retain the property of IL-1RtI binding but, by virtue of the conjugated compound, act either as an agonist or antagonist of IL-1RtI or direct a cytotoxic or other therapeutic agent to cells that express IL-1RtI.

The compounds described herein are useful for the prevention and treatment of diseases involving improper production of or response to IL-1 utilizing the novel compounds of the invention. Thus, the present invention also provides a method of treatment, wherein a patient having a disorder that is susceptible to treatment with an IL-1 inhibitor receives, or is administered, a therapeutically effective dose or amount of a compound of the present invention.

The invention also provides for pharmaceutical compositions comprising one or more of the compounds described herein and a physiologically acceptable carrier. These pharmaceutical compositions can be in a variety of forms including oral dosage forms, as well as injectable and infusible solutions. The present invention also provides conjugates of these peptides and derivatives and peptidomimetics of the peptides that retain the property of IL-1RtI binding but, by virtue of the conjugated compound, act either as an agonist or antagonist of IL-1RtI or direct a cytotoxic or other therapeutic agent to cells that express IL-1RtI.

DESCRIPTION OF THE PREFERRED EMBODIMENT

I. Definitions and General Parameters

The following definitions are set forth to illustrate and define the meaning and scope of the various terms used to describe the invention herein.

"Pharmaceutically acceptable salts" refer to the non-toxic alkali metal, alkaline earth metal, and ammonium salts commonly used in the pharmaceutical industry including the sodium, potassium, lithium, calcium, magnesium, barium, ammonium, and protamine zinc salts, which are prepared by methods well known in the art. The term also includes non-toxic acid addition salts, which are generally prepared by reacting the compounds of this invention with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate, and the like.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like. For a description of pharmaceutically acceptable acid addition salts as prodrugs, see Bundgaard, H., ed., (1985) *Design of Prodrugs,* Elsevier Science Publishers, Amsterdam.

"Pharmaceutically acceptable ester" refers to those esters which retain, upon hydrolysis of the ester bond, the biological effectiveness and properties of the carboxylic acid or alcohol and are not biologically or otherwise undesirable. For a description of pharmaceutically acceptable esters as prodrugs, see Bundgaard, H., ed., (1985) *Design of Prodrugs,* Elsevier Science Publishers, Amsterdam. These esters are typically formed from the corresponding carboxylic acid and an alcohol. Generally, ester formation can be accomplished via conventional synthetic techniques. (See, e.g., March *Advanced Organic Chemistry,* 3rd Ed., John Wiley & Sons, New York (1985) p. 1157 and references cited therein, and Mark et al. *Encyclopedia of Chemical Technology,* John Wiley & Sons, New York (1980).) The alcohol component of the ester will generally comprise (i) a $C_2$–$C_{12}$ aliphatic alcohol that can or can not contain one or more double bonds and can or can not contain branched carbon chains or (ii) a $C_7$–$C_{12}$ aromatic or heteroaromatic alcohols. This invention also contemplates the use of those compositions which are both esters as described herein and at the same time are the pharmaceutically acceptable acid addition salts thereof.

"Pharmaceutically acceptable amide" refers to those amides which retain, upon hydrolysis of the amide bond, the biological effectiveness and properties of the carboxylic acid or amine and are not biologically or otherwise undesirable. For a description of pharmaceutically acceptable amides as prodrugs. See Bundgaard, H., supra. These amides are typically formed from the corresponding carboxylic acid and an amine. Generally, amide formation can be accomplished via conventional synthetic techniques. (See, e.g., March *Advanced Organic Chemistry,* 3rd Ed., John Wiley & Sons, New York (1985) p. 1152 and Mark et al. *Encyclopedia of Chemical Technology,* John Wiley & Sons, New York (1980).) This invention also contemplates the use of those compositions which are both amides as described herein and at the same time are the pharmaceutically acceptable acid addition salts thereof.

"Pharmaceutically or therapeutically acceptable carrier" refers to a carrier medium which does not interfere with the effectiveness of the biological activity of the active ingredients and which is not toxic to the host or patient.

"Stereoisomer" refers to a chemical compound having the same molecular weight, chemical composition, and constitution as another, but with the atoms grouped differently. That is, certain identical chemical moieties are at different orientations in space and, therefore, when pure, has the ability to rotate the plane of polarized light. However, some pure stereoisomers may have an optical rotation that is so slight that it is undetectable with present instrumentation. The compounds of the instant invention may have one or more asymmetrical carbon atoms and therefore include various stereoisomers. All stereoisomers are included within the scope of the invention.

"Therapeutically- or pharmaceutically-effective amount" as applied to the compositions of the instant invention refers to the amount of composition sufficient to induce a desired biological result. That result can be alleviation of the signs, symptoms, or causes of a disease, or any other desired alteration of a biological system. In the present invention, the result will typically involve a decrease in the immunological and/or inflammatory responses to infection or tissue injury.

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. Amino acids acetylated at the amino group will possess the prefix "Ac". Thus, acetylated phenylalanine will be represented by AcF. Similarly, carboxamide amino acids will possess the suffix "NH$_2$".

In addition to peptides consisting only of naturally-occurring amino acids, peptidomimetics or peptide analogs are also provided. Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) Adv. Drug Res. 15:29; Veber and Freidinger (1985) TINS p.392; and Evans et al. (1987) J. Med. Chem. 30:1229, which are incorporated herein by reference). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as naturally-occurring receptor-binding polypeptide, but have one or more peptide linkages optionally replaced by a linkage selected from the group consisting of: —CH$_2$NH—, —CH$_2$S—, —CH$_2$—CH$_2$—, —CH=CH— (cis and trans), —COCH$_2$—, —CH(OH)CH$_2$—, and —CH$_2$SO—, by methods known in the art and further described in the following references: Spatola, A. F. in CHEMISTRY AND BIOCHEMISTRY OF AMINO ACIDS, PEPTIDES, AND PROTEINS, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463–468 (general review); Hudson, D. et al., (1979) Int J Pept Prot Res 14:177–185 (—CH$_2$NH—, CH$_2$CH$_2$—); Spatola et al., (1986) Life Sci 38:1243–1249 (—CH$_2$—S); Hann (1982) J. Chem. Soc. Perkin Trans. I 307–314 (—CH—CH—, cis and trans); Almquist et al., (1980) J Med Chem 23:1392–1398 (—COCH$_2$—); Jennings-White et al., (1982) Tetrahedron Lett 23:2533 (—COCH$_2$—); Szelke et al., (1982) European Appln. EP 45665 CA: 97:39405 (1982) (—CH(OH)CH$_2$—); Holladay et al., (1983) Tetrahedron Lett 24:4401–4404 (—C(OH)CH$_2$—); and Hruby (1982) Life Sci 31:189–199 (—CH$_2$—S—); each of which is incorporated herein by reference. A particularly preferred non-peptide linkage is —CH$_2$NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) (e.g., immunoglobulin superfamily molecules) to which the peptidomimetic binds to produce the therapeutic effect. Derivitization (e.g., labeling) of peptidomimetics should not substantially interfere with the desired biological or pharmacological activity of the peptidomimetic. Generally, peptidomimetics of receptor-binding peptides bind to the receptor with high affinity and possess detectable biological activity (i.e., are agonistic or antagonistic to one or more receptor-mediated phenotypic changes). Abbreviations of some of the nonnatural amino acids or amino acid analogs, used herein, include "Aib" for aminoisobutyric acid, "Sar" for sarcosine, "Pec" for pipecolic acid, "1Nap" for 1-naphthylalanine, and "Bpa" for p-benzoyl-L-phenylalanine.

Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch (1992) Ann. Rev. Biochem. 61:387, incorporated herein by reference); for example, by adding internal cysteine residues capable of forming intramolecular disulfide bridges which cyclize the peptide. Such D-amino acids are abbreviated by the lower case single letter abbreviations previously described herein, e.g., where "A" represents L-alanine and "a" represents D-alanine.

II. Overview

The present invention provides compounds that bind to the IL-1RtI. These compounds include "lead" peptide compounds and "derivative" compounds constructed so as to have the same or similar molecular structure or shape as the lead compounds but that differ from the lead compounds either with respect to susceptibility to hydrolysis or proteolysis and/or with respect to other biological properties, such as increased affinity for the receptor. The present invention also provides compositions comprising an effective IL-1RtI binding, IL-1 blocking compound, and more particularly a compound, that is useful for treating disorders associated with the overexpression of IL-1.

In general, the peptides of the present invention will have strong binding properties to the Interleukin-1 type I receptor ("IL-1RtI"). Specifically, the peptides will be characterized as having a binding affinity to IL-1RtI as measured by an IC50 of about 2.5 mM or less, typically, about 100 μM or less, and preferably, 20 μM or less. Additionally, the peptides of the present invention may be relatively small. Typically, the peptides have a molecular weight of less than about 5000 kilodaltons, and preferably, less than about 3000 kilodaltons.

III. Random Peptide Diversity Generating Systems

Initial lead peptide compounds were identified using random peptide diversity generating systems including the "peptides on phage" and "peptides on plasmids" systems discussed above and described in U.S. Pat. No. 5,270,170, and co-pending U.S. application Ser. Nos. 718,577, and 07/847,567, filed Mar. 5, 1992. The random peptides were designed to be eight to twelve amino acid residues in length, and one system employed fixed cysteine residues at each end of the random peptide to facilitate the formation of cyclic peptides. To generate the collection of oligonucleotides that encode the random peptides, the codon motif (NNK)x, where N was nucleotide A, C, G, or T (equimolar; depending on the methodology employed, other nucleotides can be employed), K is G or T (equimolar), and x was 6 (for the cyclic library—the other two terminal codons were cysteine codons), 8, 10, or 12; was used in the synthesis of the oligonucleotides. Those of skill in the art will recognize that the NNK motif encodes all of the amino acids, encodes only one stop codon, and reduces codon bias. There are 32 possible codons resulting from the NNK motif: 1 for each of 12 amino acids, 2 for each of 5 amino acids, 3 for each of 3 amino acids, and only one of the three stop codons.

In these initial systems, the random peptides were presented as part of a fusion protein comprising either the pIII or pVIII coat protein of a phage fd derivative (peptides on phage) or the lac repressor DNA binding protein (peptides on plasmids). The fusion proteins, along with the DNA encoding the fusion proteins, were "panned" on immobilized IL-1RtI. The panning process involved multiple rounds of incubating the fusion proteins with the immobilized receptor, collecting the fusion proteins that bound to the receptor (along with the accompanying DNA), and amplifying the fusion proteins collected.

Typically after three rounds of panning, the fusion proteins and accompanying DNA were isolated and cultured to produce fusion protein preparations for an ELISA to determine if the fusion protein bound specifically to the receptor. This assay was carried out similarly to the panning, except that after removing unbound fusion proteins, the wells were treated with rabbit anti-phage antibody (or with anti-lac antibody for the peptides on plasmids system), then with alkaline phosphatase-conjugated goat anti-rabbit antibody, and then the amount of alkaline phosphatase in each well was determined by standard methods. By comparing test wells with control wells (no receptor), one can determine whether the fusion proteins bind to the receptor specifically. Fusion proteins found to bind specifically to the receptor were then tested in an IL-1α blocking assay. The blocking assay was carried out in similar fashion to the ELISA , except that IL-1α was added to the wells before the fusion protein (the control wells were of two types: (1) no receptor; and (2) no IL-1α). Fusion proteins for which the binding to the receptor was blocked by IL-1α contain peptides in the random peptide portion that are preferred compounds of the invention.

Several forms of the Type I IL-1 receptor were used in the panning and ELISA procedures and IC$_{50}$ determinations. For example, radiolabelled monovalent receptor was prepared by expressing soluble receptor fused with the 7 amino acid substrate sequence for protein kinase A. The receptor was then labelled using protein kinase A and $^{33}$P or $^{32}$P-ATP. See, Li, B. L., et al., Creation of phosphorylation sites in proteins: construction of a phosphorylatable human interferon alpha, Proc. Natl Acad. Sci. 86(2):558–562. Additionally, an immobilized receptor useful in the panning and ELISA procedures was produced in recombinant host cells in a truncated form comprising the complete extracellular domain (as determined by hydrophobicity studies) of IL-1RtI (amino acids 1 to 336 of the sequence reported by Chua and Gubler, 1989, Nuc. Acids Res. 17(23):10114, incorporated herein by reference). This truncated receptor molecule can be produced in a variety of different forms and host cells. One useful form of the receptor is constructed by expressing the receptor as a soluble protein in baculovirus transformed host cells using standard methods; another useful form is constructed with a signal peptide for protein secretion and for glycophospholipid membrane anchor attachment (this form of anchor attachment is called "PIG-tailing;" see Caras and Weddell (1989) Science 243:1196–1198, and Lin et al., (1990) Science 249:677–679, each of which is incorporated herein by reference). Using the latter system, one can cleave the receptor from the surface of the cells expressing the receptor and collect the cleaved receptor quite easily.

Several bivalent forms of the receptor were also prepared for use in the identification of peptides capable of interacting with the IL-1 receptor. A bivalent receptor-antibody complex was generated by mixing $^{33}$P labeled receptor with an anti-IL-1RtI antibody followed by the addition of excess unlabeled receptor. Similarly, a bivalent receptor was obtained by mixing an excess of the receptor with $^{125}$I labeled antibody, and then purifying the receptor by passing it over an Ab179 column (if one is using the PIG-tailed form of the receptor, then one can use an antibody that binds to the HPAP residue that remains attached to the receptor after secretion and cleavage). Another bivalent receptor was constructed by linking the extracellular portion of the Type I IL-1R through its C-terminus to the Fc portion of a human IgG molecule.

The recombinant receptor protein was immobilized using the following methodology. Microtiter plates were coated with an anti-IL-1RtI antibody that does not block IL-1α binding to IL-1RtI and then the wells containing the immobilized receptor were treated with bovine serum albumin (BSA) to block non-specific binding. The receptor was added to the coated wells of the microtiter plate, which were then washed to remove unbound receptor.

Often, the receptor was added only to alternate rows of the microtiter plate; the BSA-blocked wells in the "blank" rows served as useful negative controls to determine whether a receptor-specific reaction was creating the observed results. Fusion protein preparations were then added to the wells and incubated to allow binding to the receptor to occur; then, the wells were washed to remove unbound fusion proteins.

With the above systems, a number of different fusion proteins were discovered that bind to the IL-1RtI, but that binding did not appear to be blocked by IL-1α at a concentration of about 12 μM. The DNA encoding the fusion proteins that bound to the receptor was sequenced to determine the sequence of the random peptide that the fusion proteins contained. These peptides, together with similar peptides isolated using different libraries (discussed below) are shown in Table 1, below.

TABLE 1

| Fusion Protein | Random Peptide Sequence |
| --- | --- |
| R1 | WWTDTGLW (SEQ ID NO:18) |
| R11 | WWTDDGLW (SEQ ID NO:19) |
| S4 | WWDTRGLWVWTI (SEQ ID NO:20) |
| DB29 | FWGNDGIWLESG (SEQ ID NO:21) |
| S14 | DWDQFGLWRGAA (SEQ ID NO:22) |
| NU1 | RWDDNGLWVVVL (SEQ ID NO:23) |
| T11 | SGMWSHYGIWMG (SEQ ID NO:24) |
| T12 | GGRWDQAGLWVA (SEQ ID NO:25) |
| MC1 | KLWSEQGIWMGE (SEQ ID NO:26) |
| CYC1 | CWSMHGLWLC (SEQ ID NO:27) |
| F17 | GCWDNTGIWVPC (SEQ ID NO:28) |
| IL1 | DWDTRGLWVY (SEQ ID NO:29) |
| IL3 | SLWDENGAWI (SEQ ID NO:30) |
| IL4 | KWDDRGLWMH (SEQ ID NO:31) |
| IL6 | QAWNERGLWT (SEQ ID NO:32) |
| IL7 | QWDTRGLWVA (SEQ ID NO:33) |
| IL8,11E | WNVHGIWQE (SEQ ID NO:34) |
| IL9 | SWDTRGLWVE (SEQ ID NO:5) |
| IL12,17 | DWDTRGLWVA (SEQ ID NO:35) |
| IL13 | SWGRDGLWIE (SEQ ID NO:36) |
| IL16 | EWTDNGLWAL (SEQ ID NO:37) |
| IL19 | SWDEKGLWSA (SEQ ID NO:38) |
| IL20 | SWDSSGLWMD (SEQ ID NO:39) |

The peptides in Table 1 are characterized by the motif "IWXXXGZ$_1$W" where each amino acid is indicated by standard one letter abbreviation; each X can be selected from any one of the 20 genetically coded L-amino acids or the stereoisomeric D-amino acids; and $Z_1$ is L, I, A, or Q (SEQ ID NO:1). More preferably, the core sequence of amino acids will be comprise $WZ_2XXGZ_1W$ where X can be selected from any one of the 20 genetically coded L-amino acids; $Z_1$ is L, I, A, or Q; and $Z_2$ is D, G, N, S, or T (SEQ ID NO:2). In a more preferred embodiment, the core sequence of amino acids will comprise $WZ_2Z_3Z_4GZ_1W$ where $Z_1$ is L, I, A, or Q; $Z_2$ is D, G, N, S, or T; $Z_3$ is D, E, H, M, N, Q, R, S, T, or V; and $Z_4$ is A, D, F, H, K, N, Q, R, T, or Y (SEQ ID NO:3). Most preferably, the core sequence of amino acids comprise $WZ_2Z_3Z_4GZ_1W$ where $Z_1$ is L or I; $Z_2$ is D, S, or T; $Z_3$ is D, E, or T; and $Z_4$ is D, H, N, R, or T (SEQ ID NO:4). An especially preferred embodiment is one having the substitution patterns just described, but comprising 8, 10, or 12 amino acid residues. An especially preferred peptide has the sequence SWDTRGLWVE (SEQ ID NO:5). These peptides are valuable due to their ability to bind specifically with the IL-1R without blocking the IL-1α binding site on the receptor.

The peptides of the present invention can be conjugated to compounds that do bind to the IL-1α binding site of an IL-1R to construct compounds with an affinity for the IL-1R greater than either of the compounds of which the conjugate is composed. The discovery of these peptides also facilitates the identification of peptides that do bind to the same site on IL-1R as IL-1α, because one can bias the library or panning procedure to eliminate peptides with this "non-blocking" motif. For instance, one can make a library with no tryptophan residues in the random peptide or one can pan a library using receptor immobilized with an anti-IL-IR antibody that blocks binding of peptides with this motif but does not block IL-1 binding. One could also pan in the presence of high concentrations of the peptide.

Several new libraries of random peptides were constructed in a manner designed to minimize the production of fusion proteins comprising the "$WXXXGZ_1W$" (SEQ ID NO:1) motif. These libraries were characterized by the use of the codon motif "NNW," where W is nucleotide A or T, in codons two and eight in synthesizing the oligonucleotide encoding the random peptide. The resulting peptides thus did not contain a methionine (M) or a tryptophan (W) at positions two and eight of the random peptide portion of the fusion protein. Panning of these libraries yielded fusion proteins T11, T12, and F17 in Table 1, above, together with the fusion protein T6, which comprises the peptide "RLVYWQPYSVQR" (SEQ ID NO:40). Phage bearing the fusion protein T6 bound specifically to IL-1RtI, and binding of the phage was inhibited by IL-1α. The T6 peptide was synthesized on a peptide synthesizer (Example 1, below), and the synthetic free peptide was tested and found to compete with IL-1α in binding to the IL-1R at micromolar concentration (see Example 3).

A. Peptides Possessing the QPY or QPY-like Motif

The T6 peptide sequence, above, then served as the basis for the construction of another peptide library designed to contain a high frequency of derivatives of the T6 peptide. This library was synthesized so as to favor the production of peptides that differ from the T6 peptide in only a few residues. This approach involved the synthesis of an oligonucleotide with the T6 random peptide coding sequence, except that rather than using pure preparations of each of the four nucleoside triphosphates in the synthesis, mixtures of the four nucleoside triphosphates were used so as to generate derivatives of the T6 peptide coding sequence. This library was prepared and panned as above, and the peptide sequences obtained are shown in Table 2, below, together with the T6 sequence.

IC50 values are indicated symbolically by the symbols "–", "+", and "++". For example, those peptides which showed IC50 values in excess of 100 μM are indicated with a "–". Those peptides which give IC50 values of less than or equal to 100 μM are given a "+", while those which give IC50 values of 500 nM or less are indicated with a "++". Those peptides which give IC50 values at or near the cutoff point for a particular symbol are indicated with a hybrid, e.g. "+/–". Those peptides for which IC50 values were not determined are listed as "N.D".

TABLE 2

| Fusion Protein | Random Peptide Sequence | $IC_{50}$[1] |
|---|---|---|
| 2H2 | SHLYWQPYSVQ (SEQ ID NO:41) | + |
| H3 | TLVYWQPYSLQT (SEQ ID NO:42) | + |
| 3H9, 11 | RGDYWQPYSVQS (SEQ ID NO:43) | + |
| 3H5 | VHVYWQPYSVQT (SEQ ID NO:44) | + |
| 3H2 | RLVYWQPYSVQT (SEQ ID NO:45) | + |
| 3H1, 6, 12 | SRVWFQPYSLQS (SEQ ID NO:46) | + |
| 3H7 | NMVYWQPYSIQT (SEQ ID NO:47) | + |
| 3H10 | SVVFWQPYSVQT (SEQ ID NO:48) | + |
| 3H4 | TFVYWQPYALPL (SEQ ID NO:49) | + |
| 2H11 | TLVYWQPYSIQR (SEQ ID NO:50) | + |
| T6 | RLVYWQPYSVQR (SEQ ID NO:40) | + |
| D1 | SPVFWQPYSIQI (SEQ ID NO:51) | + |
| D2 | WIEWWQPYSVQS (SEQ ID NO:52) | + |
| D3 | SLIYWQPYSLQM (SEQ ID NO:53) | + |
| D13 | TRLYWQPYSVQR (SEQ ID NO:54) | + |
| D15 | RCDYWQPYSVQT (SEQ ID NO:55) | + |
| D18 | MRVFWQPYSVQN (SEQ ID NO:56) | + |
| D19 | KIVYWQPYSVQT (SEQ ID NO:57) | + |
| D20 | RHLYWQPYSVQR (SEQ ID NO:58) | + |
| 2H6 | ALVWWQPYSEQI (SEQ ID NO:59) | + |
| 3H8 | SRVWFQPYSLQS (SEQ ID NO:60) | |

[1]Unless otherwise indicated, $IC_{50}$ determinations were conducted using soluble peptide. Results marked with * were obtained using the immobilized PIG-tailed Type I IL-1R.

Table 2 shows that a general structure for these compounds is defined by $Z_7XQZ_5YZ_6XX$ where X can be selected from any one of the 20 genetically coded L-amino acids; $Z_5$ is P or Aze (or J) where Aze is azetidine; $Z_6$ is S, A V, or L; and $Z_7$ is Y, W, or F (SEQ ID NO:7)

In addition, screening of a 10-mer library on PVIII in the presence of a known blocking peptide, SWDTRGLWVE (SEQ ID NO:) resulted in the identification of the following peptides:

TABLE 3

| Peptide | $IC_{50}$ |
|---|---|
| WEQPYALPLE (SEQ ID NO:61) | + |
| REYEQPYALW (SEQ ID NO:62) | – |
| EEWAQPYAFL (SEQ ID NO:63) | – |
| GSWEQPYAMV (SEQ ID NO:64) | – |
| AWYGPSNLPV (SEQ ID NO:65) | – |

The results of screening of various other libraries (for example, 70:10:10:10; fixed-sliding libraries and extended/mutagenized libraries which were screened using standard elution conditions and tested under standard or low receptor density conditions) are shown below:

TABLE 4

Library Based on RLVYWQPYSVQR (SEQ ID NO:299) with 50% NNK

| Peptide | IC$_{50}$ |
|---|---|
| QLVWWQPYSVQR (SEQ ID NO:66) | + |
| DLRYWQPYSVQV (SEQ ID NO:67) | + |
| ELVWWQPYSLQL (SEQ ID NO:68) | + |
| DLVWWQPYSVQW (SEQ ID NO:69) | + |
| NGNYWQPYSFQV (SEQ ID NO:70) | + |
| ELVYWQPYSIQR (SEQ ID NO:71) | + |
| WSNYWQPYSVQP (SEQ ID NO:72) | +/− |
| QYVYWQPLSVQV (SEQ ID NO:73) | − |
| ELMYWQPYSVQE (SEQ ID NO:74) | N.D. |
| NLLYWQPYSMQD (SEQ ID NO:75) | N.D. |

TABLE 5

Library Based on XXXXXXPYSVQR (SEQ ID NO:300)

| Peptide | IC$_{50}$ |
|---|---|
| GYEWYQPYSVQR (SEQ ID NO:76) | + |
| SRVWYQPYSVQR (SEQ ID NO:77) | + |
| LSEQYQPYSVQR (SEQ ID NO:78) | + |
| GGGWWQPYSVQR (SEQ ID NO:79) | + |
| VGRWYQPYSVQR (SEQ ID NO:80) | + |
| VHVYWQPYSVQR (SEQ ID NO:81) | + |
| QARWYQPYSVQR (SEQ ID NO:82) | + |
| VHVYWQPYSVQT (SEQ ID NO:83) | + |
| RSVYWQPYSVQR (SEQ ID NO:84) | + |
| TRVWFQPYSVQR (SEQ ID NO:85) | + |
| GRIWFQPYSVQR (SEQ ID NO:86) | + |
| GRVWFQPYSVQR (SEQ ID NO:87) | + |
| ARTWYQPYSVQR (SEQ ID NO:88) | + |
| GRLWWQPYSVQR (SEQ ID NO:89) | +/− |
| HRIWWQPYSVQR (SEQ ID NO:90) | +/− |
| GRVWWQPYSVQR (SEQ ID NO:91) | +/− |
| ARVWWQPYSVQM (SEQ ID NO:92) | N.D. |
| RLMFYQPYSVQR (SEQ ID NO:93) | N.D. |
| ESMWYQPYSVQR (SEQ ID NO:94) | N.D. |
| HFGWWQPYSVHM (SEQ ID NO:95) | N.D. |
| ARFWYQPYSVQR (SEQ ID NO:96) | N.D. |

TABLE 6

Library Based on "RLVYWQ XXXXXX (SEQ ID NO:301)

| Peptide | IC$_{50}$ |
|---|---|
| RLVYWQ PYAPTY (SEQ ID NO:97) | + |
| RLVYWQ PYSYQT (SEQ ID NO:98) | + |
| RLVYWQ PYSLPI (SEQ ID NO:99) | + |
| RLVYWQ PYSVQA (SEQ ID NO:100) | + |
| RLVYWQ PWAPIW (SEQ ID NO:101) | − |

TABLE 7

Library Based on "SRVWYQ XXXXXX" (SEQ ID NO:302)

| Peptide | IC$_{50}$ |
|---|---|
| SRVWYQ PYAKGL (SEQ ID NO:102) | + |
| SRVWYQ PYAQGL (SEQ ID NO:103) | + |
| SRVWYQ PYAMPL (SEQ ID NO:104) | + |
| SRVWYQ PYSVQA (SEQ ID NO:105) | + |
| SRVWYQ PYSLGL (SEQ ID NO:106) | + |
| SRVWYQ PYAREL (SEQ ID NO:107) | + |
| SRVWYQ PYSRQP (SEQ ID NO:108) | + |
| SRVWYQ PYFVQP (SEQ ID NO:109) | +/− |

TABLE 8

Library Based on "XXXXXXXPYALPL" (SEQ ID NO:303)

| Peptide | IC$_{50}$ |
|---|---|
| EYEWYQ PYALPL (SEQ ID NO:110) | + |
| IPEYWQ PYALPL (SEQ ID NO:111) | + |
| SRIWWQ PYALPL (SEQ ID NO:112) | + |
| DPLFWQ PYALPL (SEQ ID NO:113) | + |
| SRQWVQ PYALPL (SEQ ID NO:114) | + |
| IRSWWQ PYALPL (SEQ ID NO:115) | + |
| RGYWQ PYALPL (SEQ ID NO:116) | + |
| RLLWVQ PYALPL (SEQ ID NO:117) | + |
| EYRWFQ PYALPL (SEQ ID NO:118) | + |
| DAYWVQ PYALPL (SEQ ID NO:119) | + |
| WSGYFQ PYALPL (SEQ ID NO:120) | + |
| NIEFWQ PYALPL (SEQ ID NO:121) | + |
| TRDWVQ PYALPL (SEQ ID NO:122) | + |
| DSSWYQ PYALPL (SEQ ID NO:123) | + |
| IGNWYQ PYALPL (SEQ ID NO:124) | + |
| NLRWDQ PYALPL (SEQ ID NO:125) | + |
| LPEFWQ PYALPL (SEQ ID NO:126) | + |
| DSYWWQ PYALPL (SEQ ID NO:127) | + |
| RSQYYQ PYALPL (SEQ ID NO:128) | + |
| ARFWLQ PYALPL (SEQ ID NO:129) | + |
| NSYFWQ PYALPL (SEQ ID NO:130) | + |
| ESFWVQ PYALPL (SEQ ID NO:131) | − |

TABLE 9

Library Based on "RLVYWQPYSVQR" (SEQ ID NO:304) with 70-10-10-10 Mutagenesis

| Peptide | IC$_{50}$ |
|---|---|
| RFMYWQPYSVQR (SEQ ID NO:132) | + |
| AHLFWQPYSVQR (SEQ ID NO:133) | + |
| WGNWWQPYSVHR (SEQ ID NO:134) | − |

TABLE 10

Library Based on "XXQPYXXXX" (SEQ ID NO:305)

| Peptide | IC$_{50}$ |
|---|---|
| WWQPYALPL (SEQ ID NO:135) | + |
| YYQPYALPL (SEQ ID NO:136) | + |
| YFQPYALGL (SEQ ID NO:137) | + |
| YFQPYALPF (SEQ ID NO:138) | − |

TABLE 11

Library Based on "XXXQPYXXXX" (SEQ ID NO:306)

| Peptide | IC$_{50}$ |
|---|---|
| YWYQPYALPL (SEQ ID NO:139) | + |
| RWWQPYATPL (SEQ ID NO:140) | + |
| GWYQPYALGF (SEQ ID NO:141) | + |
| YWYQPYALGL (SEQ ID NO:142) | + |
| IWYQPYAMPL (SEQ ID NO:143) | + |
| SNMQPYQRLS (SEQ ID NO:144) | N.D. |

TABLE 12

Library Based on "TFVYWQPY XXXXXXXXXXXX" (SEQ ID NO:307)

Peptide

TFVYWQPY AVGLFAAETACN (SEQ ID NO:145)
TFVYWQPY SVQMTTTGKVTM (SEQ ID NO:146)

TABLE 12-continued

Library Based on "TFVYWQPY XXXXXXXXXXXX" (SEQ ID NO:307)

| Peptide |
|---|
| TFVYWQPY SSHXXVPXGFPL (SEQ ID NO:147) |
| TFVYWQPY YGNPQWAIHVRH (SEQ ID NO:148) |
| TFVYWQPY VLLELPEGAVRA (SEQ ID NO:149) |
| TFVYWQPY VDYVWPIPIAQV (SEQ ID NO:150) |

A library based on the following motif "XXXXXX(PG/GP)XXXXXX" where X represents any of the naturally occurring L-amino acids was also prepared (SEQ ID NO:151). Screening of this library resulted in the identification of the peptide IMWFCQPGGACYSV (SEQ ID NO:152) which had an IC$_{50}$ of between 100 and 500 μM.

The peptides-on-plasmid system was also employed to identify peptides capable of interacting with the IL-1 receptor. Using this technique, a plasmid containing the LacI gene with an oligonucleotide cloning site at its 3'-end was constructed. Under the controlled induction by arabinose, a LacI-peptide fusion protein was produced. This fusion retains the natural ability of LacI to bind to the Lac operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically associated with the DNA sequence that directed its synthesis. The cells of the library were gently lysed and the peptide-DNA complexes were exposed to a matrix of immobilized receptor to recover the complexes containing the active peptides. The associated plasmid DNA was then reintroduced into cells for amplification and DNA sequencing to determine the identity of the peptide ligands. Using this system, the following peptides capable of interacting with the IL-1 receptor were identified.

TABLE 13

Library Based on "XXXQPYXXXXXX" (SEQ ID NO:308) using C-terminal lac Repressor System

| Peptide | IC$_{50}$ |
|---|---|
| GWYQPYVDGWR (SEQ ID NO:153) | + |
| RWEQPYVKDGWS (SEQ ID NO:154) | + |
| EWYQPYALGWAR (SEQ ID NO:155) | + |
| GWWQPYARGL (SEQ ID NO:156) | + |
| LFEQPYAKALGL (SEQ ID NO:157) | + |
| GWEQPYARGLAG (SEQ ID NO:158) | + |
| AWVQPYATPLDE (SEQ ID NO:159) | + |
| MWYQPYSSQPAE (SEQ ID NO:160) | + |
| GWTQPYSQQGEV (SEQ ID NO:161) | + |
| DWFQPYSIQSDE (SEQ ID NO:162) | + |
| PWIQPYARGFG (SEQ ID NO:163) | + |

A library was also screened by panning against IL-1 receptor expressed by cells to identify the following peptides:

TABLE 14

| Peptide | IC$_{50}$ |
|---|---|
| RPLYWQPYSVQV (SEQ ID NO:164) | + |
| TLIYWQPYSVQI (SEQ ID NO:165) | + |

TABLE 14-continued

| Peptide | IC$_{50}$ |
|---|---|
| RFDYWQPYSDQT (SEQ ID NO:166) | + |
| WHQFVQPYALPL (SEQ ID NO:167) | N.D. |

When using random peptide generation systems that allow for multivalent ligand-receptor interaction, one must recognize that the density of the immobilized receptor is an important factor in determining the affinity of the ligands that bind to the immobilized receptor. At higher receptor densities (i.e., each anti-receptor antibody-coated well treated with 250 to 500 ng of receptor), multivalent binding is more likely to occur (if at all) than at lower receptor densities (i.e., each anti-receptor antibody-coated well treated with 0.5 to 1 ng of the receptor). If multivalent binding is occurring, then one will be more likely to isolate ligands with relatively low affinity. Typically, one can identify lead compounds using a high density of immobilized receptor and then test the derivatives of the lead compound at lower receptor densities to isolate compounds with higher affinity for the receptor than the lead compound. By screening libraries under conditions of low receptor density, the following peptides were identified.

TABLE 15

Library Based on "XXXX VYWQPYSVQ XXXX" (SEQ ID NO:309) with Low Density Receptor

| Peptide |
|---|
| EWDS VYWQPYSVQ TLLR (SEQ ID NO:168) |
| WEQN VYWQPYSVQ SFAD (SEQ ID NO:169) |
| SDV VYWQPYSVQ SLEM (SEQ ID NO:170) |
| YYDG VYWQPYSVQ VMPA (SEQ ID NO:171) |

TABLE 16

Library Based on "XXXXXX PYALPL" (SEQ ID NO:310) with Low Density Receptor

| Peptide | IC$_{50}$ |
|---|---|
| SDIWYQ PYALPL (SEQ ID NO:172) | + |
| QRIWWQ PYALPL (SEQ ID NO:173) | + |
| SRIWWQ PYALPL (SEQ ID NO:174) | + |
| RSLYWQ PYALPL (SEQ ID NO:175) | + |
| TIIWEQ PYALPL (SEQ ID NO:176) | + |
| WETWYQ PYALPL (SEQ ID NO:177) | + |
| SYDWEQ PYALPL (SEQ ID NO:178) | + |
| SRIWCQ PYALPL (SEQ ID NO:179) | + |
| EIMFWQ PYALPL (SEQ ID NO:180) | + |
| DYVWQQ PYALPL (SEQ ID NO:181) | + |

TABLE 17

Library Based on "XXXXXX WYQPYALPL" (SEQ ID NO:311) with Low Density Receptor

| Peptide |
|---|
| MDLLVQ WYQPYALPL (SEQ ID NO:182) |
| GSKVIL WYQPYALPL (SEQ ID NO:183) |
| RQGANI WYQPYALPL (SEQ ID NO:184) |
| GGGDEP WYQPYALPL (SEQ ID NO:185) |
| SQLERT WYQPYALPL (SEQ ID NO:186) |
| ETWVRE WYQPYALPL (SEQ ID NO:187) |
| KKGSTQ WYQPYALPL (SEQ ID NO:188) |
| LQARMN WYQPYALPL (SEQ ID NO:189) |

TABLE 17-continued

Library Based on "XXXXXX WYQPYALPL" (SEQ ID NO:311) with Low Density Receptor Peptide EPRSQK WYQPYALPL (SEQ ID NO:190)
VKQKWR WYQPYALPL (SEQ ID NO:191)
LRRHDV WYQPYALPL (SEQ ID NO:192)
RSTASI WYQPYALPL (SEQ ID NO:193)
ESKEDQ WYQPYALPL (SEQ ID NO:194)
EGLTMK WYQPYALPL (SEQ ID NO:195)
EGSREG WYQPYALPL (SEQ ID NO:196)

A "monovalent" phage approach was also used to identify peptides capable of binding the IL-1 receptor. In this approach, phage particles with only a single chimeric pIII protein were created, thereby eliminating multivalent binding to immobilized receptor. Using this technique, the following peptides were identified.

TABLE 18

| Library Based on "XXXXXX PYALPL" (SEQ ID NO:310) with Monovalent Display | |
|---|---|
| Peptide | $IC_{50}$ |
| VIEWWQ PYALPL (SEQ ID NO:197) | + |
| VWYWEQ PYALPL (SEQ ID NO:198) | + |
| ASEWWQ PYALPL (SEQ ID NO:199) | + |
| FYEWWQ PYALPL (SEQ ID NO:200) | + |
| EGWWVQ PYALPL (SEQ ID NO:201) | + |
| WGEWLQ PYALPL (SEQ ID NO:202) | + |
| DYVWEQ PYALPL (SEQ ID NO:203) | + |
| AHTWWQ PYALPL (SEQ ID NO:204) | + |
| FIEWFQ PYALPL (SEQ ID NO:205) | + |
| WLAWEQ PYALPL (SEQ ID NO:206) | + |
| VMEWWQ PYALPL (SEQ ID NO:207) | N.D. |
| ERMWQ PYALPL (SEQ ID NO:208) | N.D. |

To ascertain a rough indication of the affinity of the peptides, selected phage libraries were also screened using an affinity selection protocol. In brief, this protocol relies on the rapid association and dissociation between the peptide on an individual phage (either pIII or pVIII) and the receptor. More specifically, for phage bearing low affinity ligands, the peptide on an individual pIII (or pVIII) protein may be rapidly dissociating and reassociating, but the phage particle will not dissociate unless all the peptides on the phage are simultaneously in the unbound state. Dissociation of the phage can be initiated by addition of a competing peptide, which prevents rebinding of any individual peptide in the complex. The concentration (and affinity) of the competing peptide, as well as the time and temperature of elution can be varied to select for peptides of various affinities.

Thus, to identify peptides capable of interacting with the IL-1 receptor, competition with a peptide or IL-1 was performed. This process is repeated typically for two rounds of panning. In subsequent rounds of panning, the competition temperature (4° C. to ambient temperature) and time (15 to 30 minutes) as well as the temperature (4° C. to ambient temperature) of the wash solutions can be altered to further select for peptides with high affinity.

TABLE 19

| Library Based on "XXXXXX PYALPL" (SEQ ID NO:310) with Peptide Competition | |
|---|---|
| Peptide | $IC_{50}$ |
| NXXWXX PYALPL (SEQ ID NO:209) | N.D. |
| WGNWYQ PYALPL (SEQ ID NO:210) | N.D. |
| TLYWEQ PYALPL (SEQ ID NO:211) | N.D. |
| VWRWEQ PYALPL (SEQ ID NO:212) | N.D. |
| LLWTQ PYALPL (SEQ ID NO:213) | N.D. |
| SRIWXX PYALPL (SEQ ID NO:214) | N.D. |
| SDIWYQ PYALPL (SEQ ID NO:172) | N.D. |
| WGYYXX PYALPL (SEQ ID NO:215) | N.D. |
| TSGWYQ PYALPL (SEQ ID NO:216) | N.D. |
| VHPYXX PYALPL (SEQ ID NO:217) | N.D. |
| EHSYFQ PYALPL (SEQ ID NO:218) | N.D. |
| XXIWYQ PYALPL (SEQ ID NO:219) | N.D. |
| AQLHSQ PYALPL (SEQ ID NO:220) | N.D. |
| WANWFQ PYALPL (SEQ ID NO:221) | N.D. |
| SRLYSQ PYALPL (SEQ ID NO:222) | N.D. |
| YYTWQQ PYALPL (SEQ ID NO:223) | — |
| GVTFSQ PYALPL (SEQ ID NO:224) | N.D. |
| GVVWYQ PYALPL (SEQ ID NO:225) | — |
| SIVWSQ PYALPL (SEQ ID NO:226) | N.D. |
| YYSWQ PYALPL (SEQ ID NO:227) | — |
| SRDLVQ PYALPL (SEQ ID NO:228) | N.D. |

TABLE 20

| Library Based on "XXXX VYWQPYSVQ XXXX" (SEQ ID NO:309) with IL-1 Competition | |
|---|---|
| Peptide | $IC_{50}$ |
| HWGH VYWQPYSVQ DDLG (SEQ ID NO:229) | + |
| SWHS VYWQPYSVQ SVPE (SEQ ID NO:230) | + |
| WRDS VYWQPYSVQ PESA (SEQ ID NO:231) | + |
| TWDA VYWQPYSVQ KWLD (SEQ ID NO:232) | N.D. |
| TPPW VYWQPYSVQ SLDP (SEQ ID NO:233) | N.D. |
| YWSS VYWQPYSVQ SVHS (SEQ ID NO:234) | N.D. |

TABLE 21

Peptides Identified from Library Based on "XXX QPY XXXX" (SEQ ID NO:306) with Peptide Competition Peptide YWY QPY ALGL (SEQ ID NO:235)
YWY QPY ALPL (SEQ ID NO:236)
EWI QPY ATGL (SEQ ID NO:237)
NWE QPY AKPL (SEQ ID NO:238)
AFY QPY ALPL (SEQ ID NO:239)
FLY QPY ALPL (SEQ ID NO:240)
VCK QPY LEWC (SEQ ID NO:241)

To more clearly define the preferred sequences, several additional libraries were screened using a colony lift technique. In brief, cells were infected with phage encoding random peptides and were plated on media containing arabinose to induce expression of the random peptides. Colonies were transferred to nitrocellulose filters which were washed extensively and then incubated at 4° C. with $^{33}$P radiolabeled IL-1R. The filters were washed, dried, and exposed to X-ray film. The sequences of peptides identified using this technique are shown below.

TABLE 22

Peptides Identified Using Colony Lift Procedure

| Peptide | IC$_{50}$ |
|---|---|
| ETPFTWEESNAYYWQPYALPL (SEQ ID NO:254) | ++ |
| QGWLTWQDSVDMYWQPYALPL (SEQ ID NO:370) | N.D. |
| FSEAGYTWPENTYWQPYALPL (SEQ ID NO:371) | N.D. |
| TESPGGLDWAKIYWQPYALPL (SEQ ID NO:372) | N.D. |
| DGYDRWRQSGERYWQPYALPL (SEQ ID NO:255) | ++ |
| TANVSSFEWTPGYWQPYALPL (SEQ ID NO:256) | ++ |

TABLE 23

Peptides Identified from Library Based on "XXXXXXXXXXXX YWQPYALPL" (SEQ ID NO:312)

| Peptide | IC$_{50}$ |
|---|---|
| SVGEDHNFWTSE YWQPYALPL (SEQ ID NO:242) | ++ |
| MNDQTSEVSTFP YWQPYALPL (SEQ ID NO:243) | N.D. |
| SWSEAFEQPRNL YWQPYALPL (SEQ ID NO:244) | N.D. |
| QYAEPSALNDWG YWQPYALPL (SEQ ID NO:245) | N.D. |
| NGDWATADWSNY YWQPYALPL (SEQ ID NO:246) | N.D. |
| THDEHI YWQPYALPL (SEQ ID NO:247) | N.D. |
| MLEKTYTTWTPG YWQPYALPL (SEQ ID NO:248) | N.D. |
| WSDPLTRDADL YWQPYALPL (SEQ ID NO:249) | N.D. |
| SDAFTTQDSQAM YWQPYALPL (SEQ ID NO:250) | N.D. |
| GDDAAWRTDSLT YWQPYALPL (SEQ ID NO:251) | N.D. |
| AIIRQLYRWSEM YWQPYALPL (SEQ ID NO:252) | N.D. |
| ENTYSPNWADSM YWQPYALPL (SEQ ID NO:253) | ++ |
| MNDQTSEVSTFP YWQPYALPL (SEQ ID NO:243) | N.D. |
| SVGEDHNFWTSE YWQPYALPL (SEQ ID NO:244) | N.D. |
| QTPFTWEESNAY YWQPYALPL (SEQ ID NO:257) | N.D. |
| ENPFTWQESNAY YWQPYALPL (SEQ ID NO:258) | N.D. |
| VTPFTWEDSNVF YWQPYALPL (SEQ ID NO:259) | N.D. |
| QIPFTWEQSNAY YWQPYALPL (SEQ ID NO:260) | N.D. |
| QAPLTWQESAAY YWQPYALPL (SEQ ID NO:261) | N.D. |
| EPTFTWEESKAT YWQPYALPL (SEQ ID NO:262) | N.D. |
| TTTLTWEESNAY YWQPYALPL (SEQ ID NO:263) | N.D. |
| ESPLTWEESSAL YWQPYALPL (SEQ ID NO:264) | N.D. |
| ETPLTWEESNAY YWQPYALPL (SEQ ID NO:265) | N.D. |
| EATFTWAESNAY YWQPYALPL (SEQ ID NO:266) | N.D. |
| EALFTWKESTAY YWQPYALPL (SEQ ID NO:267) | N.D. |
| STP-TWEESNAY YWQPYALPL (SEQ ID NO:268) | N.D. |
| ETPFTWEESNAY YWQPYALPL (SEQ ID NO:269) | N.D. |
| KAPFTWEESQAY YWQPYALPL (SEQ ID NO:270) | N.D. |
| STSFTWEESNAY YWQPYALPL (SEQ ID NO:271) | N.D. |
| DSTFTWEESNAY YWQPYALPL (SEQ ID NO:272) | N.D. |
| YIPFTWEESNAY YWQPYALPL (SEQ ID NO:273) | N.D. |
| QTAFTWEESNAY YWQPYALPL (SEQ ID NO:274) | N.D. |
| ETLFTWEESNAT YWQPYALPL (SEQ ID NO:275) | N.D. |
| VSSFTWEESNAY YWQPYALPL (SEQ ID NO:276) | N.D. |

Analog analysis of the sequence N-terminal from the QPYALPL motif produced a peptide having the sequence pY(1Nap)pYQJYALPL (SEQ ID NO:330), having an IC$_{50}$ of less than 500 nM, where pY is phosphotyrosine and 1Nap is naphthylalanine.

Additionally, truncation of the peptide TANVSSFEW-TPG YWQPYALPL yielded the peptide FEWTPGYWQPY-ALPL (SEQ ID NO:331) having an IC50 of less than 500 nM. Substitution of the proline in the QPY motif yielded a peptide of similar affinity, as did substitution of the tryptophan residue within the YW motif with tyrosine. These peptides are thus FEWTPGYWQJYALPL (SEQ ID NO:356) and FEWTPGYYQJYALPL (SEQ ID NO:358).

The peptide ETPFTWEESNAYYWQPYALPL (SEQ ID NO:13) was truncated at the N terminus, and the proline in the QPY motif was substituted with azetidine to yield the peptide FTWEESNAYYWQJYALPL (SEQ ID NO:332), which had an IC$_{50}$ of less than 500 nM. Truncation of both the N-terminal ETP sequence and the C-terminal ALPL region in the original peptide, yielded the peptide FTWEESNAYYWQPY-NH$_2$ (SEQ ID NO:333), having an IC$_{50}$ of less than 500 nM. Substitution of the proline in the QPY motif with azetidine, gives the peptide FTWEESNAYYWQJY-NH$_2$ (SEQ ID NO:313), having a similarly strong affinity (an IC$_{50}$ of less than 500 nM).

TABLE 24

Other Peptide Identified by Colony Lifts with Labeled Receptor

| Peptide | IC$_{50}$ |
|---|---|
| ADVL YWQPYA PVTLWV (SEQ ID NO:277) | N.D. |
| GDVAE YWQPYA LPLTSL (SEQ ID NO:278) | N.D. |
| SWTDYG YWQPYA LPISGL (SEQ ID NO:279) | ++ |

The above data illustrate a peptide comprising a core sequence of amino acids XXQZ$_5$YZ$_6$XX where X can be selected from any one of the 20 genetically coded L-amino acids; Z$_5$ is P or Aze where Aze is azetidine; and Z$_6$ is S, A, V, or L (SEQ ID NO:6). More preferably, the sequence comprises Z$_7$XQZ$_5$YZ$_6$XX where X can be selected from any one of the 20 genetically coded L-amino acids; Z$_5$ is P or Aze where Aze is azetidine; Z$_6$ is S or A; and Z$_7$ is Y, W, or F (SEQ ID NO:7). In a more preferred embodiment, the core sequence of amino acids will comprise Z$_7$Z$_8$QZ$_5$YZ$_6$Z$_9$Z$_{10}$ where Z$_5$ is P or Aze where Aze is azetidine; Z$_6$ is S or A; Z$_7$ is Y, W or F; Z$_8$ is E, F, V, W, or Y; Z$_9$ is M, F, V, R, Q, K, T, S, D, L, I, or E; and Z$_{10}$ is E, L, W, V, H, I, G, A, D, L, Y, N, Q or P (SEQ ID NO:8). More preferably, Z$_9$ is V, L, I, or E; and Z$_{10}$ is Q or P. Most preferably, the core peptide will comprise a sequence of amino acids Z$_{11}$Z$_7$Z$_8$QZ$_5$YZ$_6$Z$_9$Z$_{10}$, where Z$_8$ is Y, W or F; and Z$_{11}$ is V, L, I, E, P, G, Y, M, T, or, D (SEQ ID NO:9).

Specific examples of these peptides include FEWTPGY-WQPYALPL (SEQ ID NO:331), FEWTPGYWQJYALPL (SEQ ID NO:356), FEWTPGWYQPYALPL (SEQ ID NO:402), FEWTPGWYQJYALPL (SEQ ID NO:400), FEWTPGYYQPYALPL (SEQ ID NO:403) and FEWT-PGYYQJYALPL (SEQ ID NO:358).

An especially preferred embodiment is one having the substitution patterns just described, but comprising 21 amino acid residues. Particularly preferred is the peptide comprising the sequence of amino acids Z$_{12}$Z$_{13}$Z$_{14}$Z$_{15}$Z$_{16}$Z$_{17}$Z$_{18}$Z$_{19}$Z$_{20}$Z$_{21}$Z$_{22}$Z$_{11}$Z$_7$Z$_8$QZ$_5$YZ$_6$Z$_9$-Z$_{10}$L, where Z$_8$ is Y, W or F; Z$_{11}$ is V, L, I, E, P, G, Y, M, T, or, D; Z$_{12}$ is A, D, E, F, G, K, Q, S, T, V, or Y; Z$_{13}$ is A, D, G, I, N, P, S, T, V, or W; Z$_{14}$ is A, D, G, L, N, P, S, T, W, or Y; Z$_{15}$ is A, D, E, F, L, N, R, V, or Y; Z$_{16}$ is A, D, E, Q, R, S, or T; Z$_{17}$ is H, I, L, P, S, T, or, W; Z$_{18}$ is A, E, F, K, N, Q, R, S, or Y; Z$_{19}$ is D, E, F, Q, R, T, or W; Z$_{20}$ is A, D, P, S, T, or W; Z$_{21}$ is A, D, G, K, N, Q, S, or T; and Z$_{22}$ is A, E, L, P, S, T, V, or Y (SEQ ID NO:10). More preferably, Z$_8$ is Y, W or F; Z$_{11}$ is V, L, I, E, P, G, Y, M, T, or, D; Z$_{12}$ is D, E, Q, S, T, V, or Y; Z$_{13}$ is A, D, G, I, N, S, T or V; Z$_{14}$ is A, G, L, N, P, S, T, or Y; Z$_{15}$ is D, E, F, L, V, or Y; Z$_{16}$ is D, R, S or T; Z$_{17}$ is H, P, S, or W; Z$_{18}$ is E, F, N, R, Q, or S; Z$_{19}$ is D, E, F, Q, or W; Z$_{20}$ is S, T, or W; Z$_{21}$ is D, G, K, N, Q, S, or T; and Z$_{22}$ is A, E, P, S, or Y (SEQ ID NO:298).

Particularly preferred peptides include TANVSSFEWT-PGYWQPYALPL (SEQ ID NO:11); SWTDYGYWQPY-ALPISGL (SEQ ID NO:12); ETPFTWEESNAYYWQPY-ALPL (SEQ ID NO:13); ENTYSPNWADSMYWQPYALPL (SEQ ID NO:14); SVGEDHNFWTSEYWQPYALPL (SEQ ID NO:15); and DGYDRWRQSGERYWQPYALPL (SEQ ID NO:16).

Truncations of the TANVSSFEWTPGYWQPYALPL (SEQ ID NO:11) peptide were synthesized and tested for their ability to inhibit the binding of IL-1α to IL-1RtI, and the following peptides were identified:

TABLE 25

| Peptide | IC$_{50}$ |
|---|---|
| FEWTPGYWQPYALPL (SEQ ID NO:331) | ++ |
| FEWTPGYWQPY-NH$_2$ (SEQ ID NO:315) | ++ |
| FEWTPGYWQJY-NH$_2$ (SEQ ID NO:316) | ++ |
| EWTPGYWQPY-NH$_2$ (SEQ ID NO:336) | + |
| FEWTPGWYQJY-NH$_2$ (SEQ ID NO:317) | ++ |

Deletion of the six N-terminal amino acids was found to have little effect on the affinity of the peptide. While deletion of the C-terminal ALPL sequence resulted in a five-fold decrease, the 11mer peptide was still found to be a good inhibitor of IL-1α binding, having an IC$_{50}$ of well below 500 nM. Furthermore, substitution of azetidine (J) for the proline in the number 10 position of the 11mer restored much of the lost affinity. Deletion of the N-terminal phenylalanine, however, resulted in a large reduction in affinity.

The 11mer, FEWTPGYWQJY-NH$_2$ (SEQ ID NO:316), was subject to further substitution and analoging. Specifically, sequential alanine substitution was used to determine the important functional positions in the sequence of the peptide. The following peptides and results were obtained from the alanine substitution:

TABLE 26

| Peptide | IC$_{50}$ |
|---|---|
| AEWTPGYWQJY-NH$_2$ (SEQ ID NO:337) | + |
| FAWTPGYWQJY-NH$_2$ (SEQ ID NO:320) | ++ |
| FEATPGYWQJY-NH$_2$ (SEQ ID NO:338) | + |
| FEWAPGYWQJY-NH$_2$ (SEQ ID NO:321) | ++ |
| FEWTAGYWQJY-NH$_2$ (SEQ ID NO:339) | ++ |
| FEWTPAYWQJY-NH$_2$ (SEQ ID NO:340) | ++ |
| FEWTPGAWQJY-NH$_2$ (SEQ ID NO:341) | +/++ |
| FEWTPGYAQJY-NH$_2$ (SEQ ID NO:342) | + |
| FEWTPGYWAJY-NH$_2$ (SEQ ID NO:343) | - |
| FEWTPGYWQJA-NH$_2$ (SEQ ID NO:344) | + |

Alanine substitution at positions 2 and 4 yielded no appreciable loss in affinity of the peptide. These data therefore indicate that the residue requirements in these positions are flexible. Alanine substitutions at positions 5, 6 and 7, while somewhat affecting affinity, still yielded peptides with strong affinity. These positions are therefore considered moderately flexible as to their specific amino acid requirements.

TABLE 27

Substitution and Analoging the PG Motif

| Peptide | IC$_{50}$ |
|---|---|
| FEWTGGYWQJY-NH$_2$ (SEQ ID NO:345) | + |
| FEWTpGYWQJY-NH$_2$ | ++ |
| FEWTJGYWQJY-NH$_2$ (SEQ ID NO:346) | ++ |
| FEWTPecGYWQJY-NH$_2$ (SEQ ID NO:347) | ++ |
| FEWTPAibYWQJY-NH$_2$ (SEQ ID NO:348) | ++ |
| FEWTPSarWYQJY-NH$_2$ (SEQ ID NO:326) | ++ |
| FEWTSarGYWQJY-NH$_2$ (SEQ ID NO:349) | ++ |
| FEWTPNYWQJY-NH$_2$ (SEQ ID NO:350) | ++ |
| FEWTPvYWQJY-NH$_2$ | ++ |
| FEWTVPYWQJY-NH$_2$ (SEQ ID NO:351) | + |

TABLE 27-continued

Substitution and Analoging the PG Motif

| Peptide | IC$_{50}$ |
|---|---|
| AcFEWTPGWYQJY-NH$_2$ (SEQ ID NO:318) | ++ |
| AcFEWTPGYWQJY-NH$_2$ (SEQ ID NO:324) | ++ |

Acetylation of the N-terminal phenylalanine was found to have little impact on affinity.

Combinatorial libraries were prepared using both the ESL and VLSIPS™ methods, based upon the general peptide sequence XXXXPGYYQJY (SEQ ID NO:375), where the X residues are substituted with a number of different building blocks. A number of peptides were identified as having apparent strong affinity, and these peptides were synthesized, and their binding affinities determined. The results are summarized below.

TABLE 28

Combinatorial Library Based upon XXXXPGYYQJY

| Peptide | IC$_{50}$ |
|---|---|
| 1Nap-EWTPGYYQJY-NH$_2$ | ++ |
| YEWTPGYYQJY-NH$_2$ | ++ |
| FEWVPGYYQJY-NH$_2$ | ++ |

A similar combinatorial strategy focused upon the central PG motif of the FEWTPGYYQJY (SEQ ID NO:405) peptide. The peptides FEWTPsYYQJY-NH$_2$ and FEWTPnYYQJY-NH$_2$ were identified as having IC$_{50}$s well below 500 nM.

The preferred motif sequences also provide a means to determine the minimum size of an IL-1R blocking compound of the invention. One may use the "encoded synthetic library" (ESL) system described in U.S. patent application Ser. No. 946,239, filed Sep. 16, 1992, which is a continuation-in-part application of Ser. No. 762,522, filed Sep. 18, 1991, or the "very large scale immobilized polymer synthesis" system described in U.S. patent application Ser. Nos. 492,462, filed Mar. 7, 1990; 624,120, filed Dec. 6, 1990; and 805,727, filed Dec. 6, 1991; to not only determine the minimum size of a peptide with such activity, one can also make all of the peptides that form the group of peptides that differ from the preferred motif (or the minimum size of that motif) in one, two, or more residues. This collection of peptides can then be screened for ability to bind to IL-1-receptor. This immobilized polymer synthesis system or other peptide synthesis methods can also be used to synthesize every truncation analog and every deletion analog and every combination of truncation and deletion analog of all of the peptide compounds of the invention.

The peptides of the invention can be prepared by classical methods known in the art, for example, by using standard solid phase techniques. The standard methods include exclusive solid phase synthesis, partial solid phase synthesis methods, fragment condensation, classical solution synthesis, and even by recombinant DNA technology. See, e.g., Merrifield (1963) *J. Am. Chem. Soc.* 85:2149, incorporated herein by reference. On solid phase, the synthesis is typically commenced from the C-terminal end of the peptide using an alpha-amino protected resin. A suitable starting material can be prepared, for instance, by attaching the required alpha-amino acid to a chloromethylated resin, a hydroxymethyl resin, or a benzhydrylamine resin. One such chloromethylated resin is sold under the trade name BIO- BEADS SX-1 by Bio Rad Laboratories, Richmond, Calif., and the preparation of the hydroxymethyl resin is described by Bodanszky et al., (1966) *Chem. Ind. (London)* 38:1597. The benzhydrylamine (BHA) resin has been described by Pietta and Marshall (1970) *Chem. Commn.* 650, and is commercially available from Beckman Instruments, Inc., Palo Alto, Calif., in the hydrochloride form.

Thus, the compounds of the invention can be prepared by coupling an alpha-amino protected amino acid to the chloromethylated resin with the aid of, for example, cesium bicarbonate catalyst, according to the method described by Gisin (1973) *Helv. Chim. Acta* 56:1467. After the initial coupling, the alpha-amino protecting group is removed by a choice of reagents including trifluoroacetic acid (TFA) or hydrochloric acid (HCl) solutions in organic solvents at room temperature.

The alpha-amino protecting groups are those known to be useful in the art of stepwise synthesis of peptides. Included are acyl type protecting groups (e.g., formyl, trifluoroacetyl, acetyl), aromatic urethane type protecting groups (e.g., benzyloxycarboyl (Cbz) and substituted Cbz), aliphatic urethane protecting groups (e.g., t-butyloxycarbonyl (Boc), isopropyloxycarbonyl, cyclohexyloxycarbonyl) and alkyl type protecting groups (e.g., benzyl, triphenylmethyl). Boc and Fmoc are preferred protecting groups. The side chain protecting group remains intact during coupling and is not split off during the deprotection of the amino-terminus protecting group or during coupling. The side chain protecting group must be removable upon the completion of the synthesis of the final peptide and under reaction conditions that will not alter the target peptide.

The side chain protecting groups for Tyr include tetrahydropyranyl, tert-butyl, trityl, benzyl, Cbz, Z-Br-Cbz, and 2,5-dichlorobenzyl. The side chain protecting groups for Asp include benzyl, 2,6-dichlorobenzyl, methyl, ethyl, and cyclohexyl. The side chain protecting groups for Thr and Ser include acetyl, benzoyl, trityl, tetrahydropyranyl, benzyl, tert-butyl 2,6-dichlorobenzyl, and Cbz. The side chain protecting groups for Arg include nitro, Tosyl (Tos), Cbz, adamantyloxycarbonyl mesitoylsulfonyl (Mts), or Boc. The side chain protecting groups for Lys include Cbz, 2-chlorobenzyloxycarbonyl (2-Cl-Cbz), 2-bromobenzyloxycarbonyl (2-BrCbz), Tos, or Boc.

After removal of the alpha-amino protecting group, the remaining protected amino acids are coupled stepwise in the desired order. An excess of each protected amino acid is generally used with an appropriate carboxyl group activator such as dicyclohexylcarbodiimide (DCC) in solution, for example, in methylene chloride (CH$_2$Cl$_2$), dimethyl formamide (DMF) mixtures.

After the desired amino acid sequence has been completed, the desired peptide is decoupled from the resin support by treatment with a reagent such as trifluoroacetic acid or hydrogen fluoride (HF), which not only cleaves the peptide from the resin, but also cleaves all remaining side chain protecting groups. When the chloromethylated resin is used, hydrogen fluoride treatment results in the formation of the free peptide acids. When the benzhydrylamine resin is used, hydrogen fluoride treatment results directly in the free peptide amide. Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide. Side chain protection is then removed in the usual fashion by treatment with hydrogen fluoride to give the free amides, alkylamides, or dialkylamides.

In preparing the compounds of the invention, the resins used to prepare the peptide acids are employed, and the side chain protected peptide is cleaved with base and the appropriate alcohol, i.e., methanol. Side chain protecting groups are then removed in the usual fashion by treatment with hydrogen fluoride to obtain the desired ester. These solid phase peptide synthesis procedures are well known in the art and further described in Stewart, *Solid Phase Peptide Syntheses* (Freeman and Co., San Francisco, 1969).

These procedures can also be used to synthesize peptides in which amino acids other than the 20 naturally occurring, genetically encoded amino acids are substituted at one, two, or more positions of any of the compounds of the invention. For instance, naphthylalanine can be substituted for tryptophan, facilitating synthesis. Other synthetic amino acids that can be substituted into the peptides of the present invention include L-hydroxypropyl, L-3, 4-dihydroxyphenylalanyl, α amino acids such as L-α-hydroxylysyl and D-α-methylalanyl, L-α-methylalanyl, β amino acids, and isoquinolyl. D amino acids and non-naturally occurring synthetic amino acids can also be incorporated into the peptides of the present invention.

One can replace the naturally occurring side chains of the 20 genetically encoded amino acids (or D amino acids) with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclic. In particular, proline analogs in which the ring size of the proline residue is changed from 5 members to 4, 6, or 7 members can be employed. Cyclic groups can be saturated or unsaturated, and if unsaturated, can be aromatic or non-aromatic.

For example, the following peptides were prepared where "Nap" represents naphthylalanine and "J" or "Aze" represents azetidine.

TABLE 29

| Peptide | IC$_{50}$ |
| --- | --- |
| SHLY-Nap-QPYSVQM (SEQ ID NO:282) | + |
| TLVY-Nap-QPYSLQT (SEQ ID NO:283) | + |
| RGDY-Nap-QPYSVQS (SEQ ID NO:284) | + |
| NMVY-Nap-QPYSIQT (SEQ ID NO:285) | + |
| VYWQPYSVQ (SEQ ID NO:286) | + |
| VY-Nap-QPYSVQ (SEQ ID NO:287) | + |
| TFVYWQJYALPL (SEQ ID NO:288) | + |

The peptides of the present invention may also have incorporated within their sequence, a photoreactive amino acid. For example, p-benzoyl-L-phenylalanine may be readily incorporated into the amino acid sequence of the peptides described herein. This amino acid derivative is photolyzed by exposure to electromagnetic radiation at or near the UV range of the spectrum, e.g., 350 nm. When photolyzed, this amino acid analog attacks proximal C—H bonds, resulting in the formation of a covalent complex. See, e.g., Dorman, et al., Biochemistry 33:5661–5673 (1994). By varying the position of the Bpa residue within the peptide sequence, the peptides may be used as photolabels to map the IL-1 binding domain, and more particularly, to determine the specific residues which interact with the ligand binding domain of the IL-1 receptor. See, Kauer, et al., J. Biol. Chem. 261(23):10695–10700 (1986). Determination of which peptides form a covalent complex may be carried out by standard HPLC methods, e.g., as described in Kauer, et al., or optionally, the peptide may comprise any of a number of labelling groups to facilitate detection.

The following specific peptides were prepared by substituting various positions of the peptide AcFEWTPGYYQJY-NH$_2$ (SEQ ID NO:359), having both free and acetylated N-terminals, with p-benzoyl-L-phenylalanine ("Bpa"). The resulting peptides and their approximate binding affinities are listed below:

TABLE 30

Photoreactive Peptides

| Peptide | IC$_{50}$ |
|---|---|
| FEWTPGYYQJ-Bpa-NH$_2$ (SEQ ID NO:404) | + |
| AcFEWTPGYYQJ-Bpa-NH$_2$ (SEQ ID NO:361) | + |
| FEWTPGY-Bpa-QJY-NH$_2$ (SEQ ID NO:360) | ++ |
| AcFEWTPGY-Bpa-QJY-NH$_2$ (SEQ ID NO:362) | ++ |
| FEWTPG-Bpa-YQJY-NH$_2$ (SEQ ID NO:363) | ++ |
| AcFEWTPG-Bpa-YQJY-NH$_2$ (SEQ ID.NO: 364) | ++ |
| FE-Bpa-TPGYYQJY-NH$_2$ (SEQ ID NO:376) | − |
| AcFE-Bpa-TPGYYQJY-NH$_2$ (SEQ ID NO:377) | + |
| Bpa-EWTPGYYQJY-NH$_2$ (SEQ ID NO:365) | ++ |
| AcBpa-EWTPGYYQJY-NH$_2$ (SEQ ID NO:366) | ++ |

From the above tables, preferred high affinity peptides were identified which comprise an 11 amino acid core sequence $Z_{31}XWZ_{32}Z_{33}Z_{34}Z_{35}Z_{36}QZ_{37}Z_{38}$ (SEQ ID NO:314), including amides and esters thereof. In this core sequence, each letter represents the standard one letter abbreviation for an amino acid or an analog thereof.

The residue represented by X may be any natural or unnatural amino acid. The residue in position $Z_{31}$ may be phenylalanine, acetylated phenylalanine, tyrosine, acetylated tyrosine, 1-naphthylalanine, acetylated 1-napthylalanine, p-benzoyl-L-phenylalanine, and acetylated p-benzoyl-L-phenylalanine. The $Z_{32}$ residue may be any natural or unnatural amino acid, however, alanine, threonine and valine are preferred. $Z_{33}$ may be selected from proline and pipecolic acid, and $Z_{34}$ may be selected from glycine, asparagine, d-asparagine, d-alanine, d-valine, d-serine, sarcosine and aminoisobutyric acid. The $Z_{35}$ residue may be a natural or unnatural amino acid, however, both $Z_{35}$ and $Z_{36}$ are preferably selected from tyrosine, phosphotyrosine (denoted "-pY-"), phenylalanine, tryptophan, 1-naphthylalanine and p-benzoyl-L-phenylalanine. The $Z_{37}$ residue can be any natural or unnatural cyclic amino acid, with proline and azetidine being preferred. The residue at position $Z_{38}$ is selected from tyrosine tyrosinamide and substituted tyrosinamide.

Particularly preferred peptides include those having the following core sequences: FEWTPGYWQPY-NH2 (SEQ ID NO:315); FEWTPGYWQJY-NH2 (SEQ ID NO:316); FEWTPGWYQJY-NH2 (SEQ ID NO:317); AcFEWTPGWYQJY-NH2 (SEQ ID NO:318); FEWTPGW-pY-QJY-NH2 (SEQ ID NO:319); FAWTPGYWQJY-NH2 (SEQ ID NO:320); FEWAPGYWQJY-NH2 (SEQ ID NO:321); FEWVPGYWQJY-NH2 (SEQ ID NO:322); FEWTPGYWQJY-NH2 (SEQ ID NO:323); AcFEWTPGYWQJY-NH2 (SEQ ID NO:324); FEWTPaWYQJY-NH2; FEWTP-Sar-WYQJY-NH2 (SEQ ID NO:326); FEWTPGYYQPY-NH2 (SEQ ID NO:3278); FEWTPGWWQPY-NH2 (SEQ ID NO:328); FEWTPNYWQPY-NH2 (SEQ ID NO:329); FEWTPvYWQJY-NH2; and FEWTPGYWQPYALPL (SEQ ID NO:331); FEWTPGYYQJ-Bpa-NH$_2$ (SEQ ID NO:404); AcFEWTPGYYQJ-Bpa-NH$_2$ (SEQ ID NO:361); FEWTPGY-Bpa-QJY-NH$_2$ (SEQ ID NO:360); AcFEWTPGY-Bpa-QJY-NH$_2$ (SEQ ID NO:362); FEWTPG-Bpa-YQJY-NH$_2$ (SEQ ID NO:363); AcFEWTPG-Bpa-YQJY-NH$_2$ (SEQ ID NO:364); FE-Bpa-TPGYYQJY-NH$_2$ (SEQ ID NO:376); AcFE-Bpa-TPGYYQJY-NH$_2$ (SEQ ID NO:377); Bpa-EWTPGYYQJY-NH$_2$ (SEQ ID NO:365); AcBpa-EWTPGYYQJY-NH$_2$ (SEQ ID NO:366); 1Nap-EWTPGYYQJY-NH$_2$ (SEQ ID NO:367); YEWTPGYYQJY-NH$_2$ (SEQ ID NO:368); FEWVPGYYQJY-NH$_2$ (SEQ ID NO:369); FEWTPsYYQJY-NH$_2$ and FEWTPnYYQJY-NH$_2$ wherein the N-terminal is optionally acetylated and/or the C-terminal is the amide, e.g., AcF is acetylated Phenylalanine, Y-NH2 is Tyrosinamnide.

Other preferred peptides of the invention synthesized by techniques standard in the art are shown below.

TABLE 31

| Peptide |
|---|
| VYWQPYSVQ (SEQ ID NO:289) |
| RLVYWQPYSVQR (SEQ ID NO:40) |
| RLVY-Nap-QPYSVQR (SEQ ID NO:290) |
| RLDYWQPYSVQR (SEQ ID NO:291) |
| RLVWFQPYSVQR (SEQ ID NO:292) |
| RLVYWQPYSIQR (SEQ ID NO:293) |

B. Non OPY 11mer Peptides

Another sequence motif was identified by screening a pVIII 11-mer library. This sequence comprises $Z_{23}NZ_{24}Z_{39}Z_{25}Z_{26}Z_{27}Z_{28}Z_{29}Z_{30}Z_{40}$ where $Z_{23}$ is D or Y; $Z_{24}$ is D, S or T; $Z_{39}$ is S, T or A; $Z_{25}$ is S or W; $Z_{26}$ is S or Y; $Z_{27}$ is D, Q, E or V; $Z_{28}$ is N, S, K, H or W; $Z_{29}$ is F or L; $Z_{30}$ is D, N, S or L; and $Z_{40}$ is L, I, Q, M or A (SEQ ID NO:17). Representative samples of this sequence motif include:

TABLE 32

| peptide | IC$_{50}$ |
|---|---|
| DNSSWYDSFLL (SEQ ID NO:280) | + |
| DNTAWYESFLA (SEQ ID NO:334) | + |
| DNTAWYENFLL (SEQ ID NO:335) | + |

Two extension libraries were prepared based upon the peptide XXXXDNTAWYESFLLXX (SEQ ID NO:382), where X residues were encoded using NNK, the underlined residues were mutagenized using the 70-10-10-10 approach, and the remaining residues were kept fixed. Probing with bivalent $^{33}$P-labelled receptor identified the following clones:

TABLE 33

| Peptide |
|---|
| PARE DNTAWYDSFLI WC (SEQ ID NO:383) |
| TSEY DNTTWYEKFLA SQ (SEQ ID NO:384) |
| SQIP DNTAWYQSFLL HG (SEQ ID NO:385) |
| SPFI DNTAWYENFLL TY (SEQ ID NQ:386) |
| EQIY DNTAWYDHFLL SY (SEQ ID NO:387) |
| TPFI DNTAWYENFLL TY (SEQ ID NO:388) |
| TYTY DNTAWYERFLM SY (SEQ ID NO:389) |
| TMTQ DNTAWYENFLL SY (SEQ ID NO:390) |

The peptide TYTYDNTAWYERFLMSY (SEQ ID NO:389) was assayed for affinity and yielded an IC$_{50}$ well below 500 nM.

The second, similar library was prepared switching the length of the amino and carboxy-terminal extensions. Thus the library was based upon the peptide XXDNTAWYES-FLLXXXX (SEQ ID NO:391). The following sequences were identified:

TABLE 34

| Peptide |
|---|
| TI DNTAWYANLVQ TYPQ (SEQ ID NO:392) |
| TI DNTAWYERFLA QYPD (SEQ ID NO:393) |
| HI DNTAWYENFLL TYTP (SEQ ID NO:394) |
| SQ DNTAWYENFLL SYKA (SEQ ID NO:395) |
| QI DNTAWYERFLL QYNA (SEQ ID NO:396) |
| NQ DNTAWYESFLL QYNT (SEQ ID NO:397) |
| TI DNTAWYENFLL NHNL (SEQ ID NO:398) |
| HY DNTAWYERFLQ QGWH (SEQ ID NO:399) |

The peptides HIDNTAWYENFLLTYTP (SEQ ID NO:394) and QIDNTAWYERFLLQYNA (SEQ ID NO:396) were assayed for affinity and yielded an IC$_{50}$ well below 500 nM.

The present invention also includes the peptides of the invention which have been modified, including, e.g., truncations, deletions, analogs, acylated and/or amidated derivatives, and the like. For example, the peptides may be truncated at either the amino or carboxy terminus, or both. Additionally, although the peptides have been described in terms of having a free carboxy and/or amino terminus, it may also be appreciated that one can modify the amino and/or carboxy terminus of the peptide compounds of the invention to produce other compounds of the invention.

For example, amino terminus modifications include methylating (i.e., —NHCH$_3$ or —NH(CH$_3$)$_2$), acetylating, adding a benzyloxycarbonyl group, or blocking the amino terminus with any blocking group containing a carboxylate functionality defined by RCOO—, where R is selected from the group consisting of naphthyl, acridinyl, steroidyl, and similar groups. Carboxy terminus modifications include replacing the free acid with a carboxamide group or forming a cyclic lactam at the carboxy terminus to introduce structural constraints. One can also cyclize the peptides of the invention, or incorporate a desamino or descarboxy residue at the termini of the peptide, so that there is no terminal amino or carboxyl group, to decrease susceptibility to proteases or to restrict the conformation of the peptide. C-terminal functional groups of the compounds of the present invention include amide, amide lower alkyl, amide di(lower alkyl), lower alkoxy, hydroxy, and carboxy, and the lower ester derivatives thereof, and the pharmaceutically acceptable salts thereof.

One can also readily modify peptides by phosphorylation, and other methods for making peptide derivatives of the compounds of the present invention are described in Hruby et al., (1990) Biochem J. 268(2):249–262, incorporated herein by reference. Thus, the peptide compounds of the invention also serve as structural models for non-peptidic compounds with similar biological activity. Those of skill in the art recognize that a variety of techniques are available for constructing compounds with the same or similar desired biological activity as the lead peptide compound but with more favorable activity than the lead with respect to solubility, stability, and susceptibility to hydrolysis and proteolysis. See Morgan and Gainor (1989) Ann. Rep. Med. Chem. 24:243–252, incorporated herein by reference. These techniques include replacing the peptide backbone with a backbone composed of phosphonates, amidates, carbamates, sulfonamides, secondary amines, and N-methylamino acids.

IV. In Vitro Uses

The compounds of the invention are useful in vitro as unique tools for understanding the biological role of IL-1, including the evaluation of the many factors thought to influence, and be influenced by, the production of IL-1 and the receptor binding process. The present compounds are also useful in the development of other compounds that bind to the IL-1RtI, because the present compounds provide important information on the relationship between structure and activity that should facilitate such development.

The compounds are also useful as competitive inhibitors in assays to screen for new IL-1 receptor blockers. Specifically, the present invention includes peptides which bind the IL-1RtI, and wherein that binding is competitively inhibited by other peptides of the invention, e.g., those having the core sequences described herein. In such assay embodiments, the compounds of the invention can be used without modification or can be modified in a variety of ways; for example, by labeling, such as covalently or non-covalently joining a moiety which directly or indirectly provides a detectable signal. In any of these assays, the materials thereto can be labeled either directly or indirectly. Possibilities for direct labeling include label groups such as: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups. The compounds may also include spacers or linkers in cases where the compounds are to be attached to a solid support. Methods of determining whether a compound competitively inhibits IL-1 receptor binding of a peptide of the invention are well known in the art. See, e.g. Stryer, Biochemistry, W. H Freeman and Co. (1988).

Additionally, the peptides of the present invention may be used to label, and thereby ascertain and study the nature of the IL-1RtI/ligand interaction. In particular, those peptides which comprise p-benzoyl-L-phenylalanine derivatives within their sequence may be used to photolabel particular residues within the IL-1RtI sequence which are involved in the interaction and/or binding of the receptor's ligand. See, e.g., Kauer, et al., J.Biol. Chem. (1986) 261(23):10695–10700.

The compounds of the invention can also be used in assays as probes for determining the expression of the IL-1RtI on the surface of cells. Such an assay is useful for determining the degree of cellular immunological and inflammatory response, for example to infection and tissue injury. Typically, the cells under study will be exposed to the compounds for a period sufficient for the compounds to bind to the receptor(s) exposed on the cell surface. The cells are then separated from the non-bound compounds and unreacted cells, e.g., by affinity chromatography or the use of a cell sorter, to identify whether binding of the compounds to the receptor has occurred.

Thus, the compositions and methods of the present invention also can be used in vitro for testing a patient's susceptibility to varying treatment regimens for disorders associated with the overproduction of IL-1 or an improper response to IL-1 using an in vitro diagnostic method whereby a specimen is taken from the patient and is treated with a IL-1RtI binding, IL-1 blocking compound of the present invention to determine the effectiveness and amount of the compound necessary to produce the desired effect. The blocking compound and dosage can be varied. After the blocking compounds are screened, then the appropriate treatment and dosage can be selected by the physician and administered to the patient based upon the results.

Therefore, this invention also contemplates use of a blocking compound of this invention in a variety of diagnostic kits and assay methods.

V. In Vivo Uses

The compounds of the invention can also be administered to warm blooded animals, including humans, to block the binding of IL-1α or IL-1β to the IL-1RtI in vivo. Thus, the present invention encompasses methods for therapeutic treatment of IL-1 related disorders that comprise administering a compound of the invention in amounts sufficient to block or inhibit the binding of IL-1 to the IL-1R in vivo. For example, the peptides and compounds of the invention can be administered to treat symptoms related to the overproduction of IL-1 or an improper response to IL-1. Since the biological effects of IL-1 include immunologic properties, such as T-cell activation, increased IL-2R expression, B-cell activation via induction of IL-6, natural killer cell activity, and lymphokine gene expression; pro-inflammatory properties such as fever, sleep, anorexia, neuropeptide release, gene expression for complement, suppression of P450 synthesis, endothelial cell activation, neutrophilia, increased adhesion molecule expression, neutrophil priming, eosinophil degranulation, hypotension, myocardial suppression, neutrophil tissue infiltration, beta islet cell cytotoxicity, hyperlipidemia, cyclooxygenase and lipoxygenase gene expression, synthesis of collagenases and collagens, and osteoblast activation, the compositions and methods described herein will find use for the treatment and/or prevention of a variety of IL-1 related disorders. See, e.g., Dinarello (1991) *Blood* 8:1627–1652, which is incorporated herein by reference. Examples of specific disorders having such symptoms include but are not limited to, atherlerosclerosis, rheumatoid arthritis, osteoporosis, HIV infection and AIDS, bacterial infection, respiratory distress syndrome, acute myelogenous leukemia ("AML"), graft vs. host disease, coal miner pneumonoconiosis, alcoholic cirrhosis, cuprophane hemodialysis, cardiopulmonary bypass, chronic hepatitis B, thermal injury, reticulohistiocytosis, sarcoidosis, tuberculosis, obstructive jaundice, Paget's disease and osteomalacia, IDDM, Kawasaki's disease, inflammatory bowel disease, sepsis, toxic shock, and luteal phase.

Accordingly, the present invention includes pharmaceutical compositions comprising, as an active ingredient, at least one of the peptides or other compounds of the invention in association with a pharmaceutical carrier or diluent. The compounds of this invention can be administered by oral, parental (intramuscular, intraperitoneal, intravenous (IV) or subcutaneous injection), nasal, vaginal, rectal, or sublingual routes of administration and can be formulated in dosage forms appropriate for each route of administration.

Solid dosage forms for oral administration include capsules, tablets, pills, powders, and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parental administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

The quantities of the IL-1 blocking compound necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman et al. (eds), (1990) *Goodman and Gilman's: The Pharmacological Basis of Therapeutics*, 8th ed., Pergamon Press; and *Remington's Pharmaceutical Sciences*, (1985) 7th ed., Mack Publishing Co., Easton, Pa.; each of which is hereby incorporated by reference.

The dosage of active ingredient in the compositions of this invention may be varied; however, it is necessary that the amount of the active ingredient shall be such that a suitable dosage form is obtained. For the IL-1 blocking compounds of the invention exhibiting high affinity binding with IL-1 receptor, low dosages would be initially expected to be effective. Thus, generally dosage levels of between about 0.001 and 10 mg/kg, preferably between about 0.01 to 10 mg/kg, and more preferably between about 0.1 and 10 mg/kg of body weight daily will be administered to mammals to obtain effective IL-1 blocking activity.

It should, of course, be understood that the compositions and methods of this invention can be used in combination with other agents exhibiting the ability to modulate IL-1 synthesis, release, and/or binding. Examples of such agents include, but are not limited to disease modifying antirheumatic drugs chloroquine, auranofin, sodium aurothiomalate, and dexamethasone (see, e.g., Lee et al. (1988) *Proc. Natl. Acad. Sci.* 85:1204); tenidap (see, e.g., Otterness, 3rd Interscience World Conference on Inflammation, Monte-Carlo, Abstr. p. 371 (March, 1989); antioxidants, such as nordihydroguaiaretic acid (see, e.g., Lee et al. (1988) *Int. J. Immunopharmacol.* 10:835), probucol (see, e.g., Ku et al. (1988) *Am. J. Cardiol.* 62:778), and disulfiram (see, e.g., Marx (1988) *Science* 239:257); pentoxifylline (see, e.g., Sullivan et al. (1988) *Infect. Tmmun.* 56:1722); denbufylline (see, e.g., Mandell et al. PCT publication WO 89/015145 (1989);

romazarit (see, e.g., Machin et al. (1988) U.S. Pat. No. 4,774,253); tiaprofenic acid; dexamethasone; and natural macromolecular IL-1 inhibitors (see, e.g., Rosenstreich et al. in "*Lymphokines*", E. Pick, Ed., 14:6 Academic Press (1987) and Larrick (1989) *Immunol. Today* 10:6); as well as the other agents described in Bender and Lee (1989) *Annual Reports in Medicinal Chemistry* Chapter 20: *Pharmacological Modulation of Interleukin-1*, pp. 185-193, which is incorporated herein by reference.

The compositions containing the compounds can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose." Amounts effective for this use will depend on the severity of the disease and the weight and general state of the patient.

In prophylactic applications, compositions containing the compounds of the invention are administered to a patient susceptible to or otherwise at risk of a particular disease. Such an amount is defined to be a "prophylactically effective dose." In this use, the precise amounts again depend on the patient's state of health and weight.

As can be appreciated from the disclosure above, the present invention has a wide variety of applications. Accordingly, the following examples are offered by way of illustration, not by way of limitation.

EXAMPLE 1

Solid Phase Peptide Synthesis

All peptides were synthesized using standard solid phase synthesis methods (see, e.g., Merrifield, J. Am. Chem. Soc. (1963) 85:2149) with the aid of an Applied Biosystems Inc. Model 431A peptide synthesizer. The synthesis was performed with PAL resin or HMP resin serving as an insoluble support that generated respectively a carboxamide or a carboxylic acid C-terminal in the final product. Most reagents, resins and protected amino acids (free or on resin) were purchased from Millipore or Applied Biosystems Inc. The fluorenylmethyloxycarbonyl group (Fmoc) was used for amino protection during the coupling procedure. Reactive side chain protections were as follows: Arg, 2,2,5,7,8-pentamethylchroman-6-sulfonyl (Pmc); Glu and Asp, o-t-butyl; Ser, Thr, Tyr, o-t-butyl; Trp, N-t-butyloxycarbonyl; His, Gln, N-trityl; and Cys, S-trityl.

The peptides were assembled using the standard protocols of the Applied Biosystems Inc. System Software, version 1.0. Removal of the peptides from the resin and simultaneous deprotection of the side chain functions were achieved by treatment with reagent K or slight modifications thereof. The deprotected peptides were precipitated with diethylether. In all cases, purification was by preparative, reverse phase, HPLC on a $C_{18}$ bonded silicagel column. The homogenous peptides were characterized by Fast Atom Bombardment mass spectrometry or electrospray mass spectrometry and amino acid analysis, when applicable.

EXAMPLE 2

A. Prostaglandin $E_2$ ($PGE_2$) Response Assay

Some of the peptides were tested for ability to block the IL-1α induced $PGE_2$ response in human foreskin fibroblasts. IL-1α is known to stimulate the production of $PGE_2$ by normal human fibroblasts, and an assay for $PGE_2$ is available from Amersham (see the instruction manual for the Prostaglandin $E_2[^{125}I]$ scintillation proximity assay (SPA) system, code RPA 539, incorporated herein by reference. Except as otherwise noted below, the assay was carried out according to the manufacturer's instructions and with the reagents supplied in the kit.

For use in the assay, the cells should be actively growing at near confluence in 96 well tissue culture plates. Typically, cells were kept at about 60% confluency under "starved" conditions (low serum in the media) until needed for the assay. One day before the assay, as many wells as needed for the assay were seeded with about $1.5 \times 10^4$ cells per well in 100 μl of DMEM/F12 (a 1:1 mixture of the two medias, supplied by JRH Biosciences) plus 10% fetal bovine serum (FBS, supplied by Hyclone) and antibiotics (penicillin and streptomycin, P/S) to allow the cells to begin active growth.

Each peptide in powder form was individually dissolved in DMEM/F12 containing 1% FBS and P/S to a final concentration of about 675 μM. 12 wells of a microtiter dish were typically used to assay each peptide. The media was removed from the cells (the cells were not washed) with a pipettor, and 140 μl of the peptide solution were added to half of the wells (i.e. peptide was added to a set of 6 wells and the other set of 6 wells served as the control), and the plate was incubated for 30 minutes at 37° C. Then, 10 μl of a 15 pM solution of IL-1α (in the same DMEM solution as the peptide) were added to half of the wells containing peptide (i.e., typically 3 wells) and half of the wells with no peptide (i.e., 3 wells). About 10 μl of media were added to the wells which did not contain the IL-1α solution, and the plate was incubated for 6 hours at 37° C. Thus, for each peptide, the 3 wells of the microtiter dish contained no peptide and no IL-1α; 3 wells contained no peptide and IL-1α; 3 wells contained peptide and no IL-1α; and 3 wells contained peptide and IL-1α.

About 100 μl of media from each microtiter well (the sample) were added to 100 μl of the methyl oximation reagent, and the resulting mixture was incubated at 60° C. for one hour. About 300 μl of assay buffer were then added to each sample, and the sample was vortexed to ensure complete mixing. About 100 μl of the resulting sample were added to a labeled 1.5 ml Eppendorf™ tube. About 200 μl of assay buffer were added to two tubes labelled NSB (non-specific binding). About 100 μl of assay buffer were added to two tubes labelled $B_0$ ($B_0$ is equal to the number of counts (cpm of $^{125}I$) bound to the bead in the absence of $PGE_2$). About 100 μl of tracer ($^{125}I$-$PGE_2$-methyloximate; the methyloximate derivative of $PGE_2$ is more stable than $PGE_2$) are added to each tube, and 100 μl of anti-methyloximate $PGE_2$ antisera were added to all tubes except the NSB tubes. Then, about 100 μl of beads, which contain the scintillant and are coated with Protein A, were added to each tube.

The Protein A binds to the antisera, and the antisera binds to the $^{125}I$-$PGE_2$-methyloximate. Unlabeled $PGE_2$, the production of which is stimulated by IL-1α, competes with the $^{125}I$-$PGE_2$-methyloximate, thus reducing the total $^{125}I$ cpm bound to the bead. $PGE_2$ concentration was calculated from a standard curve as described in the Amersham $PGE_2$ SPA assay instruction manual. The results indicated that at least some of the peptides did inhibit the $PGE_2$ response to 1 pM IL-1 after 3 hours and 6 hours incubation.

B. Epidermal Growth Factor Receptor Down Regulation Assay

The protocol set forth in Bird and Saklatvala (1989) *J. Immunol.* 142:126–133, which is incorporated herein by reference, was also used to demonstrate the activity of the compounds of the present invention. This assay examines the effect of the compounds of the invention on the IL-1 induced down-regulation of the epidermal growth factor (EGF) receptor as measured by the binding of $^{125}$I-labeled EGF to its receptor in normal human dermal fibroblasts (NHDF). Incubation of the cells with the compounds of the present invention at 37° C., in the presence of IL-1α showed no decrease in the cells ability to subsequently bind sub-saturating levels of $^{125}$I-labeled epidermal growth factor, whereas incubation in the presence of IL-1α alone, resulted in a decrease in EGF binding. The table below lists the approximate concentration of representative peptides of the invention which blocked 50% of the IL-1 induced down regulation of the EGF receptor. IC50 values are indicated symbolically by the symbols "–", "+", and "++". For example, those peptides which showed IC50 values in excess of 100 μM are indicated with a "–". Those peptides which give IC50 values of less than or equal to 100 μM are given a "+", while those which give IC50 values of 500 nM or less are indicated with a "++". Those peptides which give IC50 values at or near the cutoff point for a particular symbol are indicated with a hybrid, e.g. "+/–". Those peptides for which IC50 values were not determined are listed as "N.D".

TABLE 35

| Peptide | IC$_{50}$ |
| --- | --- |
| ETPFTWEESNAYYWQPYALPL (SEQ ID NO:13) | ++ |
| TFVYWQJYALPL (SEQ ID NO:352) | – |
| TFvYWQPYALPL$^2$ | – |
| YIPFTWEESNAYYWQPYALPL (SEQ ID NO:353) | ++ |
| DGYDRWRQSGERYWQPYALPL (SEQ ID NO:354) | ++ |
| pY(1Nap)-pY-QJYALPL (SEQ ID NO:330) | ++ |
| TANVSSFEWTPGYWQPYALPL (SEQ ID NO:11) | ++ |
| FEWTPGYWQJYALPL (SEQ ID NO:356) | ++ |
| FEWTPGYWQPYALPLSD-NH$_2$ (SEQ ID NO:357) | ++ |
| FEWTPGYYQJYALPL (SEQ ID NO:358) | ++ |
| FEWTPGYWQJY-NH$_2$ (SEQ ID NO:316) | + |
| AcFEWTPGYWQJY-NH$_2$ (SEQ ID NO:324) | + |
| AcFEWTPGWYQJY-NH$_2$ (SEQ ID NO:318) | ++/+ |
| AcFEWTPGYYQJY-NH$_2$ (SEQ ID NO:359) | ++/+ |
| AcFEWTPaYWQJY-NH$_2$ | + |
| AcFEWTPaWYQJY-NH$_2$ | + |
| AcFEWTPaYYQJY-NH$_2$ | + |

1Nap denotes 1-naphthylalanine and NH$_2$ denotes an amide group, e.g., a carboxamide.
$^2$d-Valine is used at the 3-position.

C. Peptide Effects on IL-1 Induced E-Selectin (HUVEC Cells)

The compounds of the present invention were assayed for their ability to inhibit the expression of IL-1 induced E-selectin in HUVEC cells (human umbilical vein endothelial cells). HUVEC cells are grown to confluency in the wells of a 24-well microtiter plate. The compounds were serially diluted in DMEM/F12+0.1% BSA ("SFM") with 120 pM IL-1α. The cells were washed and then incubated with IL-1α and the compound to be tested for 15 minutes. The cells were again washed and incubated in SFM for 4 hours. The cells were washed and incubated with anti-selectin antibody for 30 minutes. Following antibody incubation, the cells were incubated with $^{125}$I Protein A and washed. The amount of $^{125}$I bound to the cells was then determined. The concentration of compounds required to inhibit 50% of IL-1 induced E-selectin expression is shown below.

TABLE 36

| Peptide | IC$_{50}$ |
| --- | --- |
| FEWTPGYYQJYALPL (SEQ ID NO:358) | ++ |
| FEWTPGYWQJYALPL (SEQ ID NO:356) | ++ |
| FEWTPGWYQJYALPL (SEQ ID NO:409) | ++ |
| TANVSSFEWTPGYWQPYALPL (SEQ ID NO:11) | ++ |
| AcFEWTPGYWQJY-NH$_2$ (SEQ ID NO:324) | ++ |
| AcFEWTPGWYQJY-NH$_2$ (SEQ ID NO:318) | ++ |
| AcFEWTPGYYQJY-NH$_2$ (SEQ ID NO:359) | ++ |
| AcFEWTPaYWQJY-NH$_2$ | ++ |
| AcFEWTPaWYQJY-NH$_2$ | ++ |
| AcFEWTPaYYQJY-NH$_2$ | ++ |

D. Other Assays

Other biological assays that can be used to demonstrate the activity of the compounds of the present invention are disclosed in Dripps et al., (1991) *J. Biol. Chem.* 266(16):10331–10336, and Bird et al. (1991) *J. Biol. Chem.* 266(33):22662–22670, each of which is incorporated herein by reference.

EXAMPLE 3

Determination of Concentration Effecting Inhibition of IL-1α Binding

This example provides the results of experiments conducted to determine an approximate IC$_{50}$ for certain peptides of the invention. IC$_{50}$ as used herein refers to the concentration of a compound which will inhibit 50% of the binding between a receptor and its ligand, e.g. IL-1RtI and IL-1. Stock solutions of each peptide were prepared. The appropriate amount of the peptide was dissolved in DMSO, and then nineteen volumes of binding buffer (RPMI 1640, 1% BSA, 20 mM HEPES, pH 7.2–7.3, and 0.1% sodium azide) were added to yield a 1 mM peptide, 5% DMSO stock solution.

One assay utilized a truncated IL-1RtI which had been immobilized on 96-well plates with an appropriate antibody, typically a non-blocking high affinity antibody. In other assays, cells expressing "full-length" IL-1RtI were used with results that yielded IC$_{50}$ values about 5 to 10 fold lower than those determined using the truncated receptor. The cells were seeded onto Falcon 3072 96-well plates at about 10$^5$ cells per well, and the plates were incubated overnight at 37° C. in media containing serum. The following morning, the cells were checked to ensure that the cells were confluent and adhered to the bottom of the wells.

According to either assay protocol, the plates were then washed three times with binding buffer, and then 50 μl of binding buffer and 25 μl of a peptide solution (either the stock solution or a dilution thereof; each stock was subjected to five three fold dilutions) were added to each well. Then 25 μl of binding buffer containing $^{125}$I-IL-1α (final concentration of 90 pM) were added to each well to begin the assay. Each assay was carried out in duplicate. The plates were then incubated for two hours at 40C. For peptides having particularly high affinities, the assay was run in 24 well plates allowing for higher levels of ligand (possible total volume of 2.5 ml instead of 100 μl in the 96 well plate), thereby minimizing the potential for ligand depletion.

After the two hour incubation, the wells were rinsed three times with ice cold PBS (a semi-automated cell harvesting device was used to conduct the rinse). The receptors or cells were then detached from the plates by adding 100 μl of 0.1N NaOH to each well and incubating the plates at room temperature for 20 minutes. After the 20 minute incubation, about 75 μl of the suspension was counted on a gamma counter, and the IC$_{50}$ for each peptide was determined using computer assistance and the results of the gamma counting.

All publications and patent documents cited in this application are incorporated by reference in their entirety for all purposes to the same extent as if each individual publication or patent document were so individually denoted.

We claim:

1. A method of antagonizing action of Interleukin-1 on an interleukin-1 type I receptor, the method comprising contacting the receptor with a compound that binds to an interleukin-1 type I receptor having from about 11 to 40 amino acids in length and a core sequence of amino selected from the group consisting of:

FEWTPGYWQPY-NH2 (SEQ ID NO:315);
FEWTPGYWQHY-NH2 (SEQ ID NO:316);
FEWTPGWYQJY-NH2 (SEQ ID NO:317);
AcFEWTPGWYQJY-NH2 (SEQ ID NO:318);
FEWTPGW-pY-QJY-NH2 (SEQ ID NO:319);
FAWTPGYWQJY-NH2 (SEQ ID NO.320);
FEWAPGYWQJY-NH2 (SEQ ID NO:321);
FEWVPGYWQJY-NH2 (SEQ ID NO:322);
FEWTPGYWQJY-NH2 (SEQ ID NO:323);
AcFEWTPGYWQJY-NH (SEQ ID NO:324);
FEWTPaWYQJY-NH2; FEWTP-Sar-WYQJY-NH2 (SEQ ID NO:326); FEWTPGYYQPY-NH2 (SEQ ID NO:327); FEWTPGWWQPY-NH2 (SEQ ID NO:328); FEWTPNYWQPY-NH2 (SEQ ID NO:329); FEWTPvYWQJY-NH2; FEWT-Pec-GYWQJY-NH$_2$ (SEQ ID NO:347); FEWTP-Aib-YWQJY-NH$_2$ (SEQ ID NO:348); FEWT-Sar-GYWQJY-NH$_2$ (SEQ NO:349); FEWTPGYWQPYALPL (SEQ ID NO:331); 1-Nap-EWTPGYYQJY-NH$_2$ (SEQ ID NO:367); YEWTPGYYQJY-NH$_2$ (SEQ ID NO:368); FEWVPGYYQJY-NH$_2$ (SEQ ID NO:369); FEWTPsYYQJY-NH$_2$; AND FEWTPnYYQJY-NH$_2$; where AcF is acetylated phenylalanine, Y-NH2 is tyrosinamide, -pY- is phosphotyrosine, -Sar- is sarcosine, -Pec- is pipecolic acid, a is d-alanine, v is d-valine, d is d-asparagine, s is d-serine, and -Aib- is aminoisobutyric acid.

* * * * *